US012685663B2

(12) United States Patent
Johannes et al.

(10) Patent No.: US 12,685,663 B2
(45) Date of Patent: Jul. 21, 2026

(54) FLUID COLLECTION DEVICES INCLUDING AN ENLARGED BASE, AND SYSTEMS AND METHODS OF USE

(71) Applicant: PureWick Corporation, El Cajon, CA (US)

(72) Inventors: Ashley Marie Johannes, Statham, GA (US); Kathleen Davis, Atlanta, GA (US); Maria Renee Ramos Rodriguez, Florham Park, NJ (US)

(73) Assignee: PureWick Corporation, Covington, GA (US)

( * ) Notice: Subject to any disclaimer, the term of this patent is extended or adjusted under 35 U.S.C. 154(b) by 1304 days.

(21) Appl. No.: 17/394,055

(22) Filed: Aug. 4, 2021

(65) Prior Publication Data

US 2022/0039995 A1     Feb. 10, 2022

Related U.S. Application Data

(60) Provisional application No. 63/061,241, filed on Aug. 5, 2020.

(51) Int. Cl.
A61F 5/455     (2006.01)
A61M 1/00     (2006.01)

(52) U.S. Cl.
CPC ............... A61F 5/455 (2013.01); A61M 1/60 (2021.05)

(58) Field of Classification Search
CPC ................................ A61F 15/455; A61M 1/60
USPC ........................................................ 604/329
See application file for complete search history.

(56) References Cited

U.S. PATENT DOCUMENTS

| 737,443 | A | 8/1903 | Mooers |
| 1,015,905 | A | 1/1912 | Northrop |
| 1,032,841 | A | 7/1912 | Koenig |
| 1,178,644 | A | 4/1916 | Johnson |
| 1,387,726 | A | 8/1921 | Karge |
| 1,742,080 | A | 12/1929 | Jones |
| 1,979,899 | A | 11/1934 | Obrien et al. |
| 2,241,010 | A | 5/1941 | Chipley |
| 2,262,772 | A | 11/1941 | Peder |

(Continued)

FOREIGN PATENT DOCUMENTS

| AU | 2018216821 A1 | 8/2019 |
| AU | 2021299304 A1 | 2/2023 |

(Continued)

OTHER PUBLICATIONS

US 9,908,683 B2, 03/2018, Sandhausen et al. (withdrawn)

(Continued)

Primary Examiner — Andrew J Mensh
(74) Attorney, Agent, or Firm — Ballard Spahr LLP

(57)          ABSTRACT

Example fluid collection devices and methods of using the fluid collection devices are described. The fluid collection devices include a fluid impermeable barrier, an enlarged base, and a fluid permeable body. The fluid impermeable barrier has a first lateral dimension and at least partially defining a chamber, an aperture configured to receive a conduit therethrough, and an opening. The base extends from the fluid impermeable barrier distal to the aperture and has a second lateral dimension greater than the first lateral dimension. The fluid permeable body is positioned at least partially within the chamber to extend across at least a portion of the opening.

41 Claims, 12 Drawing Sheets

(56)　　　　　References Cited

U.S. PATENT DOCUMENTS

| | | | |
|---|---|---|---|
| 2,326,881 A | 8/1943 | Packer | |
| 2,379,346 A | 6/1945 | Farrell | |
| 2,485,555 A | 10/1949 | Bester | |
| 2,571,357 A * | 10/1951 | Gemora | A61F 13/64 |
| | | | 604/397 |
| 2,613,670 A | 10/1952 | Edward | |
| 2,616,426 A | 11/1952 | Adele | |
| 2,644,234 A | 7/1953 | Earl | |
| 2,648,335 A | 8/1953 | Chambers | |
| 2,789,560 A | 4/1957 | Weimer | |
| 2,859,786 A | 11/1958 | Tupper | |
| 2,944,551 A | 7/1960 | Carl | |
| 2,968,046 A | 1/1961 | Duke | |
| 2,971,512 A | 2/1961 | Reinhardt | |
| 3,032,038 A | 5/1962 | Swinn | |
| 3,077,883 A | 2/1963 | Hill | |
| 3,087,938 A | 4/1963 | Hans et al. | |
| 3,114,916 A | 12/1963 | Hadley | |
| 3,169,528 A | 2/1965 | Knox et al. | |
| 3,171,506 A | 3/1965 | Therkel | |
| 3,175,719 A | 3/1965 | Herndon | |
| 3,194,238 A | 7/1965 | Breece | |
| 3,198,994 A | 8/1965 | Hildebrandt et al. | |
| 3,221,742 A | 12/1965 | Egon | |
| 3,312,221 A | 4/1967 | Overment | |
| 3,312,981 A | 4/1967 | Mcguire et al. | |
| 3,349,768 A | 10/1967 | Keane | |
| 3,362,590 A | 1/1968 | Gene | |
| 3,366,116 A | 1/1968 | Huck | |
| 3,368,564 A | 2/1968 | Selix | |
| 3,398,848 A | 8/1968 | Donovan | |
| 3,400,717 A | 9/1968 | Bruce et al. | |
| 3,406,688 A | 10/1968 | Bruce | |
| 3,424,163 A | 1/1969 | Gravdahl | |
| 3,425,471 A | 2/1969 | Yates | |
| 3,434,565 A | 3/1969 | Fischer | |
| 3,511,241 A | 5/1970 | Lee | |
| 3,512,185 A | 5/1970 | Ellis | |
| 3,520,300 A | 7/1970 | Flower | |
| 3,528,423 A | 9/1970 | Lee | |
| 3,608,552 A | 9/1971 | Broerman | |
| 3,613,123 A | 10/1971 | Langstrom | |
| 3,648,700 A | 3/1972 | Warner | |
| 3,651,810 A | 3/1972 | Ormerod | |
| 3,661,155 A | 5/1972 | Lindan | |
| 3,683,918 A | 8/1972 | Pizzella | |
| 3,699,815 A | 10/1972 | Holbrook | |
| 3,721,243 A | 3/1973 | Greth et al. | |
| 3,726,277 A | 4/1973 | Hirschman | |
| 3,742,952 A | 7/1973 | Magers et al. | |
| 3,742,953 A | 7/1973 | Lee | |
| 3,757,355 A | 9/1973 | Allen et al. | |
| 3,788,324 A | 1/1974 | Lim | |
| 3,843,016 A | 10/1974 | Bornhorst et al. | |
| 3,863,638 A | 2/1975 | Rogers et al. | |
| 3,863,798 A | 2/1975 | Kurihara et al. | |
| 3,864,759 A | 2/1975 | Horiuchi | |
| 3,865,109 A | 2/1975 | Elmore et al. | |
| 3,881,486 A | 5/1975 | Fenton | |
| 3,881,489 A | 5/1975 | Hartwell | |
| 3,915,189 A | 10/1975 | Holbrook et al. | |
| 3,931,650 A | 1/1976 | Miller | |
| 3,964,786 A | 6/1976 | Mashuda | |
| 3,998,228 A | 12/1976 | Poidomani | |
| 3,999,550 A | 12/1976 | Martin | |
| 4,006,793 A | 2/1977 | Robinson | |
| 4,015,604 A | 4/1977 | Csillag | |
| 4,020,843 A | 5/1977 | Kanall | |
| 4,022,211 A | 5/1977 | Timmons et al. | |
| 4,022,213 A | 5/1977 | Stein | |
| 4,027,776 A | 6/1977 | Douglas | |
| 4,031,897 A | 6/1977 | Graetz | |
| 4,064,962 A | 12/1977 | Hunt | |
| 4,069,817 A | 1/1978 | Fenole et al. | |
| 4,084,589 A | 4/1978 | Kulvi | |
| 4,096,897 A | 6/1978 | Cammarata | |
| 4,116,197 A | 9/1978 | Bermingham | |
| 4,140,739 A | 2/1979 | Cotten | |
| 4,180,178 A | 12/1979 | Turner | |
| 4,187,953 A | 2/1980 | Turner | |
| 4,194,508 A | 3/1980 | Anderson | |
| 4,197,849 A | 4/1980 | Bostick | |
| 4,200,102 A | 4/1980 | Duhamel et al. | |
| 4,202,058 A | 5/1980 | Anderson | |
| 4,203,503 A | 5/1980 | Bertotti et al. | |
| 4,209,076 A | 6/1980 | Bertotti et al. | |
| 4,223,677 A | 9/1980 | Anderson | |
| 4,233,025 A | 11/1980 | Larson et al. | |
| 4,233,978 A | 11/1980 | Hickey | |
| 4,246,901 A | 1/1981 | Frosch et al. | |
| 4,253,542 A | 3/1981 | Ruspa et al. | |
| 4,257,418 A | 3/1981 | Hessner | |
| 4,270,539 A | 6/1981 | Frosch et al. | |
| 4,280,498 A | 7/1981 | Jensen | |
| 4,281,655 A | 8/1981 | Terauchi | |
| 4,292,916 A | 10/1981 | Bradley et al. | |
| 4,330,239 A | 5/1982 | Gannaway | |
| 4,345,341 A | 8/1982 | Saito | |
| 4,349,029 A | 9/1982 | Mott | |
| 4,352,356 A | 10/1982 | Tong | |
| 4,356,012 A | 10/1982 | Hofstetter | |
| 4,360,933 A | 11/1982 | Kimura et al. | |
| 4,365,363 A | 12/1982 | Windauer | |
| 4,375,841 A | 3/1983 | Vielbig | |
| 4,387,726 A | 6/1983 | Denard | |
| 4,403,991 A | 9/1983 | Hill | |
| 4,421,511 A | 12/1983 | Steer et al. | |
| 4,425,130 A | 1/1984 | Desmarais | |
| 4,446,986 A | 5/1984 | Bowen et al. | |
| 4,453,938 A | 6/1984 | Brendling | |
| 4,457,314 A | 7/1984 | Knowles | |
| 4,457,758 A | 7/1984 | Norton | |
| 4,476,879 A | 10/1984 | Jackson | |
| 4,512,771 A | 4/1985 | Norton | |
| 4,526,688 A | 7/1985 | Schmidt et al. | |
| 4,528,703 A | 7/1985 | Kraus | |
| 4,533,354 A | 8/1985 | Jensen et al. | |
| 4,533,357 A * | 8/1985 | Hall | A61F 13/472 |
| | | | 604/401 |
| D280,438 S | 9/1985 | Wendt | |
| 4,551,141 A | 11/1985 | Mcneil | |
| 4,553,968 A | 11/1985 | Komis | |
| 4,568,341 A | 2/1986 | Mitchell et al. | |
| 4,581,026 A | 4/1986 | Schneider | |
| 4,583,983 A | 4/1986 | Einhorn et al. | |
| 4,589,516 A | 5/1986 | Inoue et al. | |
| 4,601,716 A | 7/1986 | Smith | |
| 4,610,675 A | 9/1986 | Triunfol | |
| 4,620,333 A | 11/1986 | Ritter | |
| 4,626,250 A | 12/1986 | Schneider | |
| 4,627,846 A | 12/1986 | Ternstroem | |
| 4,631,061 A | 12/1986 | Martin | |
| 4,650,477 A | 3/1987 | Johnson | |
| 4,655,754 A | 4/1987 | Richmond et al. | |
| 4,656,675 A | 4/1987 | Fajnsztajn | |
| 4,681,570 A | 7/1987 | Dalton | |
| 4,681,572 A | 7/1987 | Tokarz et al. | |
| 4,681,577 A * | 7/1987 | Stern | A61F 13/47 |
| | | | D24/126 |
| 4,692,160 A | 9/1987 | Nussbaumer | |
| 4,707,864 A | 11/1987 | Ikematsu et al. | |
| 4,713,065 A | 12/1987 | Koot | |
| 4,713,066 A | 12/1987 | Komis | |
| 4,723,953 A | 2/1988 | Pratt et al. | |
| 4,735,841 A | 4/1988 | Sourdet | |
| 4,743,236 A | 5/1988 | Manschot | |
| 4,747,166 A | 5/1988 | Kuntz | |
| 4,752,944 A | 6/1988 | Conrads et al. | |
| 4,759,753 A | 7/1988 | Schneider et al. | |
| 4,769,215 A | 9/1988 | Ehrenkranz | |
| 4,771,484 A | 9/1988 | Mozell | |
| 4,772,280 A | 9/1988 | Rooyakkers | |
| 4,775,458 A | 10/1988 | Forester | |
| 4,784,654 A | 11/1988 | Beecher | |

(56)     References Cited

U.S. PATENT DOCUMENTS

| | | | |
|---|---|---|---|
| 4,790,830 A | 12/1988 | Hamacher | |
| 4,790,835 A | 12/1988 | Elias | |
| 4,791,686 A | 12/1988 | Taniguchi et al. | |
| 4,795,449 A | 1/1989 | Schneider et al. | |
| 4,798,603 A | 1/1989 | Meyer et al. | |
| 4,799,928 A | 1/1989 | Crowley | |
| 4,804,377 A | 2/1989 | Hanifl et al. | |
| 4,812,053 A | 3/1989 | Bhattacharjee | |
| 4,813,943 A | * 3/1989 | Smith | A61F 5/4408 |
| | | | 604/350 |
| 4,820,291 A | 4/1989 | Terauchi et al. | |
| 4,820,297 A | 4/1989 | Kaufman et al. | |
| 4,841,728 A | 6/1989 | Jean et al. | |
| 4,846,818 A | 7/1989 | Keldahl et al. | |
| 4,846,819 A | * 7/1989 | Welch | A61F 5/455 |
| | | | 604/336 |
| 4,846,824 A | 7/1989 | Schultz et al. | |
| 4,846,909 A | 7/1989 | Klug et al. | |
| 4,865,595 A | 9/1989 | Heyden | |
| 4,880,417 A | 11/1989 | Yabrov et al. | |
| 4,882,794 A | 11/1989 | Stewart | |
| 4,883,465 A | 11/1989 | Brennan | |
| 4,886,498 A | 12/1989 | Newton | |
| 4,886,508 A | 12/1989 | Washington | |
| 4,886,509 A | 12/1989 | Mattsson | |
| 4,889,532 A | 12/1989 | Metz et al. | |
| 4,889,533 A | 12/1989 | Beecher | |
| 4,890,691 A | 1/1990 | Ching-Ho | |
| 4,895,140 A | 1/1990 | Bellak | |
| 4,903,254 A | 2/1990 | Haas | |
| 4,904,248 A | 2/1990 | Vaillancourt | |
| 4,905,692 A | 3/1990 | More | |
| 4,911,262 A | 3/1990 | Tani et al. | |
| 4,930,997 A | 6/1990 | Bennett | |
| 4,936,838 A | * 6/1990 | Cross | A61F 5/455 |
| | | | 600/574 |
| 4,950,262 A | 8/1990 | Takagi | |
| 4,955,922 A | 9/1990 | Terauchi | |
| 4,957,487 A | 9/1990 | Gerow | |
| 4,965,460 A | 10/1990 | Tanaka et al. | |
| 4,986,823 A | 1/1991 | Anderson et al. | |
| 4,987,849 A | 1/1991 | Sherman | |
| 5,002,541 A | 3/1991 | Conkling et al. | |
| 5,004,463 A | 4/1991 | Nigay | |
| 5,013,308 A | 5/1991 | Sullivan et al. | |
| 5,031,248 A | 7/1991 | Kemper | |
| 5,045,077 A | 9/1991 | Blake | |
| 5,045,283 A | 9/1991 | Patel | |
| 5,049,144 A | 9/1991 | Payton | |
| 5,053,339 A | 10/1991 | Patel | |
| 5,057,092 A | 10/1991 | Webster | |
| 5,058,088 A | 10/1991 | Haas et al. | |
| 5,071,347 A | 12/1991 | Mcguire | |
| 5,078,707 A | 1/1992 | Peter | |
| 5,084,037 A | 1/1992 | Barnett | |
| 5,100,396 A | 3/1992 | Zamierowski | |
| 5,102,404 A | 4/1992 | Goldberg et al. | |
| 5,112,324 A | 5/1992 | Wallace | |
| 5,134,994 A | 8/1992 | Say | |
| 5,137,033 A | 8/1992 | Norton | |
| 5,147,301 A | 9/1992 | Ruvio | |
| 5,176,667 A | 1/1993 | Debring | |
| 5,195,997 A | 3/1993 | Carns | |
| 5,196,654 A | 3/1993 | Diflora et al. | |
| 5,199,444 A | 4/1993 | Wheeler | |
| 5,203,699 A | 4/1993 | Mcguire | |
| 5,244,458 A | 9/1993 | Takasu | |
| 5,246,454 A | 9/1993 | Peterson | |
| 5,267,988 A | 12/1993 | Farkas | |
| 5,275,307 A | 1/1994 | Freese | |
| 5,282,795 A | 2/1994 | Finney | |
| 5,294,983 A | 3/1994 | Ersoz et al. | |
| 5,295,979 A | 3/1994 | Delaurentis et al. | |
| 5,295,983 A | 3/1994 | Kubo | |
| 5,300,052 A | 4/1994 | Kubo | |
| 5,304,749 A | 4/1994 | Crandell | |
| 5,312,383 A | 5/1994 | Kubalak | |
| 5,318,550 A | 6/1994 | Cermak et al. | |
| 5,330,457 A | 7/1994 | Cohen | |
| 5,330,459 A | 7/1994 | Lavon et al. | |
| 5,334,174 A | 8/1994 | Street | |
| 5,334,176 A | 8/1994 | Buenger et al. | |
| 5,340,840 A | 8/1994 | Park et al. | |
| 5,382,244 A | 1/1995 | Telang | |
| 5,397,315 A | 3/1995 | Schmidt et al. | |
| 5,409,014 A | 4/1995 | Napoli et al. | |
| 5,409,475 A | 4/1995 | Steer | |
| 5,411,495 A | 5/1995 | Willingham | |
| 5,423,784 A | 6/1995 | Metz | |
| 5,423,788 A | 6/1995 | Rollins et al. | |
| 5,437,836 A | 8/1995 | Yamada | |
| 5,456,246 A | 10/1995 | Schmieding et al. | |
| 5,466,229 A | 11/1995 | Elson et al. | |
| 5,478,334 A | 12/1995 | Bernstein | |
| 5,499,977 A | 3/1996 | Marx | |
| 5,543,042 A | 8/1996 | Filan et al. | |
| D373,928 S | 9/1996 | Green | |
| 5,582,604 A | 12/1996 | Ahr et al. | |
| 5,592,950 A | 1/1997 | Kopelowicz | |
| 5,593,389 A | 1/1997 | Chang | |
| 5,605,161 A | 2/1997 | Cross | |
| 5,614,699 A | 3/1997 | Yashiro et al. | |
| 5,618,277 A | 4/1997 | Goulter | |
| 5,628,735 A | 5/1997 | Skow | |
| 5,632,736 A | 5/1997 | Block | |
| 5,636,643 A | 6/1997 | Argenta et al. | |
| 5,637,104 A | 6/1997 | Ball et al. | |
| 5,662,633 A | 9/1997 | Doak et al. | |
| 5,674,212 A | 10/1997 | Osborn et al. | |
| 5,678,564 A | 10/1997 | Lawrence et al. | |
| 5,678,654 A | 10/1997 | Uzawa | |
| 5,681,297 A | 10/1997 | Hashimoto et al. | |
| 5,687,429 A | 11/1997 | Rahlff | |
| 5,695,485 A | 12/1997 | Duperret et al. | |
| 5,700,254 A | 12/1997 | Mcdowall et al. | |
| 5,701,612 A | 12/1997 | Daneshvar | |
| 5,705,777 A | 1/1998 | Flanigan et al. | |
| 5,735,835 A | 4/1998 | Holland | |
| 5,735,837 A | 4/1998 | Ishikawa | |
| 5,752,944 A | 5/1998 | Dann et al. | |
| 5,763,333 A | 6/1998 | Suzuki et al. | |
| 5,772,644 A | 6/1998 | Bark et al. | |
| 5,792,132 A | 8/1998 | Garcia | |
| 5,827,243 A | 10/1998 | Palestrant | |
| 5,827,247 A | 10/1998 | Kay | |
| 5,827,250 A | 10/1998 | Fujioka et al. | |
| 5,827,257 A | 10/1998 | Fujioka et al. | |
| D401,699 S | 11/1998 | Herchenbach et al. | |
| 5,859,393 A | 1/1999 | Cummins et al. | |
| 5,865,378 A | 2/1999 | Hollinshead et al. | |
| 5,873,869 A | 2/1999 | Hammons et al. | |
| 5,876,393 A | 3/1999 | Ahr et al. | |
| 5,887,291 A | 3/1999 | Bellizzi | |
| 5,891,125 A | 4/1999 | Plumley | |
| 5,894,608 A | 4/1999 | Birbara | |
| 5,895,349 A | 4/1999 | Tihon | |
| D409,303 S | 5/1999 | Oepping | |
| 5,911,222 A | 6/1999 | Lawrence et al. | |
| 5,956,782 A | 9/1999 | Olguin | |
| 5,957,904 A | 9/1999 | Holland | |
| 5,968,026 A | 10/1999 | Osborn et al. | |
| 5,972,505 A | 10/1999 | Phillips et al. | |
| 6,007,526 A | 12/1999 | Passalaqua et al. | |
| 6,039,060 A | 3/2000 | Rower | |
| 6,050,983 A | 4/2000 | Moore et al. | |
| 6,059,762 A | 5/2000 | Boyer et al. | |
| 6,063,064 A | 5/2000 | Tuckey et al. | |
| 6,098,625 A | 8/2000 | Winkler | |
| 6,105,174 A | 8/2000 | Karlsten et al. | |
| 6,113,582 A | 9/2000 | Dwork | |
| 6,117,163 A | 9/2000 | Bierman | |
| 6,123,398 A | 9/2000 | Arai et al. | |
| 6,129,718 A | 10/2000 | Wada et al. | |
| 6,131,964 A | 10/2000 | Sareshwala | |

(56)        References Cited

U.S. PATENT DOCUMENTS

| | | | |
|---|---|---|---|
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,220,050 B1 | 4/2001 | Cooksey |
| 6,244,311 B1 | 6/2001 | Hand et al. |
| 6,248,096 B1 | 6/2001 | Dwork et al. |
| 6,263,887 B1 | 7/2001 | Dunn |
| 6,283,246 B1 | 9/2001 | Nishikawa |
| 6,296,627 B1 | 10/2001 | Edwards |
| 6,311,339 B1 | 11/2001 | Kraus |
| 6,316,688 B1 | 11/2001 | Hammons et al. |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,395,956 B1 | 5/2002 | Glasgow et al. |
| 6,398,742 B1 | 6/2002 | Kim |
| 6,406,463 B1 | 6/2002 | Brown |
| 6,409,712 B1 | 6/2002 | Dutari et al. |
| 6,415,888 B2 | 7/2002 | An et al. |
| 6,416,500 B1 | 7/2002 | Wada et al. |
| 6,423,045 B1 | 7/2002 | Wise et al. |
| 6,428,521 B1 * | 8/2002 | Droll ..................... A61F 5/4408 |
| | | 604/329 |
| 6,428,522 B1 | 8/2002 | Dipalma et al. |
| 6,446,454 B1 | 9/2002 | Lee et al. |
| 6,461,340 B1 | 10/2002 | Lenker et al. |
| 6,467,570 B1 | 10/2002 | Herold |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,524,292 B1 | 2/2003 | Dipalma et al. |
| 6,526,603 B1 | 3/2003 | Murphy |
| 6,540,729 B1 | 4/2003 | Wada et al. |
| 6,547,771 B2 | 4/2003 | Robertson et al. |
| 6,551,293 B1 | 4/2003 | Mitchell |
| 6,569,133 B2 | 5/2003 | Cheng et al. |
| D476,518 S | 7/2003 | Doppelt |
| 6,592,560 B2 | 7/2003 | Snyder et al. |
| 6,610,038 B1 | 8/2003 | Dipalma et al. |
| 6,618,868 B2 | 9/2003 | Minnick |
| 6,620,142 B1 | 9/2003 | Flueckiger |
| 6,629,651 B1 | 10/2003 | Male et al. |
| 6,635,037 B1 | 10/2003 | Bennett |
| 6,635,038 B2 | 10/2003 | Scovel |
| 6,652,495 B1 | 11/2003 | Walker |
| 6,666,850 B1 | 12/2003 | Ahr et al. |
| 6,685,684 B1 | 2/2004 | Falconer |
| 6,695,828 B1 | 2/2004 | Dipalma et al. |
| 6,699,174 B1 | 3/2004 | Bennett |
| 6,700,034 B1 | 3/2004 | Lindsay et al. |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,848,719 B2 | 2/2005 | Rowley |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,087,043 B2 | 8/2006 | Dolan |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,166,092 B2 | 1/2007 | Elson et al. |
| 7,171,699 B2 | 2/2007 | Ernest et al. |
| 7,171,871 B2 | 2/2007 | Kozak |
| 7,179,951 B2 | 2/2007 | Krishnaswamy-mirle et al. |
| 7,181,781 B1 * | 2/2007 | Trabold .................. A61F 5/455 |
| | | 4/144.1 |
| 7,186,245 B1 | 3/2007 | Cheng et al. |
| 7,192,424 B2 | 3/2007 | Cooper |
| 7,219,764 B1 | 5/2007 | Forbes |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,549,511 B2 | 6/2009 | Marocco |
| 7,549,512 B2 | 6/2009 | Newberry |
| 7,585,293 B2 | 9/2009 | Vermaak |
| 7,588,560 B1 | 9/2009 | Dunlop |
| 7,637,905 B2 | 12/2009 | Saadat et al. |
| 7,658,730 B2 | 2/2010 | Conley |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| 7,803,144 B1 | 9/2010 | Vollrath |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,981,087 B2 | 7/2011 | Gesler, III |
| 7,993,318 B2 | 8/2011 | Olsson et al. |
| 8,015,627 B2 | 9/2011 | Baker et al. |
| 8,016,071 B1 | 9/2011 | Martinus et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,167,860 B1 | 5/2012 | Siegel |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |

(56) References Cited

U.S. PATENT DOCUMENTS

| | | | |
|---|---|---|---|
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,343,125 B2 | 1/2013 | Kawazoe et al. |
| 8,353,074 B2 | 1/2013 | Krebs |
| 8,353,886 B2 | 1/2013 | Bester et al. |
| D676,241 S | 2/2013 | Merrill |
| 8,388,587 B1 | 3/2013 | Gmuer et al. |
| 8,388,588 B2 | 3/2013 | Wada et al. |
| D679,807 S | 4/2013 | Burgess et al. |
| 8,425,482 B2 | 4/2013 | Khoubnazar |
| 8,434,586 B2 | 5/2013 | Pawelski et al. |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,062 B2 | 10/2013 | Kay |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,740,852 B2 | 6/2014 | Aviles |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 * | 10/2014 | Conway ................. A61F 5/4401 |
| | | 604/346 |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,402,424 B2 | 8/2016 | Roy |
| 9,415,191 B2 | 8/2016 | Aviles |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |
| 9,737,433 B2 | 8/2017 | Joh |
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | Mcgirr et al. |
| D814,239 S | 4/2018 | Arora |
| D817,484 S | 5/2018 | Lafond |
| 9,968,908 B2 | 5/2018 | Ladrech et al. |
| 10,010,393 B1 | 7/2018 | Nguyen et al. |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| 10,258,517 B1 | 4/2019 | Maschino et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,500,108 B1 | 12/2019 | Maschino et al. |
| 10,502,198 B2 | 12/2019 | Stumpf et al. |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| 10,806,623 B2 | 10/2020 | VanMiddendorp et al. |
| 10,806,642 B2 | 10/2020 | Tagomori et al. |
| D901,214 S | 11/2020 | Hu |
| 10,849,799 B2 | 12/2020 | Nishikawa et al. |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| 11,002,165 B2 | 5/2021 | Poulin |
| D923,365 S | 6/2021 | Wang |
| 11,020,567 B2 | 6/2021 | Rule et al. |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,090,183 B2 | 8/2021 | Sanchez et al. |
| 11,160,695 B2 | 11/2021 | Febo et al. |
| 11,160,697 B2 | 11/2021 | Maschino et al. |
| 11,168,420 B2 | 11/2021 | Kinugasa et al. |
| 11,179,506 B2 | 11/2021 | Barr et al. |

(56) References Cited

U.S. PATENT DOCUMENTS

| | | | |
|---|---|---|---|
| 11,199,116 B2 | 12/2021 | Ostromecki et al. | |
| 11,207,206 B2 | 12/2021 | Sharma et al. | |
| 11,226,376 B2 | 1/2022 | Yamauchi et al. | |
| 11,253,389 B2 | 2/2022 | Sharma et al. | |
| 11,253,407 B2 | 2/2022 | Miao et al. | |
| 11,326,586 B2 | 5/2022 | Milner et al. | |
| 11,369,508 B2 | 6/2022 | Ecklund et al. | |
| 11,369,524 B2 | 6/2022 | Hubbard et al. | |
| 11,376,152 B2 | 7/2022 | Sanchez et al. | |
| 11,382,786 B2 | 7/2022 | Sanchez et al. | |
| 11,382,788 B2 | 7/2022 | Hjorth et al. | |
| 11,389,318 B2 | 7/2022 | Radl et al. | |
| 11,395,871 B2 | 7/2022 | Radl et al. | |
| 11,399,990 B2 | 8/2022 | Suyama | |
| 11,426,303 B2 | 8/2022 | Davis et al. | |
| 11,504,265 B2 | 11/2022 | Godinez et al. | |
| 11,529,252 B2 | 12/2022 | Glithero et al. | |
| 11,547,788 B2 | 1/2023 | Radl et al. | |
| 11,806,266 B2 | 11/2023 | Sanchez et al. | |
| 11,813,189 B2 | 11/2023 | Hussey et al. | |
| 11,839,567 B2 | 12/2023 | Davis et al. | |
| D1,010,109 S | 1/2024 | Ecklund et al. | |
| 11,857,716 B2 | 1/2024 | Lee et al. | |
| 11,865,030 B2 | 1/2024 | Davis et al. | |
| 11,890,221 B2 | 2/2024 | Ulreich et al. | |
| 11,911,160 B2 | 2/2024 | Woodard et al. | |
| 11,925,575 B2 | 3/2024 | Newton | |
| 11,938,053 B2 | 3/2024 | Austermann et al. | |
| 11,944,740 B2 | 4/2024 | Hughett et al. | |
| 11,994,122 B2 | 5/2024 | Bodain | |
| 11,998,475 B2 | 6/2024 | Becker et al. | |
| 12,023,457 B2 | 7/2024 | Mann et al. | |
| 12,042,422 B2 | 7/2024 | Davis et al. | |
| D1,038,385 S | 8/2024 | Ecklund et al. | |
| 12,064,372 B2 | 8/2024 | Godinez et al. | |
| 12,070,432 B2 | 8/2024 | Tourchak et al. | |
| 12,090,083 B2 | 9/2024 | Ecklund et al. | |
| 12,121,468 B2 | 10/2024 | Sanchez et al. | |
| 12,133,813 B2 | 11/2024 | Ulreich et al. | |
| 12,138,195 B2 | 11/2024 | Alder et al. | |
| 12,186,229 B2 | 1/2025 | Davis et al. | |
| 12,193,962 B2 | 1/2025 | Newton et al. | |
| 12,245,966 B2 | 3/2025 | Newton | |
| 12,274,638 B2 | 4/2025 | Spector | |
| 12,350,190 B2 | 7/2025 | Hughett, Sr. et al. | |
| 2001/0037097 A1 | 11/2001 | Cheng et al. | |
| 2001/0037098 A1 | 11/2001 | Snyder | |
| 2001/0054426 A1 | 12/2001 | Knudson et al. | |
| 2002/0019614 A1 | 2/2002 | Woon | |
| 2002/0026161 A1 | 2/2002 | Grundke | |
| 2002/0026163 A1 | 2/2002 | Grundke | |
| 2002/0042945 A1 | 4/2002 | Sands | |
| 2002/0087131 A1 | 7/2002 | Wolff et al. | |
| 2002/0091364 A1 | 7/2002 | Prabhakar | |
| 2002/0189992 A1 | 12/2002 | Schmidt et al. | |
| 2002/0193760 A1 | 12/2002 | Thompson | |
| 2002/0193762 A1 | 12/2002 | Suydam | |
| 2003/0004436 A1 | 1/2003 | Schmidt et al. | |
| 2003/0032931 A1 | 2/2003 | Grundke et al. | |
| 2003/0032944 A1 | 2/2003 | Cawood | |
| 2003/0073964 A1 | 4/2003 | Palumbo et al. | |
| 2003/0074724 A1 | 4/2003 | Sands | |
| 2003/0120178 A1 | 6/2003 | Heki | |
| 2003/0129178 A1 | 7/2003 | Wegman et al. | |
| 2003/0157859 A1 | 8/2003 | Ishikawa | |
| 2003/0181880 A1 | 9/2003 | Schwartz | |
| 2003/0195484 A1 | 10/2003 | Harvie | |
| 2003/0204173 A1 | 10/2003 | Burns et al. | |
| 2003/0233079 A1 | 12/2003 | Parks et al. | |
| 2004/0006321 A1 | 1/2004 | Cheng et al. | |
| 2004/0015141 A1 | 1/2004 | Cheng et al. | |
| 2004/0056122 A1 | 3/2004 | Male et al. | |
| 2004/0084465 A1 | 5/2004 | Luburic | |
| 2004/0127872 A1 | 7/2004 | Petryk et al. | |
| 2004/0128749 A1 | 7/2004 | Scott | |
| 2004/0143229 A1 | 7/2004 | Easter | |
| 2004/0147863 A1 | 7/2004 | Diaz et al. | |
| 2004/0147894 A1 | 7/2004 | Mizutani et al. | |
| 2004/0147895 A1 | 7/2004 | Mizutani et al. | |
| 2004/0158221 A1 | 8/2004 | Mizutani et al. | |
| 2004/0176731 A1 | 9/2004 | Cheng et al. | |
| 2004/0176746 A1 | 9/2004 | Forral | |
| 2004/0181201 A1 | 9/2004 | Mizutani et al. | |
| 2004/0187200 A1 | 9/2004 | Otto et al. | |
| 2004/0191919 A1 | 9/2004 | Unger et al. | |
| 2004/0194792 A1 | 10/2004 | Zhuang et al. | |
| 2004/0200936 A1 | 10/2004 | Opperthauser | |
| 2004/0207530 A1 | 10/2004 | Nielsen | |
| 2004/0236292 A1 | 11/2004 | Tazoe et al. | |
| 2004/0243075 A1 | 12/2004 | Harvie | |
| 2004/0254547 A1 | 12/2004 | Okabe et al. | |
| 2005/0010182 A1 | 1/2005 | Parks et al. | |
| 2005/0010197 A1 | 1/2005 | Lau et al. | |
| 2005/0033248 A1 | 2/2005 | Machida et al. | |
| 2005/0065471 A1 | 3/2005 | Kuntz | |
| 2005/0070861 A1 | 3/2005 | Okabe et al. | |
| 2005/0070862 A1 | 3/2005 | Tazoe et al. | |
| 2005/0082300 A1 | 4/2005 | Modrell et al. | |
| 2005/0097662 A1 | 5/2005 | Leimkuhler et al. | |
| 2005/0101924 A1 | 5/2005 | Elson et al. | |
| 2005/0119630 A1 | 6/2005 | Harvie | |
| 2005/0131361 A1 | 6/2005 | Miskie | |
| 2005/0137557 A1 | 6/2005 | Swiecicki et al. | |
| 2005/0137560 A1 | 6/2005 | Mizutani et al. | |
| 2005/0137561 A1 | 6/2005 | Mizutani et al. | |
| 2005/0148984 A1 | 7/2005 | Lindsay et al. | |
| 2005/0154360 A1 | 7/2005 | Harvie | |
| 2005/0177070 A1 | 8/2005 | Levinson | |
| 2005/0197639 A1 | 9/2005 | Mombrinie | |
| 2005/0197645 A1 | 9/2005 | Karpowicz et al. | |
| 2005/0215969 A1 | 9/2005 | Mizutani et al. | |
| 2005/0273069 A1 | 12/2005 | Mizutani et al. | |
| 2005/0273920 A1 | 12/2005 | Marinas | |
| 2005/0277903 A1 | 12/2005 | Mizutani et al. | |
| 2005/0277904 A1 | 12/2005 | Chase et al. | |
| 2005/0279359 A1 | 12/2005 | LeBlanc et al. | |
| 2006/0004332 A1 | 1/2006 | Marx | |
| 2006/0005307 A1 | 1/2006 | Arguelles | |
| 2006/0015080 A1 | 1/2006 | Mahnensmith | |
| 2006/0015081 A1 | 1/2006 | Suzuki et al. | |
| 2006/0016778 A1 | 1/2006 | Park | |
| 2006/0069359 A1 | 3/2006 | Dipalma et al. | |
| 2006/0079854 A1 | 4/2006 | Kay et al. | |
| 2006/0111648 A1 | 5/2006 | Vermaak | |
| 2006/0113334 A1 | 6/2006 | Mikhail et al. | |
| 2006/0155214 A1 | 7/2006 | Wightman | |
| 2006/0166350 A1 | 7/2006 | Lowe et al. | |
| 2006/0171997 A1 | 8/2006 | Gruenbacher et al. | |
| 2006/0180566 A1 | 8/2006 | Mataya | |
| 2006/0200102 A1 | 9/2006 | Cooper | |
| 2006/0229575 A1 | 10/2006 | Boiarski | |
| 2006/0229576 A1 | 10/2006 | Conway et al. | |
| 2006/0231648 A1 | 10/2006 | Male et al. | |
| 2006/0235266 A1 | 10/2006 | Nan | |
| 2006/0235359 A1 | 10/2006 | Marland | |
| 2006/0241553 A1 | 10/2006 | Harvie | |
| 2006/0269439 A1 | 11/2006 | White | |
| 2006/0277670 A1 | 12/2006 | Baker et al. | |
| 2007/0006368 A1 | 1/2007 | Key | |
| 2007/0010797 A1 | 1/2007 | Nishtala et al. | |
| 2007/0016152 A1 | 1/2007 | Karpowicz et al. | |
| 2007/0025886 A1 | 2/2007 | Yong | |
| 2007/0038194 A1 | 2/2007 | Wada et al. | |
| 2007/0055209 A1 | 3/2007 | Patel et al. | |
| 2007/0073252 A1 | 3/2007 | Forgrave | |
| 2007/0117880 A1 | 5/2007 | Elson et al. | |
| 2007/0118993 A1 | 5/2007 | Bates | |
| 2007/0135786 A1 | 6/2007 | Schmidt et al. | |
| 2007/0137718 A1 | 6/2007 | Rushlander et al. | |
| 2007/0149935 A1 | 6/2007 | Dirico | |
| 2007/0191804 A1 | 8/2007 | Coley | |
| 2007/0203464 A1 | 8/2007 | Green et al. | |
| 2007/0214553 A1 | 9/2007 | Carromba et al. | |
| 2007/0225663 A1 | 9/2007 | Watt et al. | |

(56) References Cited

U.S. PATENT DOCUMENTS

| | | |
|---|---|---|
| 2007/0225666 A1 | 9/2007 | Otto |
| 2007/0225668 A1 | 9/2007 | Otto |
| 2007/0266486 A1 | 11/2007 | Ramirez |
| 2007/0270716 A1 | 11/2007 | Wu et al. |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0077099 A1 | 3/2008 | House |
| 2008/0091153 A1 | 4/2008 | Harvie |
| 2008/0091158 A1 | 4/2008 | Yang |
| 2008/0114327 A1 | 5/2008 | Barge |
| 2008/0140033 A1 | 6/2008 | Burgess et al. |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1* | 11/2008 | Van Den Heuvel .... A61F 5/455 |
| | | 604/327 |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0226541 A1 | 9/2009 | Scholz et al. |
| 2009/0234312 A1 | 9/2009 | Otoole et al. |
| 2009/0251510 A1 | 10/2009 | Noro et al. |
| 2009/0254040 A1 | 10/2009 | Bierman et al. |
| 2009/0259206 A1 | 10/2009 | Kai et al. |
| 2009/0264840 A1 | 10/2009 | Virginio |
| 2009/0270822 A1 | 10/2009 | Medeiros |
| 2009/0281510 A1 | 11/2009 | Fisher |
| 2009/0283982 A1 | 11/2009 | Thomas |
| 2009/0306610 A1 | 12/2009 | Van Den Heuvel et al. |
| 2010/0004612 A1 | 1/2010 | Thevenin |
| 2010/0030189 A1 | 2/2010 | Fleming |
| 2010/0031429 A1 | 2/2010 | Kim et al. |
| 2010/0032789 A1 | 2/2010 | Schoen et al. |
| 2010/0058660 A1 | 3/2010 | Williams |
| 2010/0121289 A1 | 5/2010 | Parks et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0198904 A1 | 8/2011 | Thomas et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0116336 A1 | 5/2012 | Sharma et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0209216 A1 | 8/2012 | Jensen et al. |
| 2012/0209225 A1 | 8/2012 | Hu et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0019374 A1 | 1/2013 | Schwartz |
| 2013/0036544 A1 | 2/2013 | Lee et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0144240 A1 | 6/2013 | Ellis |
| 2013/0150813 A1 | 6/2013 | Gordon et al. |
| 2013/0158494 A1 | 6/2013 | Ong et al. |
| 2013/0165880 A1 | 6/2013 | Amos et al. |
| 2013/0218112 A1 | 8/2013 | Thompson |
| 2013/0245496 A1 | 9/2013 | Wells et al. |
| 2013/0245586 A1 | 9/2013 | Jha |
| 2013/0274711 A1 | 10/2013 | O'Day |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0039440 A1 | 2/2014 | Doescher |
| 2014/0058347 A1 | 2/2014 | Marquette |
| 2014/0107599 A1 | 4/2014 | Fink et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0257231 A1 | 9/2014 | Wang et al. |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209188 A1 | 7/2015 | Scheremet et al. |
| 2015/0209194 A1 | 7/2015 | Heyman |
| 2015/0267862 A1 | 9/2015 | Mishler |
| 2015/0290421 A1 | 10/2015 | Glickman et al. |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0359996 A1 | 12/2015 | Arora et al. |
| 2015/0366699 A1 | 12/2015 | Nelson |

(56)           References Cited

U.S. PATENT DOCUMENTS

| | | |
|---|---|---|
| 2016/0008193 A1 | 1/2016 | Schulke |
| 2016/0029998 A1 | 2/2016 | Brister et al. |
| 2016/0030228 A1 | 2/2016 | Jones |
| 2016/0038356 A1 | 2/2016 | Yao et al. |
| 2016/0051395 A1 | 2/2016 | Ugarte |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0135792 A1 | 5/2016 | Cai |
| 2016/0136338 A1 | 5/2016 | Lee et al. |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0327553 A1 | 11/2016 | Edwards et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0042724 A1 | 2/2017 | Ugarte |
| 2017/0042748 A1 | 2/2017 | Griffin |
| 2017/0100276 A1 | 4/2017 | Joh |
| 2017/0107312 A1 | 4/2017 | Hinayama et al. |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0238911 A1 | 8/2017 | Duval |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1* | 9/2017 | Sanchez ................. A61F 5/443 |
| 2017/0266658 A1 | 9/2017 | Bruno et al. |
| 2017/0281399 A1 | 10/2017 | Vanmiddendorp et al. |
| 2017/0281419 A1 | 10/2017 | Pintado |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0149635 A1 | 5/2018 | Abir |
| 2018/0193215 A1 | 7/2018 | Davies et al. |
| 2018/0200101 A1 | 7/2018 | Su |
| 2018/0214297 A1 | 8/2018 | Hughett et al. |
| 2018/0221216 A1 | 8/2018 | Benz et al. |
| 2018/0228642 A1* | 8/2018 | Davis ..................... A61F 5/451 |
| 2018/0229014 A1 | 8/2018 | Guirguis et al. |
| 2018/0256384 A1 | 9/2018 | Kasirye |
| 2018/0271694 A1 | 9/2018 | Fernandez et al. |
| 2018/0280236 A1 | 10/2018 | Ludin et al. |
| 2018/0317892 A1 | 11/2018 | Catlin |
| 2018/0325748 A1 | 11/2018 | Sharma et al. |
| 2019/0001029 A1 | 1/2019 | Davie et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133126 A1 | 5/2019 | Modak et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0226189 A1 | 7/2019 | Braxton |
| 2019/0240079 A1 | 8/2019 | Tuli |
| 2019/0247222 A1 | 8/2019 | Ecklund et al. |
| 2019/0247223 A1 | 8/2019 | Brun et al. |
| 2019/0247623 A1 | 8/2019 | Helm et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365303 A1 | 12/2019 | Bullington et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0040561 A1 | 2/2020 | Sugawara |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0179177 A1 | 6/2020 | Erdem et al. |
| 2020/0187918 A1 | 6/2020 | Wiygul |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0384242 A1 | 12/2020 | Havard et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0398024 A1 | 12/2020 | Fletter et al. |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |

(56) References Cited

U.S. PATENT DOCUMENTS

| | | |
|---|---|---|
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0186744 A1 | 6/2021 | Spector |
| 2021/0211568 A1 | 7/2021 | Zhou et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0290464 A1 | 9/2021 | Furuta |
| 2021/0315726 A1 | 10/2021 | Lin |
| 2021/0315727 A1 | 10/2021 | Jiang |
| 2021/0353449 A1 | 11/2021 | Sharma et al. |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0026546 A1 | 1/2022 | Aono et al. |
| 2022/0031290 A1* | 2/2022 | Weed .................. A61B 10/007 |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062025 A1 | 3/2022 | Shields et al. |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0118165 A1 | 4/2022 | Knapp et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0280710 A1 | 9/2022 | Agrawal et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339023 A1 | 10/2022 | Davis et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0387693 A1 | 12/2022 | Bannwart et al. |
| 2022/0395390 A1 | 12/2022 | Brooks |
| 2022/0395391 A1 | 12/2022 | Saunders et al. |
| 2022/0401252 A1 | 12/2022 | Warren |
| 2022/0409419 A1 | 12/2022 | Garvey et al. |
| 2022/0409422 A1 | 12/2022 | Schneider et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0049924 A1 | 2/2023 | Johannes et al. |
| 2023/0052238 A1 | 2/2023 | Oluwasogo |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0091118 A1 | 3/2023 | Watson |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1 | 5/2023 | Abdelal et al. |
| 2023/0145365 A1 | 5/2023 | Martin et al. |
| 2023/0155253 A1 | 5/2023 | Yin et al. |
| 2023/0190511 A1 | 6/2023 | Sharma et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277360 A1 | 9/2023 | Lambert et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0389900 A1 | 12/2023 | Xie et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0033148 A1 | 2/2024 | Gordon et al. |
| 2024/0041638 A1 | 2/2024 | Johannes et al. |
| 2024/0058157 A1 | 2/2024 | Davis |
| 2024/0058160 A1 | 2/2024 | Young Joyner et al. |
| 2024/0058161 A1 | 2/2024 | Ulreich et al. |
| 2024/0058520 A1 | 2/2024 | Yin et al. |
| 2024/0065881 A1 | 2/2024 | Kuroda et al. |
| 2024/0082044 A1 | 3/2024 | Nguyen et al. |
| 2024/0099874 A1 | 3/2024 | Sanchez et al. |
| 2024/0108268 A1 | 4/2024 | Woodard et al. |
| 2024/0110318 A1 | 4/2024 | Bendt et al. |
| 2024/0122773 A1 | 4/2024 | Nguyen et al. |
| 2024/0123134 A1 | 4/2024 | Kharkar et al. |
| 2024/0130885 A1 | 4/2024 | Young Joyner et al. |
| 2024/0148539 A1 | 5/2024 | Austermann et al. |
| 2024/0156633 A1 | 5/2024 | Fallows et al. |
| 2024/0164935 A1 | 5/2024 | Newton |
| 2024/0252343 A1 | 8/2024 | Voda |

(56) References Cited

U.S. PATENT DOCUMENTS

| | | |
|---|---|---|
| 2024/0261131 A1 | 8/2024 | Garvey et al. |
| 2024/0268986 A1 | 8/2024 | Barnes et al. |
| 2024/0268989 A1 | 8/2024 | Martin et al. |
| 2024/0268991 A1 | 8/2024 | Davis |
| 2024/0269027 A1 | 8/2024 | Tourchak et al. |
| 2024/0285425 A1 | 8/2024 | Donohoe et al. |
| 2024/0325190 A1 | 10/2024 | Minchew et al. |
| 2024/0358539 A1 | 10/2024 | Gallup |
| 2024/0358542 A1 | 10/2024 | Richardson et al. |
| 2024/0374414 A1 | 11/2024 | Richardson et al. |
| 2025/0009552 A1 | 1/2025 | Blabas et al. |
| 2025/0073055 A1 | 3/2025 | Ecklund et al. |
| 2025/0107920 A1 | 4/2025 | Fallows et al. |
| 2025/0107921 A1 | 4/2025 | Sanchez et al. |

FOREIGN PATENT DOCUMENTS

| | | |
|---|---|---|
| AU | 2022349367 A1 | 4/2024 |
| CA | 2269203 Y | 12/1997 |
| CA | 2165286 C | 9/1999 |
| CA | 2335223 A1 | 1/2000 |
| CA | 2354132 A1 | 6/2000 |
| CA | 2359091 C | 9/2003 |
| CA | 1720888 A | 1/2006 |
| CA | 2488867 C | 8/2007 |
| CA | 101262836 A | 9/2008 |
| CA | 103717180 A | 4/2014 |
| CA | 3031934 A1 | 2/2018 |
| CA | 107847384 A | 3/2018 |
| CA | 3050918 A1 | 8/2018 |
| CA | 3098571 A1 | 11/2019 |
| CA | 3144181 A1 | 1/2021 |
| CA | 3188651 A1 | 7/2023 |
| CN | 1332620 A | 1/2002 |
| CN | 1434693 A | 8/2003 |
| CN | 1533755 A | 10/2004 |
| CN | 1579348 A | 2/2005 |
| CN | 1602825 A | 4/2005 |
| CN | 1638708 A | 7/2005 |
| CN | 2936204 Y | 8/2007 |
| CN | 101522148 A | 9/2009 |
| CN | 102159159 A | 8/2011 |
| CN | 202184840 U | 4/2012 |
| CN | 102481441 A | 5/2012 |
| CN | 202463712 U | 10/2012 |
| CN | 202950810 U | 5/2013 |
| CN | 103533968 A | 1/2014 |
| CN | 204562697 U | 8/2015 |
| CN | 105411783 A | 3/2016 |
| CN | 105451693 A | 3/2016 |
| CN | 105534632 A | 5/2016 |
| CN | 106132360 A | 11/2016 |
| CN | 205849719 U | 1/2017 |
| CN | 205924282 U | 2/2017 |
| CN | 106726089 A | 5/2017 |
| CN | 107920912 A | 4/2018 |
| CN | 108420590 A | 8/2018 |
| CN | 209285902 U | 8/2019 |
| CN | 110381883 A | 10/2019 |
| CN | 211198839 U | 8/2020 |
| CN | 111991136 A | 11/2020 |
| CN | 112022488 A | 12/2020 |
| CN | 212234893 U | 12/2020 |
| CN | 212466312 U | 2/2021 |
| CN | 112566550 A | 3/2021 |
| CN | 112603184 A | 4/2021 |
| CN | 213490035 U | 6/2021 |
| CN | 114007493 A | 2/2022 |
| CN | 114375187 A | 4/2022 |
| CN | 116096332 A | 5/2023 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 4416094 A1 | 11/1995 |
| DE | 4236097 C2 | 10/1996 |
| DE | 19619597 A1 | 11/1997 |
| DE | 102005037762 B3 | 9/2006 |
| DE | 102011103783 A1 | 12/2012 |
| DE | 102012112818 A1 | 6/2014 |
| DE | 202015104597 U1 | 7/2016 |
| DE | 102018118570 A1 | 2/2020 |
| DE | 102020121462 B3 | 1/2022 |
| DK | 9600118 | 11/1996 |
| EP | 0032138 A2 | 7/1981 |
| EP | 0066070 B1 | 12/1982 |
| EP | 0068712 A1 | 1/1983 |
| EP | 0140470 A1 | 5/1985 |
| EP | 0220962 A1 | 5/1987 |
| EP | 0140471 B1 | 5/1988 |
| EP | 0274753 A2 | 7/1988 |
| EP | 0119143 B1 | 11/1988 |
| EP | 0483592 A1 | 5/1992 |
| EP | 0483730 A1 | 5/1992 |
| EP | 0610638 A1 | 8/1994 |
| EP | 0613355 A1 | 9/1994 |
| EP | 0711536 A1 | 5/1996 |
| EP | 0613355 B1 | 1/1997 |
| EP | 0680296 B1 | 5/1997 |
| EP | 0787472 A1 | 8/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1658831 B1 | 1/2008 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2470251 B1 | 12/2014 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3753492 A1 | 12/2020 |
| EP | 3777801 A1 | 2/2021 |
| EP | 3788992 A1 | 3/2021 |
| EP | 3576689 B1 | 3/2022 |
| EP | 3752110 B1 | 3/2022 |
| EP | 3787570 B1 | 3/2022 |
| EP | 4025163 A1 | 7/2022 |
| EP | 3463180 B1 | 3/2023 |
| EP | 3749230 B1 | 3/2023 |
| EP | 3569205 B1 | 6/2023 |
| EP | 4192402 A1 | 6/2023 |
| EP | 4218702 A1 | 8/2023 |
| EP | 3624742 B1 | 1/2024 |
| EP | 4382082 A2 | 6/2024 |
| EP | 4445881 A2 | 10/2024 |
| EP | 4464288 A2 | 11/2024 |
| EP | 4215134 B1 | 1/2025 |
| EP | 4494611 A2 | 1/2025 |
| EP | 4527361 A2 | 3/2025 |
| FR | 2826704 A1 | 1/2003 |
| GB | 871820 A | 7/1961 |
| GB | 873045 A | 7/1961 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2181953 A | 5/1987 |
| GB | 2148126 B | 7/1987 |
| GB | 2191095 A | 12/1987 |

(56)     References Cited

FOREIGN PATENT DOCUMENTS

| | | | |
|---|---|---|---|
| GB | 2199750 | A | 7/1988 |
| GB | 2260907 | A | 5/1993 |
| GB | 2415386 | A | 12/2005 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58188016 | U | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H0515928 | U | 3/1993 |
| JP | H05123349 | A | 5/1993 |
| JP | H05123350 | A | 5/1993 |
| JP | H0626264 | U | 4/1994 |
| JP | 3087938 | B2 | 10/1995 |
| JP | H085630 | A | 1/1996 |
| JP | H08117271 | A | 5/1996 |
| JP | 2686634 | B2 | 12/1997 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2002502667 | A | 1/2002 |
| JP | 2002102285 | A | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | A | 8/2003 |
| JP | 2003528691 | A | 9/2003 |
| JP | 2004057578 | A | 2/2004 |
| JP | 2004130056 | A | 4/2004 |
| JP | 2004267400 | A | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136491 | A | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011522584 | A | 8/2011 |
| JP | 2011202664 | A | 10/2011 |
| JP | 2011218130 | A | 11/2011 |
| JP | 2011224070 | A | 11/2011 |
| JP | 3175719 | U | 4/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 3208707 | U | 2/2017 |
| JP | 3209321 | U | 3/2017 |
| JP | 2017070400 | A | 4/2017 |
| JP | 2017512603 | A | 5/2017 |
| JP | 2017127596 | A | 7/2017 |
| JP | 2017201272 | A | 11/2017 |
| JP | 2019010375 | A | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020510464 | A | 4/2020 |
| JP | 2020520775 | A | 7/2020 |
| JP | 2020124425 | A | 8/2020 |
| JP | 2021007472 | A | 1/2021 |
| JP | 2021041145 | A | 3/2021 |
| JP | 2021074491 | A | 5/2021 |
| JP | 2021120686 | A | 8/2021 |
| JP | 2021520952 | A | 8/2021 |
| JP | 2021522009 | A | 8/2021 |
| JP | 2021522013 | A | 8/2021 |
| JP | 2021522019 | A | 8/2021 |
| JP | 7129493 | B2 | 8/2022 |
| JP | 2022554252 | A | 12/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090072069 | A | 7/2009 |
| KR | 20090104426 | A | 10/2009 |
| KR | 20090110359 | A | 10/2009 |
| KR | 20120005922 | A | 1/2012 |
| KR | 20140039485 | A | 4/2014 |
| KR | 101432639 | B1 | 8/2014 |
| KR | 20180106659 | A | 10/2018 |
| KR | 20180108774 | A | 10/2018 |
| KR | 20230034343 | A | 3/2023 |
| PT | 2068717 | E | 6/2013 |
| SE | 505542 | C2 | 9/1997 |
| TW | 408207 | B | 10/2000 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |

(56)        References Cited

FOREIGN PATENT DOCUMENTS

| | | | |
|---|---|---|---|
| WO | 9309736 | A3 | 6/1993 |
| WO | 9416914 | A1 | 8/1994 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03015671 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005051252 | A1 | 6/2005 |
| WO | 2005060558 | A2 | 7/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017075226 | A1 | 5/2017 |
| WO | 2017100511 | A1 | 6/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018235026 | A1 | 12/2018 |
| WO | 2018235065 | A1 | 12/2018 |
| WO | 2019004404 | A1 | 1/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |

(56) References Cited

FOREIGN PATENT DOCUMENTS

| | | | |
|---|---|---|---|
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023018656 | A1 | 2/2023 |
| WO | 2023018657 | A1 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049156 | A1 | 3/2023 |
| WO | 2023049175 | A1 | 3/2023 |
| WO | 2023086394 | A1 | 5/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023163725 | A1 | 8/2023 |
| WO | 2023191764 | A1 | 10/2023 |
| WO | 2023244238 | A1 | 12/2023 |
| WO | 2024043871 | A1 | 2/2024 |
| WO | 2024058788 | A1 | 3/2024 |
| WO | 2024253655 | A1 | 12/2024 |
| WO | 2025034959 | A1 | 2/2025 |
| WO | 2025038087 | A1 | 2/2025 |
| WO | 2025038088 | A1 | 2/2025 |
| WO | 2025048789 | A1 | 3/2025 |
| WO | 2025071622 | A1 | 4/2025 |
| WO | 2025179267 | A1 | 8/2025 |

OTHER PUBLICATIONS

Advisory Action for U.S. Appl. No. 16/245,726 mailed Apr. 19, 2023.

Advisory Action for U.S. Appl. No. 16/369,676 mailed Mar. 24, 2023.

Advisory Action for U.S. Appl. No. 16/433,773 mailed Dec. 29, 2023.

Advisory Action for U.S. Appl. No. 16/433,773 mailed Feb. 15, 2023.

Action for U.S. Appl. No. 16/452,258 mailed Oct. 26, 2022.

Advisory Action for U.S. Appl. No. 16/478,180 mailed Sep. 21, 2022.

Advisory Action for U.S. Appl. No. 16/478,180 mailed Sep. 7, 2023.

Advisory Action for U.S. Appl. No. 16/904,868 mailed Jan. 2, 2024.

Advisory Action for U.S. Appl. No. 16/904,868 mailed Jun. 15, 2022.

Advisory Action for U.S. Appl. No. 16/905,400 mailed Feb. 16, 2022.

Advisory Action for U.S. Appl. No. 17/051,550 mailed Sep. 8, 2023.

Advisory Action for U.S. Appl. No. 17/051,585 mailed Oct. 17, 2023.

Advisory Action for U.S. Appl. No. 17/179,116 mailed Jan. 8, 2024.

Advisory Action for U.S. Appl. No. 17/444,792 mailed Aug. 25, 2023.

Advisory Action for U.S. Appl. No. 17/446,256 mailed Dec. 8, 2023.

Advisory Action for U.S. Appl. No. 17/448,811 mailed Nov. 15, 2023.

Advisory Action for U.S. Appl. No. 17/451,345 mailed Oct. 20, 2023.

Advisory Action for U.S. Appl. No. 17/453,260 mailed Dec. 22, 2023.

Advisory Action for U.S. Appl. No. 17/653,137 mailed Dec. 1, 2023.

Advisory Action for U.S. Appl. No. 17/655,464 mailed Dec. 13, 2023.

(56) References Cited

OTHER PUBLICATIONS

Advisory Action for U.S. Appl. No. 17/662,700 mailed Jan. 30, 2023.

Communication of Notice of Opposition of European Application No. 17807547.9 mailed Jan. 5, 2024.

Corrected Notice of Allowability for U.S. Appl. No. 16/369,676 mailed Dec. 7, 2023.

Corrected Notice of Allowability for U.S. Appl. No. 17/330,657 mailed Dec. 9, 2021.

Final Office Action for U.S. Appl. No. 16/245,726 mailed Nov. 25, 2022.

Final Office Action for U.S. Appl. No. 16/369,676 mailed Aug. 31, 2023.

Final Office Action for U.S. Appl. No. 16/369,676 mailed Dec. 5, 2022.

Final Office Action for U.S. Appl. No. 16/433,773 mailed Oct. 10, 2023.

Final Office Action for U.S. Appl. No. 16/433,773 mailed Oct. 25, 2022.

Final Office Action for U.S. Appl. No. 16/449,039 mailed Aug. 1, 2022.

Final Office Action for U.S. Appl. No. 16/449,039 mailed Nov. 21, 2023.

Final Office Action for U.S. Appl. No. 16/452,145 mailed Mar. 25, 2022.

Final Office Action for U.S. Appl. No. 16/452,258 mailed Dec. 21, 2023.

Final Office Action for U.S. Appl. No. 16/452,258 mailed Jun. 14, 2022.

Final Office Action for U.S. Appl. No. 16/478,180 mailed Jun. 22, 2022.

Final Office Action for U.S. Appl. No. 16/478,180 mailed May 31, 2023.

Final Office Action for U.S. Appl. No. 16/904,868 mailed Mar. 10, 2022.

Final Office Action for U.S. Appl. No. 16/904,868 mailed Nov. 2, 2023.

Final Office Action for U.S. Appl. No. 16/905,400 mailed Dec. 9, 2021.

Final Office Action for U.S. Appl. No. 17/051,399 mailed Jan. 8, 2024.

Final Office Action for U.S. Appl. No. 17/051,399 mailed Mar. 9, 2023.

Final Office Action for U.S. Appl. No. 17/051,550 mailed May 23, 2023.

Final Office Action for U.S. Appl. No. 17/051,585 mailed Jul. 27, 2023.

Final Office Action for U.S. Appl. No. 17/179,116 mailed Oct. 31, 2023.

Final Office Action for U.S. Appl. No. 17/444,792 mailed Jun. 15, 2023.

Final Office Action for U.S. Appl. No. 17/446,256 mailed Sep. 19, 2023.

Final Office Action for U.S. Appl. No. 17/448,811 mailed Aug. 3, 2023.

Final Office Action for U.S. Appl. No. 17/450,864 mailed Dec. 28, 2023.

Final Office Action for U.S. Appl. No. 17/451,345 mailed May 3, 2023.

Final Office Action for U.S. Appl. No. 17/451,354 mailed Oct. 30, 2023.

Final Office Action for U.S. Appl. No. 17/453,260 mailed Oct. 5, 2023.

Final Office Action for U.S. Appl. No. 17/501,591 mailed Nov. 14, 2023.

Final Office Action for U.S. Appl. No. 17/646,771 mailed Dec. 21, 2023.

Final Office Action for U.S. Appl. No. 17/653,137 mailed Sep. 21, 2023.

Final Office Action for U.S. Appl. No. 17/655,464 mailed Sep. 1, 2023.

Final Office Action for U.S. Appl. No. 17/661,090 mailed Dec. 11, 2023.

Final Office Action for U.S. Appl. No. 17/662,700 mailed Sep. 30, 2022.

Final Office Action for U.S. Appl. No. 17/663,330 mailed Dec. 12, 2023.

Final Office Action for U.S. Appl. No. 17/664,487 mailed Jan. 4, 2024.

Final Office Action for U.S. Appl. No. 18/139,523 mailed Dec. 22, 2023.

Final Office Action for U.S. Appl. No. 18/164,800 mailed Dec. 6, 2023.

International Search Report and Written Opinion from International Application No. PCT/IB2021/057173 mailed Nov. 5, 2021.

International Search Report and Written Opinion from International Application No. PCT/US2020/057562 mailed Jan. 27, 2021.

International Search Report and Written Opinion from International Application No. PCT/US2021/015024 mailed May 18, 2021.

International Search Report and Written Opinion from International Application No. PCT/US2021/024162 mailed Jul. 8, 2021.

International Search Report and Written Opinion from International Application No. PCT/US2021/026607 mailed Jul. 29, 2021.

International Search Report and Written Opinion from International Application No. PCT/US2021/027061 mailed Jul. 19, 2021.

International Search Report and Written Opinion from International Application No. PCT/US2021/027104 mailed Jul. 6, 2021.

International Search Report and Written Opinion from International Application No. PCT/US2021/027314 mailed Jul. 6, 2021.

International Search Report and Written Opinion from International Application No. PCT/US2021/027422 mailed Aug. 12, 2021.

International Search Report and Written Opinion from International Application No. PCT/US2021/027425 mailed Aug. 11, 2021.

International Search Report and Written Opinion from International Application No. PCT/US2021/027913 mailed Jul. 12, 2021.

International Search Report and Written Opinion from International Application No. PCT/US2021/027917 mailed Aug. 19, 2021.

International Search Report and Written Opinion from International Application No. PCT/US2021/039866 mailed Oct. 7, 2021.

International Search Report and Written Opinion from International Application No. PCT/US2021/043893 mailed Nov. 22, 2021.

International Search Report and Written Opinion from International Application No. PCT/US2021/044699 mailed Nov. 22, 2021.

International Search Report and Written Opinion from International Application No. PCT/US2021/045188 mailed Jan. 26, 2022.

International Search Report and Written Opinion from International Application No. PCT/US2021/047536 mailed Dec. 23, 2021.

International Search Report and Written Opinion from International Application No. PCT/US2021/048211 mailed Dec. 22, 2021.

International Search Report and Written Opinion from International Application No. PCT/US2021/048661 mailed Feb. 14, 2022.

International Search Report and Written Opinion from International Application No. PCT/US2021/049404 mailed Jan. 18, 2022.

International Search Report and Written Opinion from International Application No. PCT/US2021/051456 mailed Jan. 19, 2022.

International Search Report and Written Opinion from International Application No. PCT/US2021/053593 mailed Apr. 11, 2022.

International Search Report and Written Opinion from International Application No. PCT/US2021/055515 mailed Jan. 28, 2022.

International Search Report and Written Opinion from International Application No. PCT/US2021/056566 mailed Feb. 11, 2022.

International Search Report and Written Opinion from International Application No. PCT/US2021/060993 mailed Mar. 18, 2022.

International Search Report and Written Opinion from International Application No. PCT/US2021/062440 mailed Mar. 28, 2022.

International Search Report and Written Opinion from International Application No. PCT/US2022/011108 mailed Apr. 22, 2022.

International Search Report and Written Opinion from International Application No. PCT/US2022/011281 mailed Apr. 25, 2022.

International Search Report and Written Opinion from International Application No. PCT/US2022/011419 mailed Jun. 7, 2022.

(56) References Cited

OTHER PUBLICATIONS

International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.

International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
Issue Notification for U.S. Appl. No. 14/952,591 mailed Jul. 28, 2021.
Issue Notification for U.S. Appl. No. 16/245,726 mailed Oct. 18, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 17/461,036 mailed Oct. 11, 2023.
Issue Notification for U.S. Appl. No. 17/663,046 mailed Dec. 20, 2023.
Issue Notification for U.S. Appl. No. 29/624,661 mailed Aug. 4, 2021.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 11, 2023.
Non-Final Office Action for U.S. Appl. No. 16/433,773 mailed Apr. 21, 2022.
Non-Final Office Action for U.S. Appl. No. 16/449,039 mailed Apr. 27, 2023.
Non-Final Office Action for U.S. Appl. No. 16/449,039 mailed Dec. 8, 2021.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,145 mailed Sep. 28, 2021.
Non-Final Office Action for U.S. Appl. No. 16/452,258 mailed Apr. 26, 2023.
Non-Final Office Action for U.S. Appl. No. 16/452,258 mailed Sep. 28, 2021.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/478,180 mailed Oct. 22, 2021.
Non-Final Office Action for U.S. Appl. No. 16/899,956 mailed Sep. 2, 2021.
Non-Final Office Action for U.S. Appl. No. 16/904,868 mailed Mar. 15, 2023.
Non-Final Office Action for U.S. Appl. No. 16/904,868 mailed Oct. 5, 2021.

(56)     References Cited

OTHER PUBLICATIONS

Non-Final Office Action for U.S. Appl. No. 16/905,400 mailed Apr. 27, 2022.

Non-Final Office Action for U.S. Appl. No. 16/905,400 mailed Jul. 22, 2021.

Non-Final Office Action for U.S. Appl. No. 17/051,399 mailed Aug. 18, 2023.

Non-Final Office Action for U.S. Appl. No. 17/051,550 mailed Dec. 15, 2022.

Non-Final Office Action for U.S. Appl. No. 17/051,550 mailed Oct. 24, 2023.

Non-Final Office Action for U.S. Appl. No. 17/051,585 mailed Jan. 8, 2024.

Non-Final Office Action for U.S. Appl. No. 17/051,585 mailed Mar. 29, 2023.

Non-Final Office Action for U.S. Appl. No. 17/051,600 mailed Jan. 17, 2024.

Non-Final Office Action for U.S. Appl. No. 17/179,116 mailed Mar. 24, 2023.

Non-Final Office Action for U.S. Appl. No. 17/326,980 mailed Jul. 11, 2023.

Non-Final Office Action for U.S. Appl. No. 17/330,657 mailed Aug. 11, 2021.

Non-Final Office Action for U.S. Appl. No. 17/444,792 mailed Feb. 10, 2023.

Non-Final Office Action for U.S. Appl. No. 17/444,792 mailed Nov. 17, 2023.

Non-Final Office Action for U.S. Appl. No. 17/446,256 mailed Apr. 13, 2023.

Non-Final Office Action for U.S. Appl. No. 17/446,654 mailed Sep. 8, 2023.

Non-Final Office Action for U.S. Appl. No. 17/448,811 mailed Mar. 1, 2023.

Non-Final Office Action for U.S. Appl. No. 17/450,864 mailed May 10, 2023.

Non-Final Office Action for U.S. Appl. No. 17/451,345 mailed Dec. 7, 2022.

Non-Final Office Action for U.S. Appl. No. 17/451,354 mailed May 3, 2023.

Non-Final Office Action for U.S. Appl. No. 17/453,260 mailed Mar. 14, 2023.

Non-Final Office Action for U.S. Appl. No. 17/453,560 mailed Oct. 16, 2023.

Non-Final Office Action for U.S. Appl. No. 17/501,591 mailed Apr. 25, 2023.

Non-Final Office Action for U.S. Appl. No. 17/645,821 mailed Oct. 25, 2023.

Non-Final Office Action for U.S. Appl. No. 17/646,771 mailed Jul. 5, 2023.

Non-Final Office Action for U.S. Appl. No. 17/653,137 mailed Apr. 7, 2023.

Non-Final Office Action for U.S. Appl. No. 17/653,137 mailed Jan. 18, 2024.

Non-Final Office Action for U.S. Appl. No. 17/655,464 mailed Mar. 14, 2023.

Non-Final Office Action for U.S. Appl. No. 17/657,474 mailed Sep. 12, 2023.

Non-Final Office Action for U.S. Appl. No. 17/661,090 mailed Jul. 6, 2023.

Non-Final Office Action for U.S. Appl. No. 17/662,700 mailed Jul. 22, 2022.

Non-Final Office Action for U.S. Appl. No. 17/663,330 mailed Jun. 29, 2023.

Non-Final Office Action for U.S. Appl. No. 17/664,487 mailed Jun. 8, 2023.

Non-Final Office Action for U.S. Appl. No. 17/808,354 mailed Nov. 28, 2023.

Non-Final Office Action for U.S. Appl. No. 18/139,523 mailed Aug. 17, 2023.

Non-Final Office Action for U.S. Appl. No. 18/140,163 mailed Nov. 9, 2023.

Non-Final Office Action for U.S. Appl. No. 18/140,751 mailed Sep. 14, 2023.

Non-Final Office Action for U.S. Appl. No. 18/198,464 mailed Dec. 7, 2023.

Non-Final Office Action for U.S. Appl. No. 29/741,751 mailed Jan. 18, 2022.

Notice of Allowance for U.S. Appl. No. 16/245,726 mailed Jul. 6, 2023.

Notice of Allowance for U.S. Appl. No. 16/369,676 mailed Nov. 14, 2023.

Notice of Allowance for U.S. Appl. No. 16/449,039 mailed Dec. 15, 2022.

Notice of Allowance for U.S. Appl. No. 16/899,956 mailed Apr. 19, 2022.

Notice of Allowance for U.S. Appl. No. 16/899,956 mailed Aug. 10, 2022.

Notice of Allowance for U.S. Appl. No. 16/899,956 mailed Dec. 1, 2022.

Notice of Allowance for U.S. Appl. No. 16/899,956 mailed Dec. 29, 2021.

Notice of Allowance for U.S. Appl. No. 16/905,400 mailed Aug. 17, 2022.

Notice of Allowance for U.S. Appl. No. 17/051,554 mailed Jul. 6, 2023.

Notice of Allowance for U.S. Appl. No. 17/051,554 mailed Oct. 18, 2023.

Notice of Allowance for U.S. Appl. No. 17/088,272 mailed Aug. 5, 2021.

Notice of Allowance for U.S. Appl. No. 17/088,272 mailed Mar. 4, 2022.

Notice of Allowance for U.S. Appl. No. 17/088,272 mailed Nov. 24, 2021.

Notice of Allowance for U.S. Appl. No. 17/330,657 mailed Mar. 16, 2022.

Notice of Allowance for U.S. Appl. No. 17/330,657 mailed Nov. 26, 2021.

Notice of Allowance for U.S. Appl. No. 17/461,036 mailed Feb. 22, 2023.

Notice of Allowance for U.S. Appl. No. 17/461,036 mailed Jun. 30, 2023.

Notice of Allowance for U.S. Appl. No. 17/461,036 mailed Oct. 6, 2022.

Notice of Allowance for U.S. Appl. No. 17/662,700 mailed Jul. 28, 2023.

Notice of Allowance for U.S. Appl. No. 17/662,700 mailed Mar. 28, 2023.

Notice of Allowance for U.S. Appl. No. 17/662,700 mailed Nov. 15, 2023.

Notice of Allowance for U.S. Appl. No. 17/663,046 mailed Jan. 30, 2023.

Notice of Allowance for U.S. Appl. No. 18/299,788 mailed Jul. 24, 2023.

Notice of Allowance for U.S. Appl. No. 18/299,788 mailed Nov. 6, 2023.

Notice of Allowance for U.S. Appl. No. 29/741,751 mailed Jun. 9, 2022.

Restriction Requirement for U.S. Appl. No. 16/433,773 mailed Dec. 7, 2021.

Restriction Requirement for U.S. Appl. No. 17/051,600 mailed Sep. 21, 2023.

Restriction Requirement for U.S. Appl. No. 17/326,980 mailed Mar. 20, 2023.

Restriction Requirement for U.S. Appl. No. 17/446,256 mailed Jan. 23, 2023.

Restriction Requirement for U.S. Appl. No. 17/645,821 mailed Jul. 12, 2023.

Restriction Requirement for U.S. Appl. No. 17/646,771 mailed Apr. 6, 2023.

Restriction Requirement for U.S. Appl. No. 17/657,474 mailed Jun. 30, 2023.

(56)     References Cited

OTHER PUBLICATIONS

Restriction Requirement for U.S. Appl. No. 18/134,857 mailed Oct. 23, 2023.
Submission in Opposition Proceedings for European Application No. 17807547.9 filed Jan. 10, 2024.
Text Messages to Lorena Eckert Re Prototype PureWick Holder dated Apr. 16, 2022.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/384,196, filed Dec. 19, 2016.
U.S. Appl. No. 16/245,726, filed Jan. 11, 2019.
U.S. Appl. No. 17/394,055, filed Aug. 4, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/451,719, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 63/008,112, filed Apr. 10, 2020.
U.S. Appl. No. 63/047,374, filed Jul. 2, 2020.
U.S. Appl. No. 63/067,542, filed Aug. 19, 2020.
U.S. Appl. No. 63/073,545, filed Sep. 2, 2020.
U.S. Appl. No. 63/073,553, filed Sep. 2, 2020.
U.S. Appl. No. 63/094,646, filed Oct. 21, 2020.
U.S. Appl. No. 63/109,084, filed Nov. 3, 2020.
U.S. Appl. No. 63/133,892, filed Jan. 5, 2021.
U.S. Appl. No. 63/138,878, filed Jan. 19, 2021.
U.S. Appl. No. 63/150,640, filed Feb. 18, 2021.
U.S. Appl. No. 63/159,186, filed Mar. 10, 2021.
U.S. Appl. No. 63/191,558, filed May 21, 2021.
U.S. Appl. No. 63/192,289, filed May 24, 2021.
U.S. Appl. No. 63/193,891, filed May 27, 2021.
U.S. Appl. No. 63/208,262, filed Jun. 8, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
U.S. Appl. No. 63/308,190, filed Feb. 9, 2022.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.

(56) References Cited

OTHER PUBLICATIONS

*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
"Rising Warrior Insulated Gallon Jug Cover", https://www.amazon.com/Rising-Warrior-Insulated-Sleeve, 2021, 2 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali, "Sustainability Assessment: Seventh Generation Diapers versus gDiapers", The University of Vermont, Dec. 6, 2011, pp. 1-31.
Autumn, et al., "Frictional adhesion: a new angle on gecko attachment", The Journal of Experimental Biology, 2006, pp. 3569-3579.
Cañas, et al., "Effect of nano- and micro-roughness on adhesion of bioinspired micropatterned surfaces", Acta Biomaterialia 8 , 2012, pp. 282-288.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al. , "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.
Hwang, et al. , "Multifunctional Smart Skin Adhesive Patches for Advanced Health Care", Adv. Healthcare Mater, 2018, pp. 1-20.
Jagota, et al. , "Adhesion, friction, and compliance of bio-mimetic and bio-inspired structured interfaces", Materials Science and Engineering, 2011, pp. 253-292.
Jeong, et al. , "A nontransferring dry adhesive with hierarchical polymer nanohairs", PNAS, Apr. 7, 2009, pp. 5639-5644.
Jeong, et al. , "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Merriam-Webster Dictionary, "Embed Definition & Meaning", https://www.merriam-webster.com/dictionary/embed last accessed Aug. 3, 2023, 2003.

Parness, et al., "A microfabricated wedge-shaped adhesive array displaying gecko-like dynamic adhesion, directionality", J.R. Soc. Interface, 2009, pp. 1223-1232.
Pieper , et al., "An external urine-collection device for women: A clinical trial", Journal of ER Nursing, vol. 20, No. 2, Mar./Apr. 1993, pp. 51-55.
Tsipenyuk, et al., "Use of biomimetic hexagonal surface texture in friction against lubricated skin", Journal of The Royal Society—Interface, 2014, pp. 1-6.
Vinas, "A Solution For An Awkward—But Serious—Subject", http://www.aero-news.net/index.cfm?do=main.textpost&id=69ae2bb1-838b-4098-a7b5-7flbb2505688 last accessed Feb. 8, 2021.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/899,956 mailed Apr. 19, 2021.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.

(56) References Cited

OTHER PUBLICATIONS

International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.

Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/899,956 mailed Oct. 16, 2020.
Non-Final Office Action for U.S. Appl. No. 16/904,868 mailed Nov. 25, 2020.
Non-Final Office Action for U.S. Appl. No. 16/905,400 mailed Dec. 2, 2020.
Non-Final Office Action for U.S. Appl. No. 17/088,272 mailed Jan. 25, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019,.
Notice of Allowance for U.S. Appl. No. 15/238,427 mailed May 23, 2019,.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.

(56) References Cited

OTHER PUBLICATIONS

Restriction Requirement for U.S. Appl. No. 16/478,180 mailed May 25, 2021.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 29/741,751, filed Jul. 15, 2020.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/071,438, filed Aug. 28, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,210, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/214,551, filed Jun. 24, 2021.
U.S. Appl. No. 63/214,570, filed Jun. 24, 2021.
Defendant and Counterclaim Plaintiff Sage Products, LLC's Answer, Defenses, and Counterclaims to Plaintiff's Amended Complaint, Nov. 1, 2019.
Memorandum Order, Feb. 2021, 14 pgs.
Sage's Initial Invalidity Contentions Regarding U.S. Pat. Nos. 8,287,508; 10,226,375; and 10,390,989, May 29, 2020, 193 pages.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. Nos. 8,287,508, 10,226,375, 10,390,989, and 10,376,407, 292 pages.
Boehringer CareDry System—Second Generation for Non-Invasive Urinary Management for Females, Mar. 2021, 3 pgs.
Excerpts from the 508 (U.S. Pat. No. 8,278,508) Patent's Prosecution History, 2020, 99 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
PureWick's Response to Interrogatory No. 9 in *PureWick, LLC* v. *Sage Products, LLC*, Case No. 19-1508-MN, Mar. 23, 2020, 6 pages.
Sage's Preliminary Identification of Claim Elements and Proposed Constructions for U.S. Pat. Nos. 8,287,508, 10,226,376, 10,390,989 and 10,376,407, Case No. 19-1508-MN, 7 pages.
Decision Granting Institution of Inter Partes Review for U.S. Pat. No. 8,287,508, Case No. 2020-01426, Feb. 17, 2021, 39 pages.
Corrected Certificate of Service, Case No. IPR2020-01426, U.S. Pat. No. 8,287,508, 2020, 2 pages.
Declaration of Diane K. Newman Curriculum Vitae, Petition for Interparties Review, 2020, pp. 1-199.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, Omni Medical, 8 pages.

(56) References Cited

OTHER PUBLICATIONS

"AMXDmax In-Flight Bladder Relief", Omni Medical; Omni Medical Systems, Inc., 2015.
"AMXDX—Advanced Mission Extender Device Brochure", Omni Medical, Omni Brochure—http://www.omnimedicalsys.com/uploads/AMXDFixedWing.pdf, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, Omni Presentation https://www.omnimedicalsys.com/uploads/AMXDmax_HSD.pdf, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Step by Step How Ur24 WorksHome", http://medicalpatentur24.com, last accessed Dec. 6, 2017, Aug. 30, 2017, 4 pages.
"Underwear that absorbs your period", Thinx!, https://www.shethinx.com/pages/thinx-it-works last accessed Jun. 24, 2020, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
Hollister, "Retracted Penis Pouch by Hollister", Vitality Medical.com, https://www.vitalitymedical.com/hollister-retracted-penis-pouch.html last accessed Jun. 24, 2020, 6 pages.
Macaulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
PureWick, "Incontinence Relief for Women", Presentation, Sep. 23, 2015, 7 pages.
Pytlik, "Super Absorbent Polymers", University of Buffalo, http://www.courses.sens.buffalo.edu/ce435/Diapers/Diapers.html, accessed on Feb. 17, 2017.
Sachtman, "New Relief for Pilots? It Depends", Wired, https://www.wired.com/2008/05/pilot-relief/, 2008, 2 pages.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/051,585 mailed Oct. 8, 2024.

Advisory Action for U.S. Appl. No. 17/444,792 mailed Jul. 8, 2024.
Advisory Action for U.S. Appl. No. 17/446,256 mailed Nov. 19, 2024.
Advisory Action for U.S. Appl. No. 17/446,654 mailed Apr. 15, 2024.
Advisory Action for U.S. Appl. No. 17/446,654 mailed Feb. 28, 2025.
Advisory Action for U.S. Appl. No. 17/450,864 mailed Mar. 21, 2024.
Advisory Action for U.S. Appl. No. 17/451,345 mailed Jul. 3, 2024.
Advisory Action for U.S. Appl. No. 17/451,354 mailed Jan. 30, 2024.
Advisory Action for U.S. Appl. No. 17/501,591 mailed Feb. 22, 2024.
Advisory Action for U.S. Appl. No. 17/597,673 mailed Jan. 7, 2025.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 17/655,464 mailed Feb. 25, 2025.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/003,029 mailed Jan. 8, 2025.
Advisory Action for U.S. Appl. No. 18/134,857 mailed Oct. 23, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Advisory Action for U.S. Appl. No. 18/164,800 mailed Jan. 8, 2025.
Corrected Notice of Allowability for U.S. Appl. No. 17/326,980 mailed Feb. 8, 2024.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/646,771 mailed Jan. 17, 2025.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 16/478,180 mailed Feb. 28, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/446,256 mailed Aug. 7, 2024.

(56)        References Cited

OTHER PUBLICATIONS

Final Office Action for U.S. Appl. No. 17/446,654 mailed Dec. 18, 2024.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/451,345 mailed Feb. 6, 2025.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/597,673 mailed Oct. 22, 2024.
Final Office Action for U.S. Appl. No. 17/625,941 mailed Feb. 18, 2025.
Final Office Action for U.S. Appl. No. 17/645,821 mailed Apr. 3, 2024.
Final Office Action for U.S. Appl. No. 17/653,137 mailed Aug. 7, 2024.
Final Office Action for U.S. Appl. No. 17/653,314 mailed Jan. 30, 2025.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 17/808,354 mailed Apr. 10, 2024.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Oct. 22, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031432 mailed Feb. 29, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.

International Search Report and Written Opinion from International Application No. PCT/US2023/085516 mailed Aug. 26, 2024.
International Search Report and Written Opinion from International Application No. PCT/US2024/053681 mailed Jan. 27, 2025.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/448,811 mailed Jul. 3, 2024.
Issue Notification for U.S. Appl. No. 17/450,864 mailed Jan. 8, 2025.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/529,769 mailed Feb. 19, 2025.
Issue Notification for U.S. Appl. No. 17/633,330 mailed Feb. 26, 2025.
Issue Notification for U.S. Appl. No. 17/657,474 mailed Jun. 19, 2024.
Issue Notification for U.S. Appl. No. 17/661,090 mailed Feb. 5, 2025.
Issue Notification for U.S. Appl. No. 17/662,700 mailed Oct. 23, 2024.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/140,751 mailed Feb. 12, 2025.
Issue Notification for U.S. Appl. No. 18/198,464 mailed Nov. 20, 2024.
Issue Notification for U.S. Appl. No. 18/299,788 mailed Feb. 21, 2024.
Issue Notification for U.S. Appl. No. 18/389,009 mailed Dec. 18, 2024.
Issue Notification for U.S. Appl. No. 18/426,795 mailed Feb. 19, 2025.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/433,773 mailed Feb. 28, 2025.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 16/904,868 mailed Mar. 12, 2024.
Non-Final Office Action for U.S. Appl. No. 17/051,600 mailed Feb. 28, 2025.
Non-Final Office Action for U.S. Appl. No. 17/179,116 mailed Feb. 26, 2024.
Non-Final Office Action for U.S. Appl. No. 17/378,015 mailed Jul. 5, 2024.

(56)     References Cited

OTHER PUBLICATIONS

Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/450,864 mailed May 29, 2024.
Non-Final Office Action for U.S. Appl. No. 17/451,345 mailed Jan. 17, 2024.
Non-Final Office Action for U.S. Appl. No. 17/451,345 mailed Jul. 25, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/597,673 mailed Mar. 20, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/646,771 mailed Apr. 24, 2024.
Non-Final Office Action for U.S. Appl. No. 17/653,137 mailed Jan. 28, 2025.
Non-Final Office Action for U.S. Appl. No. 17/653,314 mailed Aug. 29, 2024.
Non-Final Office Action for U.S. Appl. No. 17/653,920 mailed Mar. 15, 2024.
Non-Final Office Action for U.S. Appl. No. 17/653,920 mailed Nov. 27, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/664,914 mailed Jan. 31, 2024.
Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/907,125 mailed Dec. 13, 2024.
Non-Final Office Action for U.S. Appl. No. 18/003,029 mailed Mar. 26, 2024.

Non-Final Office Action for U.S. Appl. No. 18/134,857 mailed Jan. 25, 2024.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 16/904,868 mailed Sep. 29, 2024.
Notice of Allowance for U.S. Appl. No. 17/051,550 mailed Feb. 7, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/596,629 mailed Jan. 29, 2025.
Notice of Allowance for U.S. Appl. No. 17/597,673 mailed Feb. 26, 2025.
Notice of Allowance for U.S. Appl. No. 17/646,771 mailed Dec. 17, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 17/663,330 mailed Nov. 20, 2024.

(56)             References Cited

OTHER PUBLICATIONS

Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 17/749,340 mailed Feb. 14, 2025.
Notice of Allowance for U.S. Appl. No. 18/134,857 mailed Feb. 20, 2025.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Apr. 17, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/667,097 mailed Mar. 20, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/013,822, filed Sep. 7, 2020.
U.S. Appl. No. 17/444,792, filed Aug. 10, 2021.
U.S. Appl. No. 18/249,577, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/426,795, filed Jan. 30, 2024.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/103,165, filed Feb. 11, 2025.
U.S. Appl. No. 63/181,709, filed Apr. 29, 2021.
U.S. Appl. No. 63/561,893, filed Dec. 11, 2023.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, "Chapter 5 Applications of Polyethylene Oxide (Polyox) in Hydrophilic Matrices", Hydrophilic Matrix Tablets for Oral Controlled Release, AAPS Advances in the Pharmaceutical Sciences vol. 16, 2014, pp. 123-141.
Wikipedia article, "Decibel", https://web.archive.org/web/2020041521917/https://en.wikipedia/org/wiki/Decibel last accessed Mar. 11, 2024, 21 pages.
Wikipedia article, "Fiberglass", https://web.archive.org.web/20200309194847/https://en.wikipedia.org/wiki/Fiberglass last accessed Mar. 11, 2024.
Advisory Action for U.S. Appl. No. 16/452,258 mailed May 5, 2025.
Advisory Action for U.S. Appl. No. 17/451,345 mailed May 13, 2025.
Advisory Action for U.S. Appl. No. 17/595,747 mailed Mar. 17, 2025.
Advisory Action for U.S. Appl. No. 17/653,314 mailed Apr. 8, 2025.
Advisory Action for U.S. Appl. No. 17/664,487 mailed Apr. 24, 2025.
Corrected Notice of Allowability for U.S. Appl. No. 17/996,253 mailed Apr. 28, 2025.
Corrected Notice of Allowability for U.S. Appl. No. 18/134,857 mailed Mar. 14, 2025.
Final Office Action for U.S. Appl. No. 17/378,015 mailed Jun. 18, 2025.
Final Office Action for U.S. Appl. No. 17/446,256 mailed Jun. 11, 2025.
Final Office Action for U.S. Appl. No. 17/597,408 mailed Mar. 24, 2025.
Final Office Action for U.S. Appl. No. 17/614,173 mailed May 20, 2025.
Final Office Action for U.S. Appl. No. 17/628,411 mailed Apr. 30, 2025.
Final Office Action for U.S. Appl. No. 17/653,920 mailed Apr. 24, 2025.

(56)        References Cited

OTHER PUBLICATIONS

Final Office Action for U.S. Appl. No. 17/757,311 mailed Mar. 31, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/907,125 mailed Apr. 30, 2025.
Final Office Action for U.S. Appl. No. 18/139,523 mailed May 8, 2025.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,585 mailed Mar. 26, 2025.
Issue Notification for U.S. Appl. No. 17/501,591 mailed Mar. 5, 2025.
Issue Notification for U.S. Appl. No. 17/597,673 mailed Jun. 4, 2025.
Issue Notification for U.S. Appl. No. 17/646,771 mailed Mar. 19, 2025.
Issue Notification for U.S. Appl. No. 17/749,340 mailed May 28, 2025.
Issue Notification for U.S. Appl. No. 18/134,857 mailed May 28, 2025.
Issue Notification for U.S. Appl. No. 18/415,080 mailed Apr. 9, 2025.
Issue Notification for U.S. Appl. No. 18/584,002 mailed Apr. 16, 2025.
Non-Final Office Action for U.S. Appl. No. 17/446,654 mailed May 1, 2025.
Non-Final Office Action for U.S. Appl. No. 17/451,354 mailed Mar. 19, 2025.
Non-Final Office Action for U.S. Appl. No. 17/595,747 mailed Jun. 12, 2025.
Non-Final Office Action for U.S. Appl. No. 17/631,619 mailed Mar. 19, 2025.
Non-Final Office Action for U.S. Appl. No. 17/645,821 mailed Mar. 31, 2025.
Non-Final Office Action for U.S. Appl. No. 17/653,314 mailed May 8, 2025.
Non-Final Office Action for U.S. Appl. No. 17/655,464 mailed Mar. 20, 2025.
Non-Final Office Action for U.S. Appl. No. 17/664,487 mailed May 19, 2025.
Non-Final Office Action for U.S. Appl. No. 17/754,736 mailed Mar. 31, 2025.
Non-Final Office Action for U.S. Appl. No. 17/756,201 mailed Apr. 24, 2025.
Non-Final Office Action for U.S. Appl. No. 17/758,152 mailed Apr. 8, 2025.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/878,268 mailed Mar. 17, 2025.

Non-Final Office Action for U.S. Appl. No. 17/912,147 mailed May 29, 2025.
Non-Final Office Action for U.S. Appl. No. 17/996,064 mailed Mar. 6, 2025.
Non-Final Office Action for U.S. Appl. No. 18/003,029 mailed Apr. 18, 2025.
Non-Final Office Action for U.S. Appl. No. 18/006,807 mailed May 29, 2025.
Non-Final Office Action for U.S. Appl. No. 18/042,842 mailed May 22, 2025.
Non-Final Office Action for U.S. Appl. No. 18/043,618 mailed May 19, 2025.
Non-Final Office Action for U.S. Appl. No. 18/164,800 mailed Apr. 25, 2025.
Non-Final Office Action for U.S. Appl. No. 18/247,986 mailed Jun. 4, 2025.
Non-Final Office Action for U.S. Appl. No. 18/264,004 mailed May 15, 2025.
Notice of Allowance for U.S. Appl. No. 17/444,792 mailed Mar. 28, 2025.
Notice of Allowance for U.S. Appl. No. 17/596,629 mailed May 27, 2025.
Notice of Allowance for U.S. Appl. No. 17/758,316 mailed Mar. 24, 2025.
Notice of Allowance for U.S. Appl. No. 17/996,155 mailed Mar. 11, 2025.
Notice of Allowance for U.S. Appl. No. 17/996,253 mailed Apr. 11, 2025.
Notice of Allowance for U.S. Appl. No. 17/996,468 mailed Apr. 14, 2025.
Notice of Allowance for U.S. Appl. No. 18/007,105 mailed Jun. 17, 2025.
Restriction Requirement for U.S. Appl. No. 17/755,236 mailed Apr. 24, 2025.
Restriction Requirement for U.S. Appl. No. 17/929,887 mailed Mar. 10, 2025.
Restriction Requirement for U.S. Appl. No. 17/930,238 mailed Apr. 17, 2025.
Restriction Requirement for U.S. Appl. No. 18/041,109 mailed Jun. 4, 2025.
Restriction Requirement for U.S. Appl. No. 18/150,360 mailed May 19, 2025.
Supplemental Notice of Allowance for U.S. Appl. No. 17/597,673 mailed Apr. 10, 2025.
U.S. Appl. No. 17/596,629, filed Dec. 15, 2021.
U.S. Appl. No. 19/078,602, filed Mar. 13, 2025.
U.S. Appl. No. 19/092,262, filed Mar. 27, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 63/564,696, filed Mar. 13, 2024.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.
"Surface Energy Data for Cellulose acetate, CAS # 9004-35-7", Diviersified Enterprises, 2009, 1 page.
"Tube Definition & Meaning" Merriam Webster Dictionary, 2025, <https://www.merriam-webster.com/dictionary/tube>.
Advisory Action for U.S. Appl. No. 17/378,015 mailed Oct. 28, 2025.
Advisory Action for U.S. Appl. No. 17/446,256 mailed Nov. 6, 2025.
Advisory Action for U.S. Appl. No. 17/757,311 mailed Jul. 2, 2025.
Corrected Notice of Allowability for U.S. Appl. No. 17/444,792 mailed Jun. 24, 2025.

(56) References Cited

OTHER PUBLICATIONS

Corrected Notice of Allowability for U.S. Appl. No. 17/653,314 mailed Oct. 29, 2025.

Corrected Notice of Allowability for U.S. Appl. No. 17/808,354 mailed Nov. 25, 2025.

Corrected Notice of Allowability for U.S. Appl. No. 18/260,122 mailed Aug. 11, 2025.

Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.

Final Office Action for U.S. Appl. No. 17/051,600 mailed Aug. 6, 2025.

Final Office Action for U.S. Appl. No. 17/446,654 mailed Dec. 22, 2025.

Final Office Action for U.S. Appl. No. 17/631,619 mailed Oct. 1, 2025.

Final Office Action for U.S. Appl. No. 17/653,137 mailed Jun. 25, 2025.

Final Office Action for U.S. Appl. No. 17/664,487 mailed Jan. 5, 2026.

Final Office Action for U.S. Appl. No. 17/756,201 mailed Dec. 30, 2025.

Final Office Action for U.S. Appl. No. 17/929,887, filed Jan. 13, 2026.

Final Office Action for U.S. Appl. No. 18/003,029 mailed Nov. 26, 2025.

Final Office Action for U.S. Appl. No. 18/006,807 mailed Dec. 23, 2025.

Final Office Action for U.S. Appl. No. 18/043,618 mailed Nov. 26, 2025.

Final Office Action for U.S. Appl. No. 18/164,800 mailed Dec. 5, 2025.

Final Office Action for U.S. Appl. No. 18/247,986 mailed Jan. 7, 2026.

Final Office Action for U.S. Appl. No. 18/265,736 mailed Dec. 1, 2025.

International Search Report and Written Opinion from International Application No. PCT/US2025/018913 mailed Jun. 18, 2025.

Issue Notification for U.S. Appl. No. 17/444,792 mailed Jun. 25, 2025.

Issue Notification for U.S. Appl. No. 17/653,920 mailed Oct. 22, 2025.

Issue Notification for U.S. Appl. No. 17/755,236 mailed Oct. 29, 2025.

Issue Notification for U.S. Appl. No. 17/758,316 mailed Jun. 25, 2025.

Issue Notification for U.S. Appl. No. 17/907,125 mailed Dec. 30, 2025.

Issue Notification for U.S. Appl. No. 17/996,064 mailed Nov. 5, 2025.

Issue Notification for U.S. Appl. No. 17/996,155 mailed Oct. 8, 2025.

Issue Notification for U.S. Appl. No. 17/996,253 mailed Oct. 29, 2025.

Issue Notification for U.S. Appl. No. 17/996,468 mailed Nov. 26, 2025.

Issue Notification for U.S. Appl. No. 18/007,105 mailed Oct. 1, 2025.

Issue Notification for U.S. Appl. No. 18/044,413 mailed Dec. 30, 2025.

Issue Notification for U.S. Appl. No. 18/260,122 mailed Nov. 12, 2025.

Non-Final Office Action for U.S. Appl. No. 16/452,258 mailed Sep. 24, 2025.

Non-Final Office Action for U.S. Appl. No. 17/378,015 mailed Dec. 12, 2025.

Non-Final Office Action for U.S. Appl. No. 17/446,256 mailed Dec. 2, 2025.

Non-Final Office Action for U.S. Appl. No. 17/614,173 mailed Dec. 29, 2025.

Non-Final Office Action for U.S. Appl. No. 17/628,411 mailed Dec. 22, 2025.

Non-Final Office Action for U.S. Appl. No. 17/635,866 mailed Jul. 29, 2025.

Non-Final Office Action for U.S. Appl. No. 17/759,697 mailed Sep. 17, 2025.

Non-Final Office Action for U.S. Appl. No. 17/929,887 mailed Jun. 25, 2025.

Non-Final Office Action for U.S. Appl. No. 17/930,238 mailed Jun. 30, 2025.

Non-Final Office Action for U.S. Appl. No. 17/933,590 mailed Jul. 29, 2025.

Non-Final Office Action for U.S. Appl. No. 17/996,556 mailed Dec. 22, 2025.

Non-Final Office Action for U.S. Appl. No. 18/115,444 mailed Oct. 22, 2025.

Non-Final Office Action for U.S. Appl. No. 18/139,523 mailed Nov. 19, 2025.

Non-Final Office Action for U.S. Appl. No. 18/150,360 mailed Nov. 5, 2025.

Non-Final Office Action for U.S. Appl. No. 18/249,577 mailed Nov. 17, 2025.

Non-Final Office Action for U.S. Appl. No. 18/254,638 mailed Nov. 17, 2025.

Non-Final Office Action for U.S. Appl. No. 18/259,626 mailed Jul. 11, 2025.

Non-Final Office Action for U.S. Appl. No. 18/260,394, filed Jan. 13, 2026.

Non-Final Office Action for U.S. Appl. No. 18/264,278 mailed Nov. 10, 2025.

Non-Final Office Action for U.S. Appl. No. 18/265,736 mailed Jul. 1, 2025.

Non-Final Office Action for U.S. Appl. No. 18/548,152 mailed Sep. 16, 2025.

Non-Final Office Action for U.S. Appl. No. 18/553,625 mailed Oct. 2, 2025.

Non-Final Office Action for U.S. Appl. No. 18/556,945 mailed Dec. 19, 2025.

Non-Final Office Action for U.S. Appl. No. 18/757,964 mailed Aug. 20, 2025.

Notice of Allowance for U.S. Appl. No. 16/433,773 mailed Oct. 10, 2025.

Notice of Allowance for U.S. Appl. No. 17/051,399 mailed Nov. 17, 2025.

Notice of Allowance for U.S. Appl. No. 17/051,600 mailed Jan. 5, 2026.

Notice of Allowance for U.S. Appl. No. 17/451,345 mailed Jun. 24, 2025.

Notice of Allowance for U.S. Appl. No. 17/451,354 mailed Nov. 18, 2025.

Notice of Allowance for U.S. Appl. No. 17/625,941 mailed Nov. 13, 2025.

Notice of Allowance for U.S. Appl. No. 17/645,821 mailed Nov. 24, 2025.

Notice of Allowance for U.S. Appl. No. 17/653,137 mailed Oct. 22, 2025.

Notice of Allowance for U.S. Appl. No. 17/653,314 mailed Oct. 20, 2025.

Notice of Allowance for U.S. Appl. No. 17/653,920 mailed Jul. 9, 2025.

Notice of Allowance for U.S. Appl. No. 17/755,236 mailed Jul. 17, 2025.

Notice of Allowance for U.S. Appl. No. 17/808,354 mailed Nov. 12, 2025.

Notice of Allowance for U.S. Appl. No. 17/878,268 mailed Oct. 15, 2025.

Notice of Allowance for U.S. Appl. No. 17/907,125 mailed Sep. 26, 2025.

Notice of Allowance for U.S. Appl. No. 17/912,147 mailed Dec. 3, 2025.

(56)         References Cited

OTHER PUBLICATIONS

Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,253 mailed Jul. 11, 2025.
Notice of Allowance for U.S. Appl. No. 17/996,468 mailed Jul. 15, 2025.
Notice of Allowance for U.S. Appl. No. 18/044,413 mailed Sep. 16, 2025.
Notice of Allowance for U.S. Appl. No. 18/260,122 mailed Jul. 30, 2025.
Restriction Requirement for U.S. Appl. No. 17/625,887 mailed Sep. 2, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Oct. 23, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/260,394 mailed Jul. 25, 2025.
Restriction Requirement for U.S. Appl. No. 18/294,370 mailed Nov. 26, 2025.
Restriction Requirement for U.S. Appl. No. 18/335,579 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/569,711 mailed Jan. 6, 2026.
Restriction Requirement for U.S. Appl. No. 18/569,778 mailed Jan. 15, 2026.
Restriction Requirement for U.S. Appl. No. 18/662,216 mailed Nov. 26, 2025.
Restriction Requirement for U.S. Appl. No. 19/237,638 mailed Dec. 18, 2025.
U.S. Appl. No. 18/034,902, filed May 2, 2023.
U.S. Appl. No. 19/329,723, filed Sep. 16, 2025.
U.S. Appl. No. 19/337,217, filed Sep. 23, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150, filed Dec. 12, 2025.
U.S. Appl. No. 19/443,729, filed Jan. 8, 2026.
U.S. Appl. No. 19/447,347, filed Jan. 13, 2026.
U.S. Appl. No. 19/451,614, filed Jan. 16, 2026.
U.S. Appl. No. 19/491,481, filed Dec. 9, 2025.
U.S. Appl. No. 19/494,631, filed Dec. 18, 2025.

* cited by examiner

_600_

| Providing a fluid impermeable barrier | _605_ |

↓

| Inserting a fluid permeable body into the fluid impermeable barrier | _610_ |

↓

| Inserting an inlet of a conduit into the fluid impermeable body | _615_ |

↓

| Inserting the inlet of the conduit at least partially into a bore of the fluid permeable body | _620_ |

*700*

| Positioning a fluid permeable body of a fluid collection device adjacent to a female urethra of a user | *705* |

| Securing the fluid collection device to the user | *710* |

| Receiving fluids from the female urethra into the chamber of the fluid collection device | *715* |

FLUID COLLECTION DEVICES INCLUDING AN ENLARGED BASE, AND SYSTEMS AND METHODS OF USE

CROSS-REFERENCE TO RELATED APPLICATIONS

This application claims priority to U.S. Provisional Patent Application No. 63/061,241 filed on Aug. 5, 2020, the disclosure of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experienced by pilots, drivers, and workers in hazardous areas. Additionally, fluid collection from the individual may be needed for monitoring purposes or clinical testing.

Bed pans and urinary catheters, such as a Foley catheter, can be used to address some of these circumstances. However, bed pans and urinary catheters have several problems associated therewith. For example, bed pans can be prone to discomfort, pressure ulcers spills, and other hygiene issues. Urinary catheters be can be uncomfortable, painful, and can cause urinary tract infections.

Thus, users and manufacturers of fluid collection devices continue to seek new and improved devices, systems, and methods to collect urine.

SUMMARY

Embodiments disclosed herein are fluid collection devices and methods of assembling fluid collection devices. In an embodiment, a urine collection device includes a fluid impermeable barrier, a base, and a fluid permeable body. The fluid impermeable barrier has a first lateral dimension and at least partially defines a chamber, an aperture configured to receive a conduit therethrough, and an opening. The base extends from the fluid impermeable barrier distal to the aperture and has a second lateral dimension greater than the first lateral dimension. The fluid permeable body is positioned at least partially within the chamber to extend across at least a portion of the opening. The fluid permeable body is configured to wick fluid away from the opening.

In an embodiment, a fluid collection device includes a fluid impermeable barrier and a base. The fluid impermeable barrier has a first lateral dimension and at least partially defines a chamber sized and dimensioned to house a fluid permeable body, an aperture configured to receive a conduit therethrough, and an opening. The base extends from the fluid impermeable barrier distal to the aperture and has a second lateral dimension greater than the first lateral dimension. The opening is positioned between the base and the aperture.

In an embodiment, a fluid collection device includes a fluid impermeable barrier, a base, and a fluid permeable body. The fluid impermeable barrier at least partially defines a chamber, an aperture configured to receive a conduit therethrough, and an opening. The base extends from the fluid impermeable barrier distal to the aperture and includes at least one of a closed cell foam or a gel material. The fluid permeable body is positioned at least partially within the chamber to extend across at least a portion of the opening. The fluid permeable body is configured to wick fluid away from the opening.

In an embodiment, a method of positioning a urine collection system on an individual or collecting urine from an individual includes positioning a fluid permeable body of a fluid collection device adjacent to a urethra of a user. The fluid permeable body is positioned within a chamber defined by a fluid impermeable barrier of the fluid collection device to extend across at least a portion of an opening defined by the fluid impermeable barrier. The method also includes positioning a base of the fluid collection device between the buttocks of the user. The base has one or more of (1) a lateral dimension that is greater than a lateral dimension of the fluid impermeable barrier; or (2) at least one of a closed cell foam or a gel material.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are fluid collection devices and methods of using fluid collection devices. The fluid collection devices may include a fluid impermeable barrier, a fluid permeable body, and a base that is one or more of moldable, compressible, and/or enlarged relative to the rest of the fluid impermeable barrier. Conventional fluid collection devices sometimes do not effectively secure in the desired position between the legs of the user. For example, in underweight patients and/or patients having less gluteal tissues, the gap between the legs or the buttocks may be significantly wider than a width of a conventional urine collection device, leaving the conventional urine collection device with a high degree of mobility between the legs or buttocks of the patients and increasing the likelihood of the urine collection device moving from the desired positioned.

To improve securement of a urine collection device between the legs of a patient using the urine collection device, embodiments of urine collections systems described herein include an enlarged, moldable, and/or compressible base that results in the technical effect of improved securement of the fluid collection device in a preferred position on the user. As shall be described in greater detail below, the base may provide an increased width and/or compressibility to improve securement of the urine collection device in a desired positioned between the legs or buttocks of the patient using the urine collection device. The base may include one or more of a substantially spherical shape, a conical shape, a frustoconical shape, a pyramid shape, a cylindrical shape, an ovoid shape, a prism shape, a cuboid shape, a diamond shape, a wedge shape, a bulbous shape, a disc shape, or other suitable shapes. The base also may include one or more of a foam or gel material that results in the technical effect of a compressible and/or moldable characteristic to the base.

The fluid collection devices disclosed herein are configured to collect fluids from an individual. The fluids collected by the fluid collection devices may include urine. The fluids collected by the fluid collection devices may also include at least one of vaginal discharge, penile discharge, reproductive fluids, blood, sweat, or other bodily fluids. Fluid collection devices described herein may be used in fluid collection systems. The fluid collection systems may include a fluid collection device, a fluid storage container, and a portable vacuum source, described in greater detail below with FIG. 8. Fluid (e.g., urine or other bodily fluids) collected in the fluid collection device may be removed from the fluid collection device via a conduit which protrudes into an interior region of the fluid collection device. Fluid collection devices described herein may be shaped and sized to be positioned adjacent to the opening of a female urethra or over the urethra of a male having a buried penis.

Figure 1A:
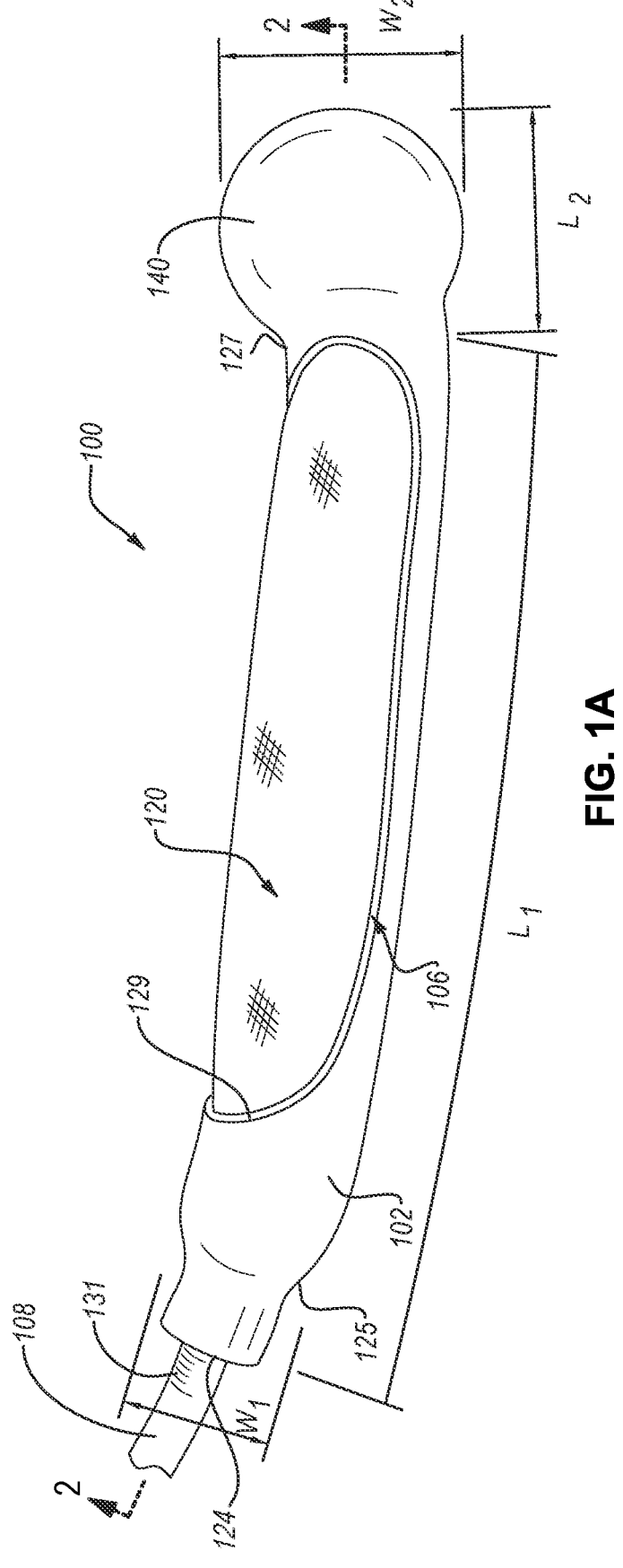
FIG. 1A is an isometric view of a fluid collection device, according to an embodiment.

FIG. 1A is an isometric view of a fluid collection device 100, according to an embodiment. The fluid collection device 100 is an example of a female fluid collection device 100 that is configured to receive fluids from a female or a male having a buried penis. The fluid collection device 100 includes a fluid impermeable barrier 102 having a first end region 125 and a second end region 127, a base 140 secured to or extending from the second end region 127, and a fluid permeable body 120. The fluid impermeable barrier 102 at least partially defines a chamber 104 (e.g., interior region, shown in FIG. 1C) and includes an inward border or edge 129 defining an opening 106. The fluid impermeable barrier 102 may be substantially cylindrical in shape between the first end region 125 and the second end region 127 and/or the base 140. In other embodiments, the fluid impermeable barrier 102 may include other shapes, such as one of more substantially planar surfaces, triangular, or other suitable shape. The opening 106 is formed in and extends longitudinally through the fluid impermeable barrier 102, thereby enabling fluids to enter the chamber 104 from outside of the fluid collection device 100. The opening 106 may be configured to be positioned adjacent to the opening of a female urethra or over the urethra of a male having a buried penis.

The fluid collection device 100 may be positioned at least proximate (e.g., adjacent) to the opening of the female urethra and urine may enter the interior region (e.g., chamber 104) of the fluid collection device 100 via the opening 106. For example, the opening 106 may exhibit an elongated shape that is configured to extend from a first location below the urethral opening (e.g., at or near the anus or the vaginal opening) to a second location above the urethral opening (e.g., at or near the clitoris or the pubic hair). The opening 106 may exhibit an elongated shape since the space between the legs of a female is relatively small when the legs of the female are closed, thereby only permitting the flow of the fluids along a path that corresponds to the elongated shape of the opening 106. For example, the opening 106 may extend longitudinally along the fluid impermeable barrier 102. The opening 106 in the fluid impermeable barrier 102 may exhibit a width that is measured transverse to the longitudinal direction and may be at least about 10% of the circumference of the fluid collection device 100, such as about 25% to about 50%, about 40% to about 60%, about 50% to about 75%, about 65% to about 85%, or about 75% to about 100% of the circumference of the fluid collection device 100. The opening 106 may exhibit a width that is greater than 50% of the circumference of the fluid collection device 100 since the vacuum (e.g., suction) through the conduit 108 pulls the fluid into the conduit 108. In some embodiments, the opening 106 may be vertically oriented (e.g., having a major axis parallel to the longitudinal axis of the device 100). In some embodiments, (not shown), the opening 106 may be horizontally oriented (e.g., having a major axis perpendicular to the longitudinal axis of the device 100). In some embodiments, the inward border or edge 129 of the fluid impermeable barrier 102 defines the opening 106. The edge 129 may include two opposing arced portions, the arc portions following the outer circumference or periphery of the substantially cylindrical fluid impermeable barrier 102. In an embodiment, the fluid impermeable barrier 102 may be configured to be attached to the individual, such as adhesively attached (e.g., with a hydrogel adhesive) to the individual. According to an embodiment, a suitable adhesive is a hydrogel layer, such as those disclosed in U.S. Patent Application Publication No. 2017/0189225, the disclosure of which is incorporated herein by reference in its entirety.

The fluid impermeable barrier 102 may also temporarily store the fluids in the chamber 104. For example, the fluid impermeable barrier 102 may be formed of any suitable fluid impermeable materials, such as a fluid impermeable polymer (e.g., silicone, polypropylene, polyethylene, polyethylene terephthalate, a polycarbonate, etc.), polyurethane films, thermoplastic elastomer (TPE), rubber, thermoplastic polyurethane, another suitable material, or combinations thereof. As such, the fluid impermeable barrier 102 substantially prevents the fluids from exiting the portions of the chamber 104 that are spaced from the opening 106. The fluid impermeable barrier 102 is flexible, thereby enabling the fluid collection device 100 to bend or curve when positioned against the body of a wearer. Example fluid impermeable barriers may include, but are not limited to, a fluid impermeable barrier including at least one of Versaflex CL 2000X TPE, Dynaflex G6713 TPE, or Silpuran 6000/05 A/B silicone.

In an embodiment, the fluid impermeable barrier 102 may be air permeable. In such an embodiment, the fluid impermeable barrier 102 may be formed of a hydrophobic material that defines a plurality of pores. In an embodiment, one or more portions of at least the outer surface of the fluid impermeable barrier 102 may be formed from a soft and/or smooth material, thereby reducing chaffing. The fluid impermeable barrier 102 may include markings thereon, such as one or more markings to aid a user in aligning the device 100 on the wearer. For example, a line on the fluid impermeable barrier 102 (e.g., opposite the opening 106) may allow a healthcare professional to align the opening 106 over the urethra of the wearer. In examples, the markings may include one or more of alignment guide or an orientation indicator, such as a stripe or hashes. Such markings may be positioned to align the device 100 to one or more anatomical features such as a pubic bone, etc.

The fluid impermeable barrier 102 also includes a longitudinal length $L_1$ that may extend approximately from the aperture 124 and/or the first end region 125 to approximately the second end region 127. In some embodiment, the longitudinal length $L_1$ extends from the aperture 124 and/or the first end region 125 to the second end region 127 where the base 140 begins to have a greater lateral width or dimension than the fluid impermeable barrier 102. In some embodiments, the longitudinal length $L_1$ is about 2.5 cm to about 30.5 cm, about 5.1 cm to about 15.2 cm, about 10.2 cm to about 20.3 cm, about 15.2 cm to about 25.4 cm, about 20.3 cm to about 30.5 cm, about 5.1 cm to about 10.2 cm, about 10.2 cm to about 15.2 cm, about 15.2 cm to about 20.3 cm, about 20.3 cm to about 25.4 cm, about 25.4 cm to about 30.5 cm, about 2.5 cm to about 5.1 cm, about 5.1 cm to about 7.6 cm, about 7.6 cm to about 10.2 cm, about 10.2 cm to about 12.7 cm, about 12.7 cm to about 15.2 cm, about 15.2 cm to about 17.8 cm, about 17.8 cm to about 20.3 cm, about 20.3 cm to about 22.9 cm, about 22.9 cm to about 25.4 cm, about 25.4 cm to about 27.9 cm, about 27.9 cm to about 30.5 cm, at least about 10.2 cm, at least about 12.7 cm, at least about 15.2 cm, at least about 17.8 cm, at least about 20.3 cm, at least about 22.9 cm, at least about 25.4 cm, at least about 27.9 cm, at least about 30.5 cm, less than about 30.5 cm, less than about 27.9 cm, less than about 25.4 cm, less than about 22.9 cm, less than about 20.3 cm, less than about 17.8 cm, less than about 15.2 cm, less than about 12.7 cm, or less than about 10.2 cm.

The fluid impermeable barrier 102 also may include a lateral width $W_1$. The lateral width $W_1$ may, for example, be the diameter of the cylinder when the fluid impermeable barrier 102 is formed in a generally cylindrical shape. In other embodiments, the lateral width $W_1$ may include other lateral dimensions, such as a maximum lateral diameter of an ovoid or a maximum lateral width of a cuboid or prism. In some embodiments, the lateral width $W_1$ is about 1.27 cm to about 10.2 cm, about 1.27 cm to about 3.8 cm, about 2.5 cm to about 5.1 cm, about 3.8 cm to about 6.4 cm, about 5.1 cm to about 7.6 cm, about 1.27 cm to about 2.5 cm, about 2.5 cm to about 3.8 cm, about 3.8 cm to about 5.1 cm, about 5.1 cm to about 6.4 cm, about 6.4 cm to about 7.6 cm, about 1.27 cm to about 1.9 cm, about 1.9 cm to about 2.5 cm, about 2.5 cm to about 3.2 cm, about 3.2 cm to about 3.8 cm, about 3.8 cm to about 4.4 cm, about 4.4 cm to about 5.1 cm, about 5.1 cm to about 5.7 cm, about 5.7 cm to about 6.4 cm, about 6.4 cm to about 7 cm, about 7 cm to about 7.6 cm, about 7.6 cm to about 8.3 cm, at least about 1.27 cm, at least about 1.9 cm, at least about 2.5 cm, at least about 3.2 cm, at least about 3.8 cm, at least about 4.4 cm, at least about 5.1 cm, at least about 5.7 cm, at least about 6.4 cm, less than about 10.2 cm, less than about 7.6 cm, less than about 6.4 cm, less than about 5.1 cm, less than about 4.4 cm, less than about 3.8 cm, less than about 3.2 cm, less than about 2.5 cm, or less than about 1.9 cm.

The fluid collection device 100 also includes a base 140 that is secured to and/or extends from the from the second end region 127 of the fluid impermeable barrier 102. The base 140 includes a lateral dimension greater than the lateral dimension of the fluid impermeable barrier 102 effective that results in a technical effect of a more secure fit of the fluid collection device 100 for users (e.g., patients) having less gluteal tissues. For example, conventional fluid collection devices may be too narrow to remain between the buttocks 152 (shown in FIG. 1B) of users 150 having less gluteal tissue. An enlarged base 140 having a lateral dimension greater than the fluid impermeable barrier 102 results in a technical effect of the enlarged base 140 more likely to contact the buttocks 142 and remain in place between the buttocks 142 of users having less gluteal tissues. The base 140 may be formed in a variety of shapes, such as the shape of substantially a sphere, a cuboid, an ovoid, a cone, a pyramid, a frustocone, a cylinder, a diamond, or other three-dimensional shape having a cross-sectional shape of a circle, a triangle, a rectangle, a square, a pentagon, a hexagon, a heptagon, an octagon, and so on. In the fluid collection device 100 shown in FIG. 1A, the base 140 is shaped generally spherical.

The base 140 may include various materials according to different embodiments. In some embodiments, the base 140 includes the same material as the fluid impermeable barrier 102. Accordingly, the base 140 may include any of the materials provided above with reference to the fluid impermeable barrier 102. For example, the base may be integral with the fluid impermeable barrier 102. In some embodiments, the base 140 includes one or more different materials than the fluid impermeable barrier 102. For example, the base 140 may be separate and bonded or otherwise secured to the fluid impermeable barrier. In some embodiments, the base 140 includes a compressible material, such as a foam material. The foam material may include a closed cell foam, such as a polyurethane closed cell foam. In some embodiments, the base 140 may be moldable and, accordingly, may include a moldable material. For example, the base 140 may include a gel material, such as a silicone gel. In some embodiments, the base 140 may include an outer layer and be filled with a gel material.

The base 140 may include a continuous, constant material throughout the base 140. For example, the base 140 may include a continuous, constant material similar or the same as the fluid impermeable barrier 102. In some examples, the base 140 may include a continuous, constant foam material. The base 140 also may include an outer layer that is different than the material (or air) housed within the base. For example, the base 140 may include an outer layer that is similar or the same as the fluid impermeable barrier 102 and an inner portion that is filled with air (either in fluid communication with the reservoir 122 or divided from the reservoir 122), a gel material, a foam material, or any combination thereof. In some embodiments, the base 140 may include an outer layer of a foam material and an inner portion that is filled with air (either in fluid communication with the reservoir 122 or divided from the reservoir 122), a gel material, a different foam material from the outer layer, or any combination thereof. In some embodiments, the base 140 may include an outer layer, a foam or gel material layer, and an inner portion different from the foam or gel material layer.

In many embodiments, the base 140 includes a lower hardness than fluid impermeable barriers of conventional fluid collection devices and/or the fluid impermeable barrier. A lower hardness of the base 140 results in a technical effect of improved securement of the base 140 to the skin of the user. The base 140 may include silicone, thermoplastic elastomer, rubber, thermoplastic polyurethane, or combinations thereof to provide the lower hardness described herein. Hardness of the base 140 may include one or more of a shore A durometer hardness according to different embodiments. For example, the base 140 may include a shore A durometer hardness of about 1 to about 30, about 2 to about 25, about 5 to about 20, about 1 to about 5, about 5 to about 10, about 10 to about 15, about 15 to about 20, about 20 to about 25, about 25 to about 30, about 1 to about 3, about 3 to about 5, about 5 to about 7, about 7 to about 9, about 9 to about 11, about 11 to about 13, about 13 to about 15, about 15 to about 17, about 17 to about 19, about 19 to about 21, about 21 to about 23, about 23 to about 25, about 25 to about 27, about 27 to about 29, about 2, about 4, about 5, about 6, about 7, about 8, about 9, about 10, about 11, about 12, about 13, about 14, about 15, about 16, about 17, about 18, about 19, about 20, about 22, about 24, about 26, about 28, about 30, less than about 30, less than about 25, less than about 20, less than about 17.5, less than about 15, less than about 12.5, less than about 10, less than about 8, less than about 7, less than about 6, or less than about 5. In some examples, the base 140 may include Dynaflex G6713 TPE having a shore A durometer of about 14, or Silpuran 6000/05 A/B silicone having a shore A durometer hardness of about 5.

The base 140 also may include a lateral dimension, such as a lateral width $W_2$. On the base 140 of the fluid collection device 100, the lateral width $W_2$ is a diameter of the spherical base 140. The lateral width $W_2$ is greater than the lateral width $W_1$ of the fluid impermeable barrier 102. The base 140 having a diameter or other lateral dimension greater than the lateral dimension of the fluid impermeable barrier 102 results in a technical effect of a more secure fit of the fluid collection device 100 for users having less gluteal tissues. For example, conventional fluid collection devices may be too narrow to remain between the buttocks of patients having less gluteal tissue. An enlarged base having a diameter or other lateral dimension greater than the fluid impermeable barrier allows the enlarged base to contact the buttocks and remain in place between the buttocks of patients having less gluteal tissues.

The lateral width $W_2$ may be at least about 2.5 cm, at least about 3.2 cm, at least about 3.8 cm, at least about 5.1 cm, at least about 5.7 cm, at least about 6.4 cm, at least about 7 cm, at least about 7.6 cm, at least about 3.25 at least about 8.9 cm, at least about 9.5 cm, at least about 10.2 cm, about 2.5 cm to about 12.7 cm, about 3.2 cm to about 7.6 cm, about 7.6 cm to about 12.7 cm, about 3.8 cm to about 5.1 cm, about 5.1 cm to about 6.4 cm, about 6.4 cm to about 7.6 cm, about 7.6 cm to about 8.9 cm, about 8.9 cm to about 10.2 cm, 10.2 cm to about 12.7 cm, about 3.2 cm, about 3.8 cm, about 4.4 cm, about 5.1 cm, about 5.7 cm, about 6.4 cm, about 7 cm, about 7.6 cm, about 3.25 about 8.9 cm, about 9.5 cm, or about 10.2 cm. The lateral width $W_2$ may be at least 1.25 times greater than the lateral width $W_1$, at least 1.5 times greater than the lateral width $W_1$, at least 1.75 times greater than the lateral width $W_1$, at least 2 times greater than the lateral width $W_1$, at least 2.25 times greater than the lateral width $W_1$, at least 2.5 times greater than the lateral width $W_1$, at least 2.75 times greater than the lateral width $W_1$, at least 3 times greater than the lateral width $W_1$, about 1.05 to about 1.25 times greater than the lateral width $W_1$, about 1.25 to about 1.5 times greater than the lateral width $W_1$, about 1.5 to about 1.75 times greater than the lateral width $W_1$, about 1.75 to about 2 times greater than the lateral width $W_1$, about 2 to about 2.25 times greater than the lateral width $W_1$, about 2.25 to about 2.5 times greater than the lateral width $W_1$, about 2.5 to about 2.75 times greater than the lateral width $W_1$, or about 2.75 to about 3 times greater than the lateral width $W_1$.

The base 140 also may include a longitudinal dimension, such as a longitudinal length $L_2$. The longitudinal length $L_2$ may be measured from where the lateral width $W_2$ is greater than lateral width $W_1$ of the fluid impermeable barrier 102 to where the base 140 terminates or ends. On the base 140 of the fluid collection device 100, the longitudinal length $L_2$ is approximately the diameter of the spherical base 140 and may be substantially equal to the lateral width $W_2$. In other embodiments, the longitudinal length $L_2$ may be less than or greater than the lateral width $W_2$.

The longitudinal length $L_2$ may be at least about 2.5 cm, at least about 3.2 cm, at least about 3.8 cm, at least about 5.1 cm, at least about 5.7 cm, at least about 6.4 cm, at least about 7 cm, at least about 7.6 cm, at least about 3.25 at least about 8.9 cm, at least about 9.5 cm, at least about 10.2 cm, about 2.5 cm to about 12.7 cm, about 3.2 cm to about 7.6 cm, about 7.6 cm to about 12.7 cm, about 3.8 cm to about 5.1 cm, about 5.1 cm to about 6.4 cm, about 6.4 cm to about 7.6 cm, about 7.6 cm to about 8.9 cm, about 8.9 cm to about 10.2 cm, about 10.2 cm to about 12.7 cm, about 3.2 cm, about 3.8 cm, about 4.4 cm, about 5.1 cm, about 5.7 cm, about 6.4 cm, about 7 cm, about 7.6 cm, about 3.25 about 8.9 cm, about 9.5 cm, or about 10.2 cm. The longitudinal length $L_2$ may be at least 1.25 times greater than the lateral width $W_1$, at least 1.5 times greater than the lateral width $W_1$, at least 1.75 times greater than the lateral width $W_1$, at least 2 times greater than the lateral width $W_1$, at least 2.25 times greater than the lateral width $W_1$, at least 2.5 times greater than the lateral width $W_1$, at least 2.75 times greater than the lateral width $W_1$, at least 3 times greater than the lateral width $W_1$, about 1.05 to about 1.25 times greater than the lateral width $W_1$, about 1.25 to about 1.5 times greater than the lateral width $W_1$, about 1.5 to about 1.75 times greater than the lateral width $W_1$, about 1.75 to about 2 times greater than the lateral width $W_1$, about 2 to about 2.25 times greater than the lateral width $W_1$, about 2.25 to about 2.5 times greater than the lateral width $W_1$, about 2.5 to about 2.75 times greater than the lateral width $W_1$, or about 2.75 to about 3 times greater than the lateral width $W_1$.

The base 140 also may include a height measured generally perpendicularly to the longitudinal length $L_2$ and the lateral width $W_2$. On the base 140 of the fluid collection device 100, the height is approximately the diameter of the spherical base 140 and may be substantially equal to the lateral width $W_2$ and the longitudinal length $L_2$. In other embodiments, the height may be less than or greater than at least one of the lateral width $W_2$ or the longitudinal length $L_2$.

The height of the base 140 may be at least about 2.5 cm, at least about 3.2 cm, at least about 3.8 cm, at least about 5.1 cm, at least about 5.7 cm, at least about 6.4 cm, at least about 7 cm, at least about 7.6 cm, at least about 3.25 at least about 8.9 cm, at least about 9.5 cm, at least about 10.2 cm, about 2.5 cm to about 12.7 cm, about 3.2 cm to about 7.6 cm, about 7.6 cm to about 12.7 cm, about 3.8 cm to about 5.1 cm, about 5.1 cm to about 6.4 cm, about 6.4 cm to about 7.6 cm, about 7.6 cm to about 8.9 cm, about 8.9 cm to about 10.2 cm, 10.2 cm to about 12.7 cm, about 3.2 cm, about 3.8 cm, about 4.4 cm, about 5.1 cm, about 5.7 cm, about 6.4 cm, about 7 cm, about 7.6 cm, about 3.25 about 8.9 cm, about 9.5 cm, or about 10.2 cm. The height of the base 140 may be at least 1.25 times greater than a height of the fluid impermeable barrier 102, at least 1.5 times greater than the height of the fluid impermeable barrier 102, at least 1.75 times greater than the height of the fluid impermeable barrier 102, at least 2 times greater than the height of the fluid impermeable barrier 102, at least 2.25 times greater than the height of the fluid impermeable barrier 102, at least 2.5 times greater than the height of the fluid impermeable barrier 102, at least 2.75 times greater than the height of the fluid impermeable barrier 102, at least 3 times greater than the height of the fluid impermeable barrier 102, about 1.05 to about 1.25 times greater than the height of the fluid impermeable barrier 102, about 1.25 to about 1.5 times greater than the height of the fluid impermeable barrier 102, about 1.5 to about 1.75 times greater than the height of the fluid impermeable barrier 102, about 1.75 to about 2 times greater than the height of the fluid impermeable barrier 102, about 2 to about 2.25 times greater than the height of the fluid impermeable barrier 102, about 2.25 to about 2.5 times greater than the height of the fluid impermeable barrier 102, about 2.5 to about 2.75 times greater than the height of the fluid impermeable barrier 102, or about 2.75 to about 3 times greater than the height of the fluid impermeable barrier 102.

In some embodiments, the base 140 may be oriented such that the cylindrical fluid impermeable barrier 102 is generally centered relative to the periphery of the base 140. In some embodiments, the cylindrical portion of the fluid impermeable barrier 102 may be misaligned with a center of the base 140, or the cylindrical portion of the fluid impermeable barrier 102 may not be centrally aligned with a center of the base 140. For example, a rear surface of the cylindrical portion of the fluid impermeable barrier 102 distal to the opening 106 may be generally aligned with or proximate to a rear surface of the base 140. In some embodiments, an upper surface of the cylindrical portion of the fluid impermeable barrier 102 may be generally aligned with or proximate to an upper surface of the base 140.

In some embodiments, the base 140 of the fluid collection device 100 may not be enlarged relative to the fluid impermeable barrier 102, but the base 140 may include a material different than the material of the fluid impermeable barrier 102. For example, the base 140 include a lateral width $W_2$ substantially equal to the lateral width $W_1$ of the fluid impermeable barrier 102, but the base 140 may include a foam material, a gel material, a material having a lower hardness than the fluid impermeable barriers 102, or combinations thereof.

The fluid collection device 100 may include a fluid permeable body 120 or layer disposed in the chamber 104. The fluid permeable body 120 may cover or extend across at least a portion (e.g., all) of the opening 106. The fluid permeable body 120 may be configured to wick any fluid away from the opening 106, thereby preventing the fluid from escaping the chamber 104. The fluid permeable body 120 also may wick the fluid generally towards an interior of the chamber 104. A portion of the fluid permeable body 120 may define a portion of an outer surface of the fluid collection device 100. Specifically, the portion of the fluid permeable body 120 defining the portion of the outer surface of the fluid collection device 100 may be the portion of the fluid permeable body 120 exposed by the opening 106 defined by the fluid impermeable barrier 102 that contacts the user. Moreover, the portion of the fluid permeable device defining the portion of the outer surface of the fluid collection device 100 may be free from coverage by gauze or other wicking material at the opening.

The fluid permeable body 120 may include any material that may wick the fluid. The permeable properties referred to herein may be wicking, capillary action, diffusion, or other similar properties or processes, and are referred to herein as "permeable" and/or "wicking." Such "wicking" may exclude absorption into the wicking material. The fluid permeable body 120 may include a one-way fluid movement fabric. As such, the fluid permeable body 120 may remove fluid from the area around the female urethra, thereby leaving the urethra dry. The fluid permeable body 120 may enable the fluid to flow generally towards a reservoir 122 (shown in FIGS. 2A and 2B) of void space formed within the chamber 104. For example, the fluid permeable body 120 may include a porous or fibrous material, such as hydrophilic polyolefin. In some embodiments, the fluid permeable body 120 consists of or consists essentially of a porous or fibrous material, such as hydrophilic polyolefin. Examples of polyolefin that may be used in the fluid permeable body 120 include, but are not limited to, polyethylene, polypropylene, polyisobutylene, ethylene propylene rubber, ethylene propylene diene monomer, or combinations thereof. The porous or fibrous material may be extruded into a substantially cylindrically shape to fit within the chamber 104 of the fluid impermeable barrier 102. The fluid permeable body 120 may include varying densities or dimensions. Moreover, the fluid permeable body 120 may be manufactured according to various manufacturing methods, such as molding, extrusion, or sintering.

In some embodiments, the fluid permeable body 120 includes a singular and porous body. That is, during use, the fluid permeable body 120 extends from the conduit 108 to interface the fluid impermeable barrier 102 and the opening 106. In some embodiments, a majority of the outer surface 109 (shown in FIG. 1C) of the fluid permeable body 120 interfaces with an inner surface 103 (shown in FIG. 1C) of the fluid impermeable barrier 106. A singular fluid permeable body 120 may be advantageous to conventional systems, which typically require an air-laid nonwoven pad covered by a ribbed fabric compression bandage, because a singular fluid permeable body 120 reduced the number of components in the fluid collection device 100, reduces the assembly time of the fluid collection device 100, requires shelf-life data for only a single component, and provides a latex-free single component. In some embodiments, at least a portion of the singular porous material of the fluid permeable body 120 extends continuously between the opening 106 and the reservoir 122 to wick any fluid from the opening 106 directly to the reservoir 122. Moreover, as the fluid impermeable barrier 102 is flexible and the fluid permeable body 120 is configured to wick fluid from the body rather than absorb fluid from the body and hold the fluid against the body, the fluid collection device 100, in some embodiments, is free from a seal or cushioning ring on the inward edge 129 defining the opening 106. In these and other embodiments, the fluid permeable body 120 includes an outer surface and a single layer or type of material between the opening 106 and the conduit 108 positioned within the fluid permeable body 120.

In other embodiments, the fluid permeable body 120 may include two or more layers of fluid permeable materials and include no (or an absence of) more than two layers of material between the opening 106 and the conduit 108 positioned within the fluid permeable body 120. For example, the fluid collection device 100 may include a fluid permeable membrane covering or wrapping around at least a portion of a fluid permeable body, with both the fluid permeable membrane and the fluid permeable body being disposed in the chamber 104. The fluid permeable membrane may cover or extend across at least a portion (e.g., all) of the opening 106. The fluid permeable membrane may be configured to wick any fluid away from the opening 106, thereby preventing the fluid from escaping the chamber 104. The permeable properties referred to herein may be wicking, capillary action, diffusion, or other similar properties or processes, and are referred to herein as "permeable" and/or "wicking." In some embodiments, at least one of the fluid permeable membrane or the fluid permeable support include nylon configured to wick fluid away from the opening 106. The material of the fluid permeable membrane and the fluid permeable support also may include natural fibers. In such examples, the material may have a coating to prevent or limit absorption of fluid into the material, such as a water repellent coating. Such "wicking" may not include absorption into the wicking material. Put another way, substantially no absorption of fluid into the material may take place after the material is exposed to the fluid and removed from the fluid for a time. While no absorption is desired, the term "substantially no absorption" may allow for nominal amounts of absorption of fluid into the wicking material (e.g., absorbency), such as about 30 wt % of the dry weight of the wicking material, about 20 wt %, about 10 wt %, about 7 wt %, about 5 wt %, about 3 wt %, about 2 wt %, about 1 wt %, or about 0.5 wt % of the dry weight of the wicking material.

The fluid permeable membrane may also wick the fluid generally towards an interior of the chamber 104, as discussed in more detail below. The fluid permeable membrane may include any material that may wick the fluid. For example, the fluid permeable membrane may include fabric, such as a gauze (e.g., a silk, linen, polymer based materials such as polyester, or cotton gauze), another soft fabric (e.g., jersey knit fabric or the like), or another smooth fabric (e.g., rayon, satin, or the like). Forming the fluid permeable membrane from gauze, soft fabric, and/or smooth fabric may reduce chaffing caused by the fluid collection device 100. Other embodiments of fluid permeable membranes, fluid permeable supports, chambers, and their shapes and configurations are disclosed in U.S. patent application Ser. No. 15/612,325 filed on Jun. 2, 2017; U.S. patent application Ser. No. 15/260,103 filed on Sep. 8, 2016; U.S. patent application Ser. No. 15/611,587 filed on Jun. 1, 2017; PCT Patent Application No. PCT/US19/29608, filed on Apr. 29, 2019, the disclosure of each of which is incorporated herein, in its entirety, by this reference. In many embodiments, the fluid permeable body 120 includes a fluid permeable support including a porous nylon structure (e.g., spun nylon fibers) and a fluid permeable membrane including gauze about or over the porous nylon structure.

Figure 1B:
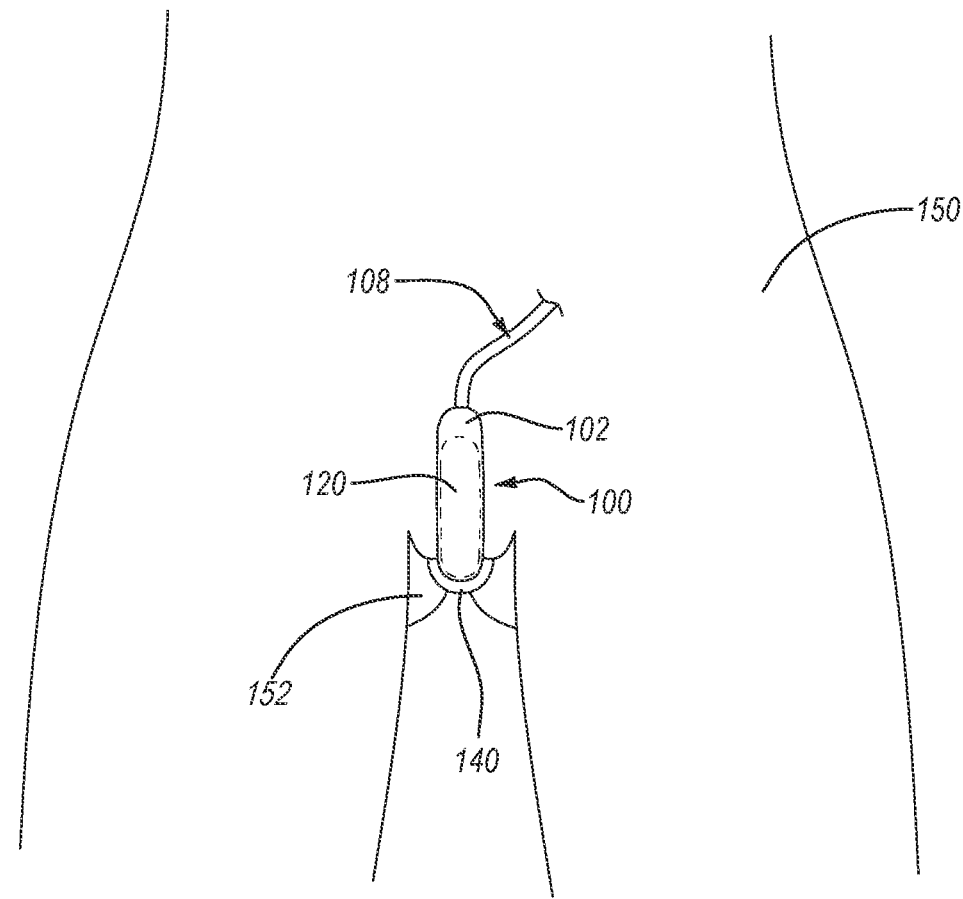
FIG. 1B is a front view of the fluid collection device of FIG. 1A worn on a female user.
Figure 1C:
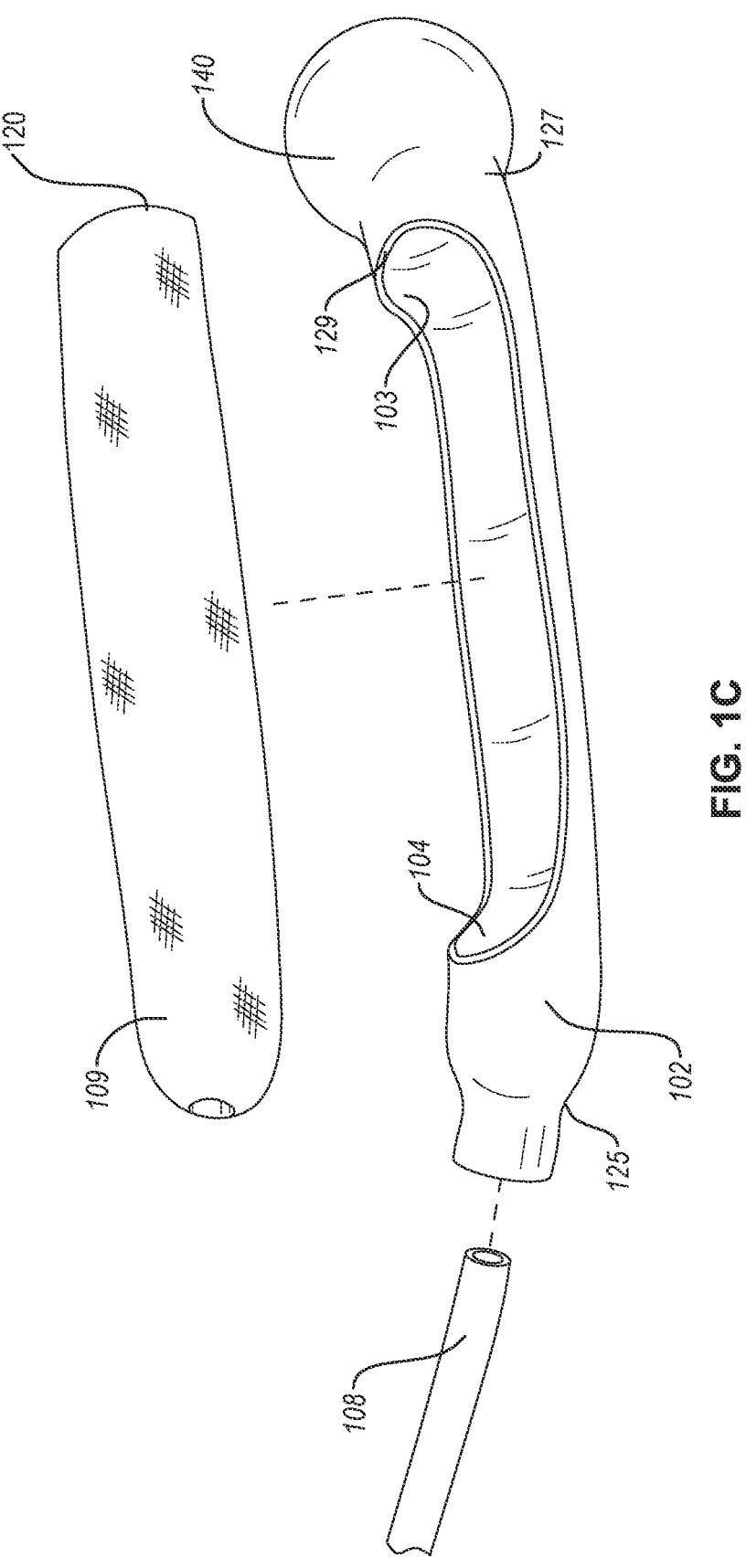
FIG. 1C is an exploded view of the fluid collection device of FIG. 1A.

FIG. 1B is a front view of a fluid collection device 100 in use on a female user 150. In use, the fluid permeable body 120 of the fluid collection device 100 is positioned adjacent to a urethra of the user 150 and the base 140 of the fluid collection device 100 is between the buttocks 152 of the user 150. The fluid permeable body 120 is disposed within a chamber 104 (shown in FIGS. 2A and 2B) of the fluid impermeable barrier 102 of the fluid collection device 100 and is exposed to the urethra of the user 150 through the opening 106 in the fluid collection device 100. The fluid collection device 100 may be secured to the user with any of a number of securing devices. Fluids received in the chamber 104 of the fluid collection device 100 from the urethra may be removed through the conduit 108.

Figure 2A:
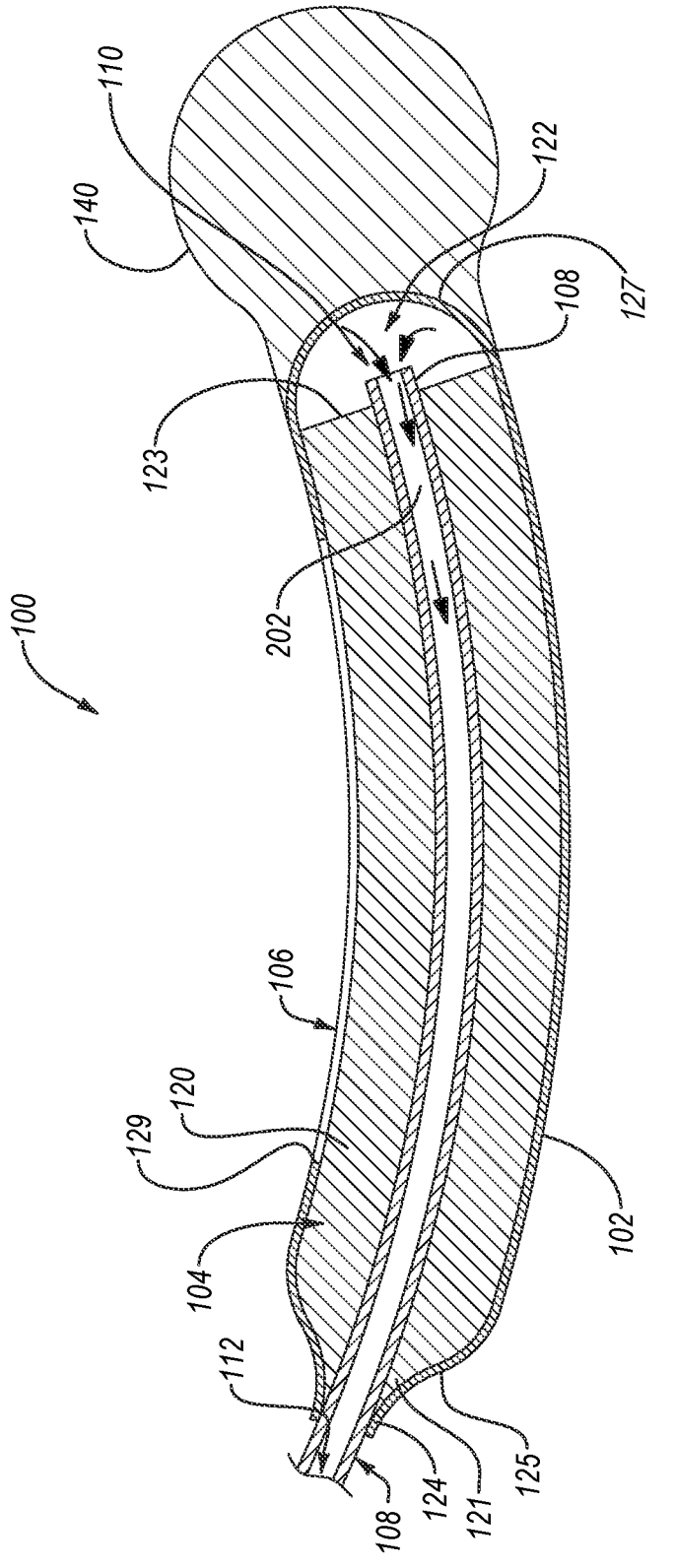
FIGS. 2A and 2B are cross-sectional views of the fluid collection device of FIG. 1A taken along line 2-2 thereof, according to various embodiments.

FIG. 2A is a cross-sectional view of the fluid collection device 100 taken along line 2-2 of FIG. 1A. The fluid collection device 100 also includes conduit 108 that is at least partially disposed in the chamber 104. The conduit 108 (e.g., a tube) includes an inlet 110 at a second end region 127 of the fluid impermeable barrier 102 and an outlet 112 at a first end region 125 of the fluid impermeable barrier 102 positioned downstream from the inlet 110. The conduit 108 provides fluid communication between an interior region of the chamber 104 and a fluid storage container (not shown) or a portable vacuum source (not shown). For example, the conduit 108 may directly or indirectly fluidly couple the interior region of the chamber 104 and/or the reservoir 122 with the fluid storage container or the portable vacuum source.

In the illustrated embodiment, the fluid permeable body 120 defines a bore 202 extending through the fluid permeable body 120 from a first body end 121 of the fluid permeable body 120 to a second body end 123 of the fluid permeable body 120 distal to the first body end 120. In other embodiments, the bore 202 extends only partially into the fluid permeable body from the first body end 121 of the fluid permeable body 120.

In the illustrated embodiment, the conduit 108 is at least partially disposed in the chamber 104 and interfaces at least a portion of the bore 202 of the fluid permeable body 120. For example, the conduit 108 may extend into the fluid impermeable barrier 102 from the first end region 125 (e.g., proximate to the outlet 112) and may extend through the bore 202 to the second end region 127 (e.g., opposite the first end region 125) to a point proximate to the reservoir 122 such that the inlet 110 is in fluid communication with the reservoir 122. For example, in the illustrated embodiment, the inlet 110 is positioned in the reservoir 122. However, in other embodiments, the inlet 110 may be positioned flush with or behind an end of the fluid permeable body 120 that partially defines the reservoir 122. The fluid collected in the fluid collection device 100 may be removed from the interior region of the chamber 104 via the conduit 108. The conduit 108 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some embodiments, the conduit 108 may include silicone or latex.

The fluid impermeable barrier 102 may store fluids in the reservoir 122 therein. The reservoir 122 is an unoccupied portion of the chamber 104 and is void of other material. In some embodiments, the reservoir 122 is defined at least partially by the fluid permeable body 120 and the fluid impermeable barrier 102. For example, in an embodiment, the reservoir 122 may be located at the portion of the chamber 104 that is closest to the inlet 110 (e.g., the second end region). Accordingly, in the embodiment in FIG. 2A, the reservoir 122 is defined by the second body end 123 of the fluid permeable body 120 and the second end region 127 of the fluid impermeable barrier 102. Moreover, in the fluid collection device 100 shown in FIG. 2A, the reservoir 122 is generally not positioned within the base 140 (e.g., the reservoir 122 is absent from the base 140). As shown in FIG. 2A, the second end region 127 of the fluid impermeable barrier 102 separates the reservoir 122 from the material of the base 140. In other embodiments, however, the reservoir 122 may be at least partially positioned within the base 140. In some embodiments, the material of the base 140 defines at least a portion of the reservoir 122.

The reservoir 122 also may be located at different locations in the chamber 104. For example, the reservoir 122 may be located at the end of the chamber 104 that is closest to the outlet 112. In these and other embodiments, the conduit 108 may extend through the first end region 125 of the fluid impermeable barrier 102 and to the reservoir 122 without extending through the fluid permeable body 120. Accordingly, in these and other embodiments, the fluid permeable body 120 may be free from the bore. In another embodiment, the fluid collection device 100 may include multiple reservoirs, such as a first reservoir that is located at the portion of the chamber of the chamber 104 that is closest to the inlet 110 (e.g., second end region) and a second reservoir that is located at the portion of the of the chamber 104 that is closest to the outlet 112 (e.g., first end region). In another example, the fluid permeable body 120 is spaced from at least a portion of the conduit 108 and the reservoir 122 may be the space between the fluid permeable body 120 and the conduit 108. Other embodiments of reservoirs, fluid impermeable barriers, fluid permeable membranes, fluid permeable bodies, chambers, and their shapes and configurations are disclosed in U.S. patent application Ser. No. 15/612,325 filed on Jun. 2, 2017; U.S. patent application Ser. No. 15/260,103 filed on Sep. 8, 2016; and U.S. patent application Ser. No. 15/611,587 filed on Jun. 1, 2017, the disclosure of each of which is incorporated herein, in its entirety, by this reference.

The fluid impermeable barrier 102 and the fluid permeable body 120 may be configured to have the conduit 108 at least partially disposed in the chamber 104. For example, the fluid permeable body 120 may be configured to form a space that accommodates the conduit 108, such as the bore 202. In another example, the fluid impermeable barrier 102 may define an aperture 124 sized to receive the conduit 108 (e.g., at least one tube). The at least one conduit 108 may be disposed in the chamber 104 via the aperture 124. The aperture 124 may be configured to form an at least substantially fluid tight seal against the conduit 108 or the at least one tube thereby substantially preventing the fluids from escaping the chamber 104.

Figure 2B:
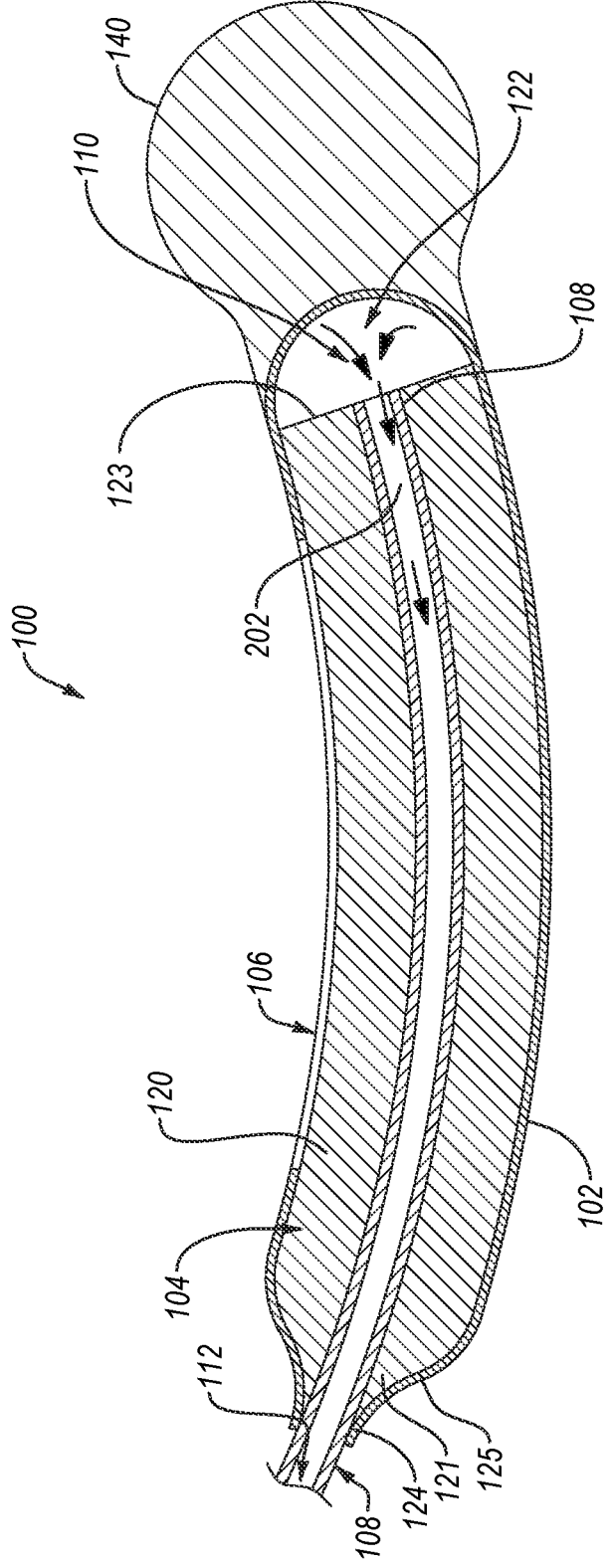

In some embodiments, the conduit 108 may extend through the fluid permeable body 120 and at least partially into the reservoir 122, as shown in FIG. 2A. In some embodiments, the conduit 108 may extend through the fluid permeable body 120 and terminate at or before the second body end 123 of the fluid permeable body 120 such that the conduit 108 does not extend into the reservoir 122 (or the reservoir 122 is absent of the conduit 108). For example, as shown in FIG. 2B, an end of the conduit 108 may be generally flush or coplanar with the second body end 123 of the fluid permeable body 120. In other embodiments, the end of the conduit 108 may be recessed from the second body end 123 of the fluid permeable body 120. The end of the conduit 108 also may be selectively moveable between partially extending into the reservoir 122 (shown in FIG. 2A) and recessed from or flush with the second body end 123 of the fluid permeable body (shown in FIG. 2B).

When secured to the fluid collection device 100, the conduit 108 is configured to provide fluid communication with and at least partially extend between one or more of a fluid storage container (not shown) and a portable vacuum source (not shown). For example, the conduit 108 may be configured to be fluidly coupled to and at least partially extend between one or more of the fluid storage containers and the portable vacuum source. In an embodiment, the conduit 108 is configured to be directly connected to the portable vacuum source (not shown). In such an example, the conduit 108 may extend from the fluid impermeable barrier 102 by at least one foot, at least two feet, at least three feet, or at least six feet. In another example, the conduit 108 is configured to be indirectly connected to at least one of the fluid storage container (not shown) or the portable vacuum source (not shown). In some examples, the conduit may be frosted or opaque (e.g., black) to obscure visibility of the fluids therein. In some embodiments, the conduit is secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The inlet 110 and the outlet 112 are configured to provide fluid communication (e.g., directly or indirectly) between the portable vacuum source (not shown) and the chamber 104 (e.g., the reservoir 122). For example, the inlet 110 and the outlet 112 of the conduit 108 may be configured to directly or indirectly fluidly couple the portable vacuum source to the reservoir 122. In an embodiment, the inlet 110 and/or the outlet 112 may form a male connector. In another example, the inlet 110 and/or the outlet 112 may form a female connector. In an embodiment, the inlet 110 and/or the outlet 112 may include ribs that are configured to facilitate secure couplings. In an embodiment, the inlet 110 and/or the outlet 112 may form a tapered shape. In an embodiment, the inlet 110 and/or the outlet 112 may include a rigid or flexible material.

Locating the inlet 110 at or near a gravimetrically low point of the chamber 104 enables the conduit to receive more of the fluids than if inlet 110 was located elsewhere and reduce the likelihood of pooling (e.g., pooling of the fluids may cause microbe growth and foul odors). For instance, the fluids in the fluid permeable body 120 may flow in any direction due to capillary forces. However, the fluids may exhibit a preference to flow in the direction of gravity, especially when at least a portion of the fluid permeable body 120 is saturated with the fluids.

As the portable vacuum source applies a vacuum/suction in the conduit 108, the fluid(s) in the chamber 104 (e.g., such as in the reservoir 122 positioned at the first end region 125, the second end region 127, or other intermediary positions within the chamber 104) may be drawn into the inlet 110 and out of the fluid collection device 100 via the conduit 108.

In an embodiment, the conduit 108 is configured to be at least insertable into the chamber 104. In such an embodiment, the conduit 108 may include one or more markers 131 (shown in FIG. 1A) on an exterior thereof that are configured to facilitate insertion of the conduit 108 into the chamber 104. For example, the conduit 108 may include one or more markings thereon that are configured to prevent over or under insertion of the conduit 108, such as when the conduit 108 defines an inlet 110 that is configured to be disposed in or adjacent to the reservoir 122. In another embodiment, the conduit 108 may include one or more markings thereon that are configured to facilitate correct rotation of the conduit 108 relative to the chamber 104. In an embodiment, the one or more markings may include a line, a dot, a sticker, or any other suitable marking. In examples, the conduit 108 may extend into the fluid impermeable barrier 102 from the first end region (e.g., proximate to the outlet 112) and may extend to the second end region (e.g., opposite the first end region) to a point proximate to the reservoir 122 such that the inlet 110 is in fluid communication with the reservoir 122. In some embodiments (not shown), the conduit 108 may enter the second end region and the inlet 110 may be disposed in the second end region (e.g., in the reservoir 122). The fluid collected in the fluid collection device 100 may be removed from the interior region of the chamber 104 via the conduit 108. The conduit 108 may include a flexible material such as plastic tubing (e.g., medical tubing) as disclosed herein. In some examples, the conduit 108 may include one or more portions that are resilient, such as having one or more of a diameter or wall thickness that allows the conduit to be flexible.

In an embodiment, one or more components of the fluid collection device 100 may include an antimicrobial material, such as an antibacterial material where the fluid collection device may contact the wearer or the bodily fluid of the wearer. The antimicrobial material may include an antimicrobial coating, such as a nitrofurazone or silver coating. The antimicrobial material may inhibit microbial growth, such as microbial growth due to pooling or stagnation of the fluids. In an embodiment, one or more components of the fluid collection device 100 (e.g., impermeable barrier 102, conduit 108, etc.) may include an odor blocking or absorbing material such as a cyclodextrine containing material or a thermoplastic elastomer (TPE) polymer.

In any of the embodiments disclosed herein, the conduits 108 may include or be operably coupled to a flow meter (not shown) to measure the flow of fluids therein, one or more securement devices (e.g., a StatLock securement device, not shown) or fittings to secure the conduit 108 to one or more components of the systems or devices disclosed herein (e.g., portable vacuum source or fluid storage container), or one or more valves to control the flow of fluids in the systems and devices herein. In an embodiment, at least one of portion of the conduit 108 of the fluid collection devices or systems herein may be formed of an at least partially opaque material which may obscure the fluids that are present therein. For example, a first section of the conduit 108 disclosed herein may be formed of an opaque material or translucent material while a second section of the conduit 108 may be formed of a transparent material or translucent material. In some embodiments, the first section may include transparent or translucent material. Unlike the opaque or nearly opaque material, the translucent material allows a user of the devices and systems herein to visually identify fluids or issues that are inhibiting the flow of fluids within the conduit 108.

In any of the examples, systems or devices disclosed herein, the system of fluid collection device may include moisture sensors (not shown) disposed inside of the chamber of the fluid collection device. In such examples, the moisture sensor may be operably coupled to a controller or directly to the portable vacuum source, and may provide electrical signals indicating that moisture is or is not detected in one or more portions of the chamber. The moisture sensor(s) may provide an indication that moisture is present, and responsive thereto, the controller or portable vacuum device may direct the initiation of suction to the chamber to remove the fluid therefrom. Suitable moisture sensors may include capacitance sensors, volumetric sensors, potential sensors, resistance sensors, frequency domain reflectometry sensors, time domain reflectometry sensors, or any other suitable moisture sensor. In practice, the moisture sensors may detect moisture in the chamber and may provide a signal to the controller or portable vacuum source to activate the portable suction device.

Figure 3A:
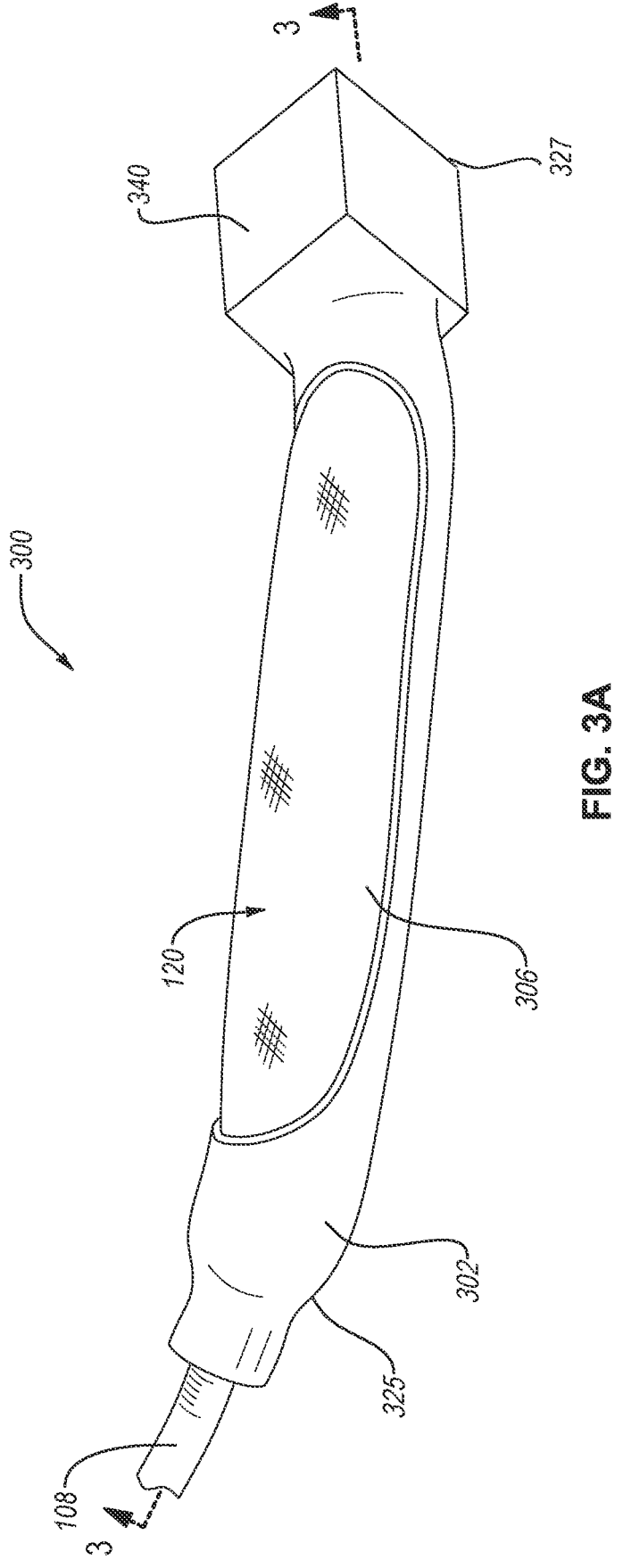
FIG. 3A is an isometric view of a fluid collection device, according to an embodiment.

FIG. 3A is an isometric view of a fluid collection device 300. Unless otherwise noted, the fluid collection device 300 may include any aspect and any technical effect of the fluid collection device 100 described above. For example, the fluid collection device 300 includes a conduit 108 and a fluid permeable body 120 that may include any aspects of the conduit 108 and the fluid permeable body 120 described above in relation to the fluid collection device 100. The fluid collection device 300 also includes a fluid impermeable barrier 302. Unless otherwise noted, the fluid impermeable barrier 302 may include any aspect of the fluid impermeable barrier 102, such as an aperture 124 and a chamber 104. The fluid impermeable barrier 302 also includes a first end region 325 similar to the first end region 125 of the fluid collection device 100 and an opening 306 similar to the opening 106 defined by the fluid impermeable barrier 302.

The fluid collection device 300 also includes an enlarged base 340 having a generally cuboid shape. In the fluid collection device 300, the base 340 forms the second end region 327 of the fluid impermeable barrier 302. Accordingly, the base 340 may include the same or similar material as the fluid impermeable barrier 302, such as any of the materials described above in relation to the fluid impermeable barrier 102. In some embodiments, the base 340 may be secured to or extend from a second end region of the fluid impermeable barrier 302, similar to the base 140 of the fluid collection device 100. Accordingly, in some embodiments, the base 340 may include materials different from the fluid impermeable barrier 302, including any of the materials provided above in relation to the base 140 (such as a foam or a gel material).

The base 340 may include a longitudinal dimension or length similar or equal to any of the longitudinal lengths $L_2$ described above in relation to the base 140. The base 340 may include a lateral dimension or width similar or equal to any of the lateral widths $W_2$ described above in relation to the base 140. The base 340 may include a height similar or equal to any of heights described above in relation to the base 140.

The base 340 may include various orientations with respect to the remainder of the fluid impermeable barrier 302 and the opening 306. For example, the base 340 may be oriented such that an edge or corner of the cuboid base 340 is generally centered between elongated edges of the fluid impermeable barrier 302 defining the opening 306. The base 340, then, may form a peaked edge rising from the fluid impermeable barrier 302 that is centered between elongated edges of the fluid impermeable barrier 302 and positioned to extend between and complement the buttocks of the user. In some embodiments, the base 340 may be oriented such that the opening 306 is generally centered or positioned between two adjacent edges or corners of the base 340. The cylindrical portion of the fluid impermeable barrier 302 may be generally centered relative to the cuboid base 340. In some embodiments, the cylindrical portion of the fluid impermeable barrier 302 may be misaligned with a center of the cuboid base 340, or the cylindrical portion of the fluid impermeable barrier 302 may not be centrally aligned with the cuboid base 340. For example, a rear surface of the cylindrical portion of the fluid impermeable barrier 302 distal to the opening 306 may be generally aligned with or proximate to a rear surface of the base 340. In some embodiments, an upper surface of the cylindrical portion of the fluid impermeable barrier may be generally aligned with or proximate to an upper surface of the base 340.

Figure 3B:
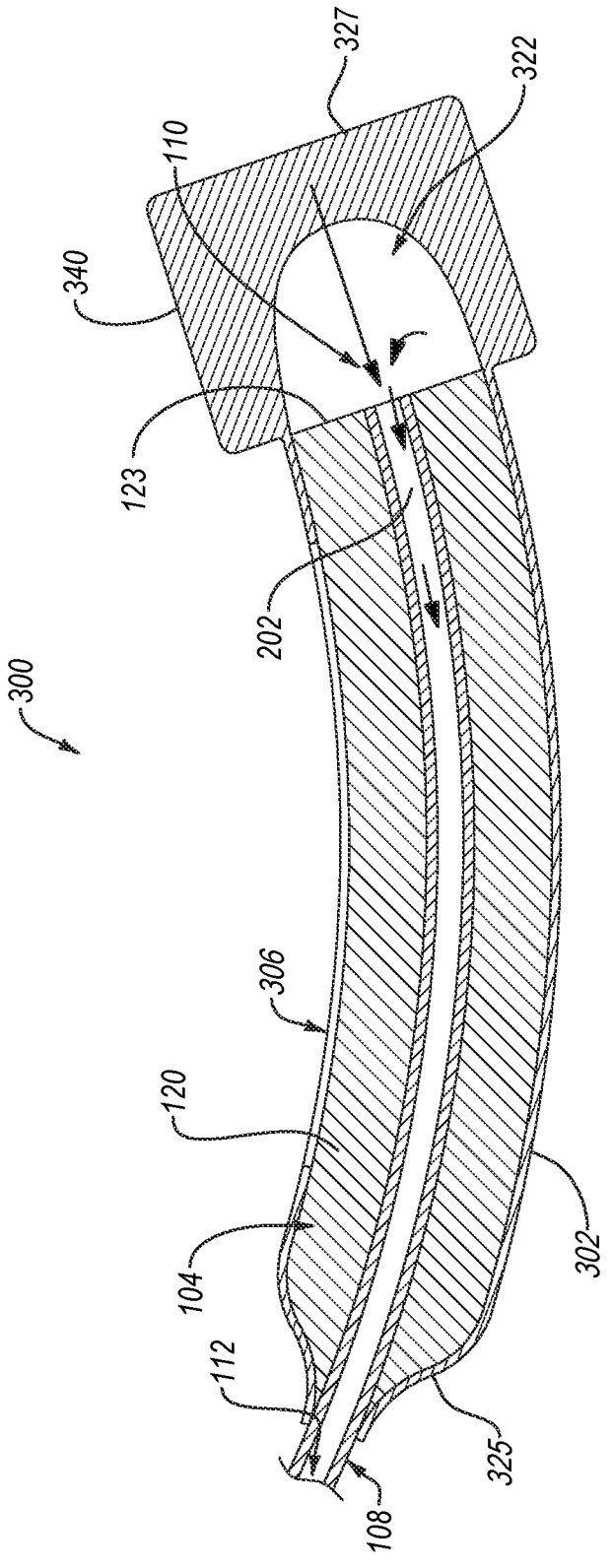
FIG. 3B is a cross-sectional view of the fluid collection device of FIG. 3A taken along line 3-3 thereof, according to various embodiments.

Turning to FIG. 3B, which is a cross-sectional view of the fluid collection device 300 of FIG. 3A taken along line 3-3. In some embodiments, the base 340 of the fluid collection device 300 includes one or more of the same or similar materials as the fluid impermeable barrier 302. Accordingly, the base 340 may be substantially continuous with the fluid impermeable barrier 302, or the material of the base 340 and the fluid impermeable barrier 302 may be coextensive with one another. In other embodiments, the base 340 may include any of the materials provided above in relation to the base 140 (such as a foam or a gel material).

The fluid collection device 300 also includes a reservoir 322. Unless otherwise noted, the reservoir 322 may include any aspects of the reservoir 122 described above. For example, the reservoir 322 may include an unoccupied portion of the fluid collection device 300 that is void of other material. The reservoir 322 also may be positioned at least partially (e.g. entirely) within the base 340. Accordingly, the base 340 may include an inner surface defining at least a portion of the reservoir 322. In the fluid collection device 300 shown in the FIG. 3B, the reservoir 322 is defined at least partially by both the second body end 123 of the fluid permeable body 120 and also an inner surface of the base 340. In some embodiments, the reservoir 322 may be positioned partially within the cylindrical portion of the fluid impermeable barrier 302 and partially within the base 340.

Figure 4:
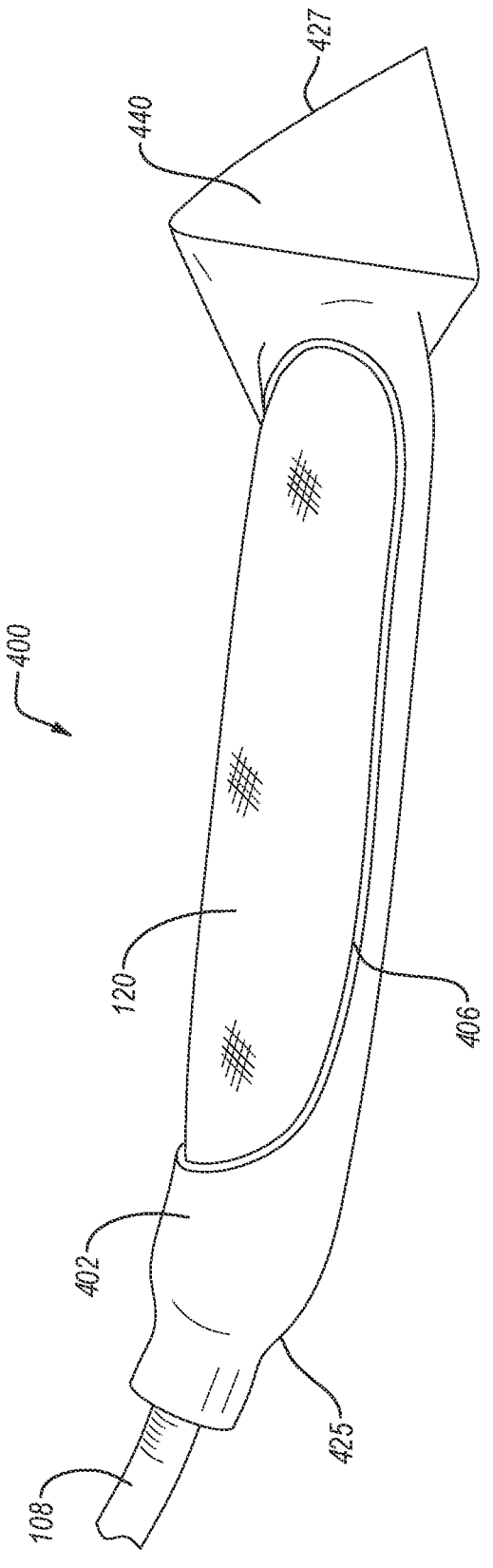
FIG. 4 is an isometric view of a fluid collection device, according to an embodiment.

FIG. 4 is an isometric view of a fluid collection device 400. Unless otherwise noted, the fluid collection device 400 includes any aspect and any technical effect of the fluid collection devices 100 or 300 described above. For example, the fluid collection device 400 includes a conduit 108 and a fluid permeable body 120 that may include any aspects of the conduit 108 and the fluid permeable body 120 described above in relation to the fluid collection device 100. The fluid collection device 400 also includes a fluid impermeable barrier 402. Unless otherwise noted, the fluid impermeable barrier 402 may include any aspect of the fluid impermeable barrier 102 or 302, such as an aperture 124 and a chamber 104. The fluid impermeable barrier 402 also includes a first end region 425 similar to the first end region 125 of the fluid collection device 100 and an opening 406 similar to the opening 106 defined by the fluid impermeable barrier 402.

The fluid collection device 400 also includes an enlarged base 440 having a generally pyramid shape that narrows away from the opening 406. In the fluid collection device 400, the base 440 forms the second end region 427 of the fluid impermeable barrier 402. Accordingly, the base 440 may include the same or similar material as the fluid impermeable barrier 402, such as any of the materials described above in relation to the fluid impermeable barrier 102. In some embodiments, the base 440 may be secured to or extend from a second end region of the fluid impermeable barrier 402, similar to the base 140 of the fluid collection device 100. Accordingly, in some embodiments, the base 440 may include materials different from the fluid impermeable barrier 402, including any of the materials provided above in relation to the base 140 (such as a foam or a gel material).

The base 440 may include a longitudinal dimension or length similar or equal to any of the longitudinal lengths $L_2$ described above in relation to the base 140. The base 440 may include a lateral dimension or width similar or equal to any of the lateral widths $W_2$ described above in relation to the base 140. The base 440 may include a height similar or equal to any of heights described above in relation to the base 140. The fluid collection device 400 also may include a reservoir similar to the reservoir 122 or 322 and positioned at least partially within at least one of the fluid impermeable barrier 402 or the base 440.

The base 440 may include various orientations with respect to the remainder of the fluid impermeable barrier 402 and the opening 406. For example, the base 440 may be oriented such that an edge or corner of the pyramid base 440 is generally centered between elongated edges of the fluid impermeable barrier 402 defining the opening 406. The base 440, then, may form a peaked edge rising from the fluid impermeable barrier 402 that is centered between elongated edges of the fluid impermeable barrier 402 and positioned to extend between and complement the buttocks of the user. In some embodiments, the base 440 may be oriented such that the opening 406 is generally centered or positioned between two adjacent edges or corners of the base 440. The cylindrical portion of the fluid impermeable barrier 402 may be generally centered relative to the pyramid base 440. In some embodiments, the cylindrical portion of the fluid impermeable barrier 402 may be misaligned with a center of the pyramid base 440, or the cylindrical portion of the fluid impermeable barrier 402 may not be centrally aligned with the pyramid base 440. For example, a rear surface of the cylindrical portion of the fluid impermeable barrier 402 distal to the opening 406 may be generally aligned with or proximate to a rear surface of the base 440. In some embodiments, an upper surface of the cylindrical portion of the fluid impermeable barrier 402 may be generally aligned with or proximate to an upper surface of the base 440.

Figure 5:
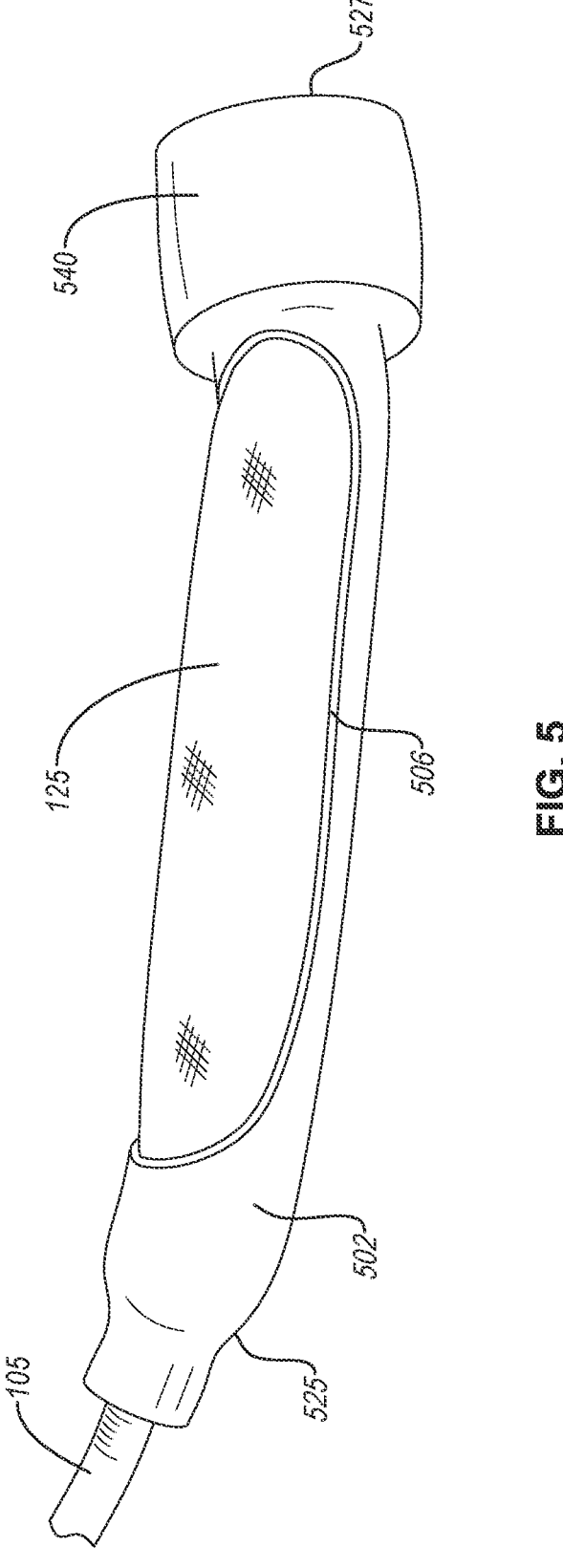
FIG. 5 is an isometric view of a fluid collection device, according to an embodiment.

FIG. 5 is an isometric view of a fluid collection device 500. Unless otherwise noted, the fluid collection device 500 includes any aspect and any technical effect of the fluid collection devices 100, 300, or 400 described above. For example, the fluid collection device 500 includes a conduit 108 and a fluid permeable body 120 that may include any aspects of the conduit 108 and the fluid permeable body 120 described above in relation to the fluid collection device 100. The fluid collection device 500 also includes a fluid impermeable barrier 502. Unless otherwise noted, the fluid impermeable barrier 502 may include any aspect of the fluid impermeable barrier 102, 302, or 402, such as an aperture 124 and a chamber 104. The fluid impermeable barrier 502 also includes a first end region 525 similar to the first end region 125 of the fluid collection device 100 and an opening 506 similar to the opening 106 defined by the fluid impermeable barrier 502.

The fluid collection device 500 also includes an enlarged base 540 having a generally cylindrical shape larger than the cylinder of the fluid impermeable barrier 502. In the fluid collection device 500, the base 540 forms the second end region 527 of the fluid impermeable barrier 502. Accordingly, the base 540 may include the same or similar material as the fluid impermeable barrier 502, such as any of the materials described above in relation to the fluid impermeable barrier 102. In some embodiments, the base 540 may be secured to or extend from a second end region of the fluid impermeable barrier 502, similar to the base 140 of the fluid collection device 100. Accordingly, in some embodiments, the base 540 may include materials different from the fluid impermeable barrier 502, including any of the materials provided above in relation to the base 140 (such as a foam or a gel material).

The base 540 may include a longitudinal dimension or length similar or equal to any of the longitudinal lengths $L_2$ described above in relation to the base 140. The base 540 may include a lateral dimension or width similar or equal to any of the lateral widths $W_2$ described above in relation to the base 140. The base 540 may include a height similar or equal to any of heights described above in relation to the base 140. The fluid collection device 500 also may include a reservoir similar to the reservoir 122 or 322 and positioned at least partially within at least one of the fluid impermeable barrier 502 or the base 540.

The base 540 may include various orientations with respect to the remainder of the fluid impermeable barrier 502 and the opening 506. For example, the base 540 may be oriented such that the opening 506 is generally centered relative to the base 540. The cylindrical portion of the fluid impermeable barrier 502 may be generally centered relative to the base 540. In some embodiments, the cylindrical portion of the fluid impermeable barrier 502 may be misaligned with a center of the base 540, or the cylindrical portion of the fluid impermeable barrier 502 may not be centrally aligned with the base 540. For example, a rear surface of the cylindrical portion of the fluid impermeable barrier 502 distal to the opening 506 may be generally aligned with or proximate to a rear surface of the base 540. In some embodiments, an upper surface of the cylindrical portion of the fluid impermeable barrier 502 may be generally aligned with or proximate to an upper surface of the base 540.

Figure 6:
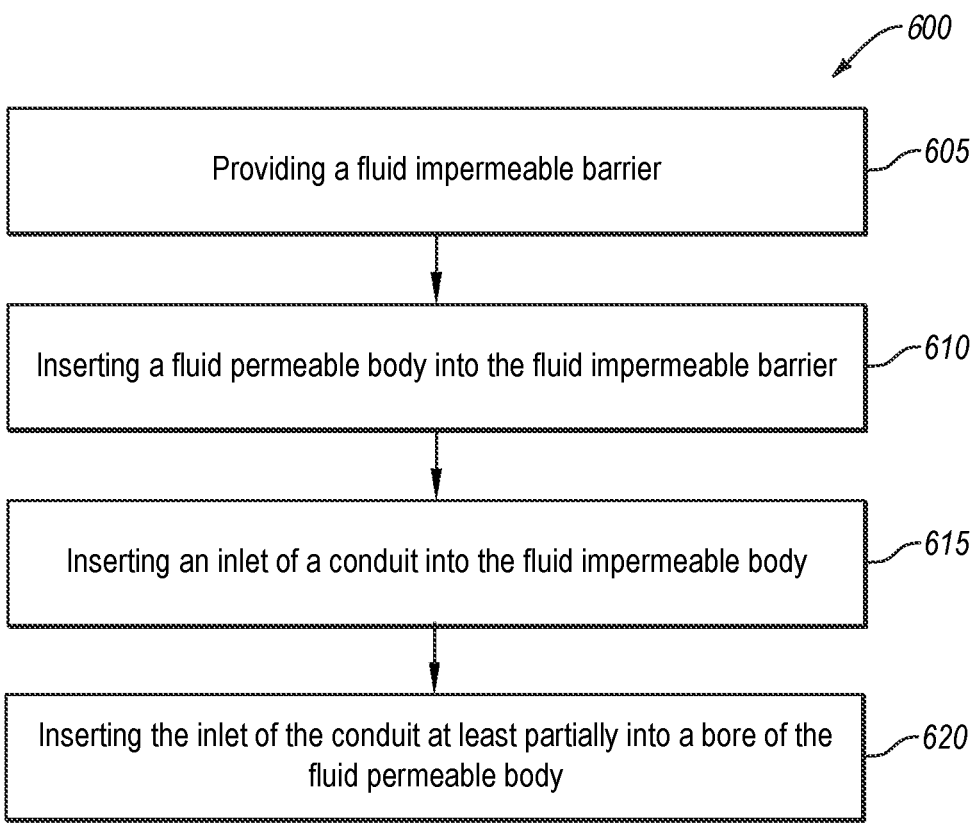
FIG. 6 is a flow diagram of a method of assembling a fluid collection device, according to an embodiment.

FIG. 6 is a flow diagram of a method 600 of assembling the fluid collection devices and/or fluid collection systems disclosed herein, according to an embodiment. The method 600 may include act 605, which recites providing a fluid impermeable barrier. The fluid impermeable barrier at least partially defines a chamber and also an opening extending therethrough. The opening is configured to be positioned adjacent to a female urethra or have a male urethra positioned therethrough. The fluid permeable body may include a singular porous hydrophilic polyolefin material extruded, molded, or sintered to a substantially cylindrical shape The method may include act 610, which recites inserting a substantially cylindrical and fluid permeable body into the chamber of the fluid impermeable barrier. When the fluid permeable body is inserted into the chamber of the fluid impermeable barrier, the fluid permeable body interfaces at least a portion of the fluid impermeable barrier and covers at least a portion of the opening. The fluid permeable body includes a singular porous material that is substantially cylindrical in shape and configured to wick any fluid away from the opening. In some embodiments, act 610 may include inserting the fluid permeable body into the chamber of the fluid impermeable barrier such that a reservoir is defined within the chamber by a second body end of the fluid permeable body distal to the first body end and a second end region of the fluid impermeable barrier distal to the aperture. In some embodiments, act 610 may include inserting the substantially cylindrical and fluid permeable body into the chamber of the fluid impermeable barrier such that the fluid permeable body and the conduit fill substantially all of the chamber.

The method may include act 615, which recites inserting an inlet of a conduit into the fluid impermeable body. The conduit may be inserted into the fluid impermeable body through an aperture defined by the fluid impermeable barrier at a first end region of the fluid impermeable barrier. In some embodiments, act 615 may include inserting the inlet of the conduit into the bore at the first body end, through the bore of the fluid permeable body, through the second body end of the fluid permeable body, and into the reservoir such that the conduit extends from the reservoir, through the fluid permeable body, through the aperture to outside the fluid impermeable barrier.

The method may include an act 620, which recites inserting the inlet of the conduit at least partially into a bore at a first body end of the fluid permeable body. The bore extends at least partially through the fluid permeable body and is defined by the fluid permeable body. The conduit interfaces at least a portion of the fluid permeable body.

Acts 605, 610, 615, and 620 of the method 600 are for illustrative purposes. For example, the acts 605, 610, 615, and 620 of the method 600 may be performed in different orders, split into multiple acts, modified, supplemented, or combined. In an embodiment, one or more of the acts 605, 610, 615, and 620 of the method 600 may be omitted from the method 600. Any of the acts 605, 610, 615, and 620 may include using any of the fluid collection devices or systems disclosed herein.

Figure 7:
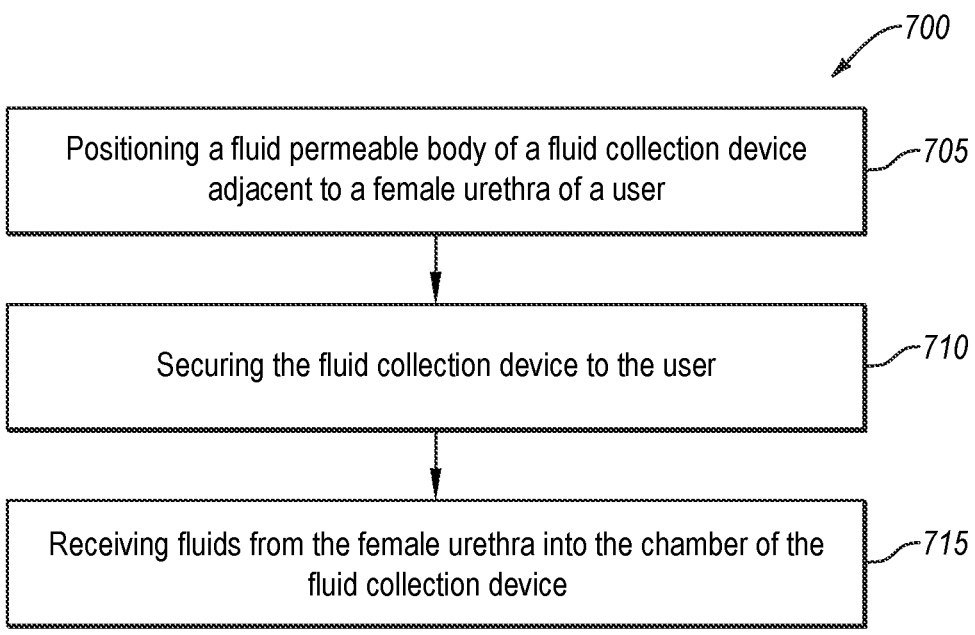
FIG. 7 is a flow diagram of a method to collect fluid, according to an embodiment.

FIG. 7 is a flow diagram of a method 700 for positioning a urine collection system on an individual and/or collecting fluids from the individual. The method 700 includes an act 705 of positioning a fluid permeable body of a fluid collection device adjacent to a female urethra of a user. In other embodiments, the fluid permeable body of the fluid collection device may be placed over the urethra of a man having a buried penis. The fluid permeable body is disposed within a chamber of a fluid impermeable barrier of the fluid collection device and exposed to the urethra of the user through an opening in the fluid collection device defined by the fluid impermeable barrier.

The method 700 also includes an act 710 of securing the fluid collection device to the user. Securing the fluid collection device to the user may include positioning a base of the fluid collection device between the buttocks of the user. The base positioned between the buttocks of the user may have a lateral dimension that is greater than a lateral dimension of the fluid impermeable barrier. The base positioned between the buttocks of the user may include at least one of a closed cell foam or a gel material. The base of the fluid collection device may interface with the buttocks effective to retain the base between the buttocks with the fluid permeable body positioned at least proximate to the urethra.

The method 700 also includes an act 715 of receiving fluids from the female urethra into the chamber of the fluid collection device. In some embodiments, the method 700 an act of applying suction effective to suction the fluids from the chamber via a conduit disposed therein.

Acts 705, 710, and 715 of the method 700 are for illustrative purposes. For example, the acts 705 and 710 of the method 700 may be performed in different orders, split into multiple acts, modified, supplemented, or combined. In an embodiment, one or more of the acts 705 or 710 of the method 700 may be omitted from the method 700. Any of the acts 705, 710, or 715 may include using any of the fluid collection devices or systems disclosed herein.

Figure 8:
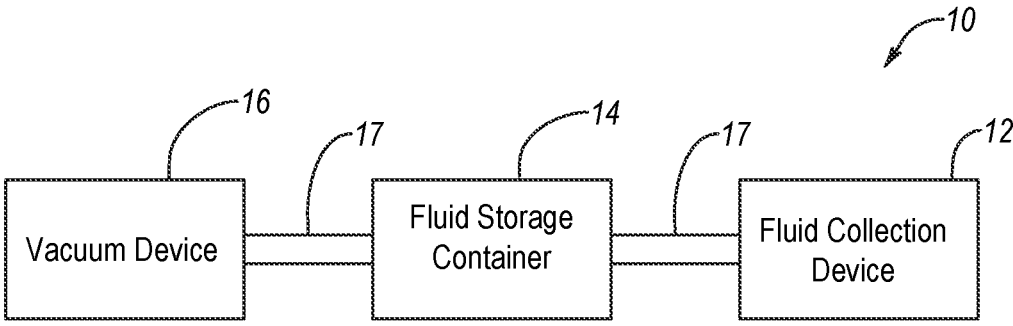
FIG. 8 is a block diagram of a system for fluid collection, according to an embodiment.

FIG. 8 is a block diagram of a system 10 for fluid collection, according to an embodiment. The system 10 includes a fluid collection device 12, a fluid storage container 14, and a vacuum source 16. The fluid collection device 12 may include any of the fluid collection devices described herein, such as the fluid collection device 100, 300, 400, or 500. The fluid collection device 12, the fluid storage container 14, and the vacuum source 16 may be fluidly coupled to each other via one or more conduits 17. The conduit 17 may include any of the conduits described herein, such as the conduit 108. The fluid collection device 12 may be operably coupled to one or more of the fluid storage container 14 or the portable vacuum source via the conduit 17. Fluid (e.g., urine or other bodily fluids) collected in the fluid collection device 12 may be removed from the fluid collection device 12 via the conduit 17, which protrudes into an interior region of the fluid collection device 12. For example, a first open end of the conduit 17 may extend into the fluid collection device 12 to a reservoir therein. The second open end of the conduit 17 may extend into the fluid storage container 14 or the vacuum source 16. The suction force may be introduced into the interior region of the fluid collection device 12 via the first open end of the conduit 17 responsive to a suction (e.g., vacuum) force applied at the second end of the conduit 17. The suction force may be applied to the second open end of the conduit 17 by the vacuum source 16 either directly or indirectly.

The suction force may be applied indirectly via the fluid storage container 14. For example, the second open end of the conduit 17 may be disposed within the fluid storage container 14 and an additional conduit 17 may extend from the fluid storage container 14 to the vacuum source 16. Accordingly, the vacuum source 16 may apply suction to the fluid collection device 12 via the fluid storage container 14.

The suction force may be applied directly via the fluid storage container 14. For example, the second open end of the conduit 17 may be disposed within the vacuum source 16. An additional conduit 17 may extend from the vacuum source 16 to a point outside of the fluid collection device 12, such as to the fluid storage container 14. In such examples, the vacuum source 16 may be disposed between the fluid collection device 12 and the fluid storage container 14.

The fluid collection device 12 may be shaped and sized to be positioned adjacent to a female urethra. The fluid collection member of the fluid collection device 12 may include a fluid impermeable barrier at least partially defining a chamber (e.g., interior region of the fluid collection device member) of the fluid collection device 12. As described in more detail above, the fluid collection device 12 may include a softer, thinner fluid impermeable barrier than conventional fluid collection devices. The fluid impermeable barrier also defines an opening extending therethrough from the external environment. The opening may be positioned on the fluid collection member to be aligned adjacent to a female urethra. The fluid collection member of the fluid collection device 12 may include a fluid permeable body disposed within the fluid impermeable barrier. The fluid permeably body may include a fluid permeable membrane and fluid permeable support disposed within the fluid permeable membrane. The conduit 17 may extend into the fluid collection device 12 at a first end region, through one or more of the fluid impermeable barrier, fluid permeable membrane, or the fluid permeable support to a second end region of the fluid collection member of the fluid collection device 12. Example fluid collection devices for use with the systems and methods herein are described in more detail below.

In some embodiments, the fluid storage container 14 may include a bag (e.g., drainage bag), a bottle or cup (e.g., collection jar), or any other enclosed container for storing bodily fluids such as urine. In examples, the conduit 17 may extend from the fluid collection device 12 and attach to the fluid storage container 14 at a first point therein. An additional conduit 17 may attach to the fluid storage container 14 at a second point thereon and may extend and attach to the vacuum source 16. For example, the fluid storage container 14 may include a container fluidly coupled to a first conduit section that is also fluidly coupled to the fluid collection member of the fluid collection device 12. The container may be fluidly coupled to a second section of the conduit 17 that is also fluidly coupled to a portable vacuum source. In such examples, the vacuum source 16 may provide a vacuum/suction through the container to the fluid collection member to provide suction in the chamber of the fluid collection member. Accordingly, a vacuum (e.g., suction) may be drawn through fluid collection device 12 via the fluid storage container 14. As the fluid is drained from the chamber, the fluid may travel through the first section of conduit to the fluid storage container where it may be retained. Fluid, such as urine, may be drained from the fluid collection device 12 using the portable vacuum source 16.

In some embodiments, the vacuum source 16 may be disposed in or on the fluid collection device 12. In such examples, the conduit 17 may extend from the fluid collection device and attach to the vacuum source 16 at a first point therein. An additional conduit 17 may attach to the vacuum source 16 at a second point thereon and may extend out of the fluid collection device 12, and may attach to the fluid storage container 14. Accordingly, a vacuum (e.g., suction) may be drawn through fluid collection device 12 via the fluid storage container 14.

The vacuum source 16 may be portable and may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 16 may provide a vacuum or suction to remove fluid from the fluid collection member of the fluid collection device 12. In some embodiments, the vacuum source 16 may be powered by one or more of a power cord (e.g., connected to a power socket), one or more batteries, or even manual power (e.g., a hand operated vacuum pump). In examples, the vacuum source 16 may be sized and shaped to fit outside of, on, or within the fluid collection device 12. For example, the vacuum source 16 may include one or more miniaturized pumps or one or more micro pumps. The portable vacuum sources 16 disclosed herein may include one or more of a switch, a button, a plug, a remote, or any other device suitable to activate the vacuum source 16. It should be understood that the vacuum sources 16 disclosed herein may provide a portable means of providing a suction or vacuum that allows use of the devices and systems herein outside of hospital or care facility environments where vacuum lines are plumbed into patient rooms or large (e.g., larger or heavier than a patient can readily carry) vacuum sources are located. For example, a portable vacuum source may be small and light enough to be carried by a user (e.g., patient) or aid (e.g., nurse) during transportation of the user.

As used herein, the term "about" or "substantially" refers to an allowable variance of the term modified by "about" by ±10% or ±5%. Further, the terms "less than," "or less," "greater than", "more than," or "or more" include as an endpoint, the value that is modified by the terms "less than," "or less," "greater than," "more than," or "or more."

While various aspects and embodiments have been disclosed herein, other aspects and embodiments are contemplated. The various aspects and embodiment disclosed herein are for purposes of illustration and are not intended to be limiting.

What is claimed is:

1. A urine collection device, comprising:
   a fluid impermeable barrier having a first lateral dimension and at least partially defining a chamber, an aperture configured to receive a conduit therethrough, and an opening, wherein the fluid impermeable barrier includes a front region at least partially defining the opening and positioned a first distance from a longitudinal axis of the fluid impermeable barrier;
   a base extending from the fluid impermeable barrier distal to the aperture and having a second lateral dimension greater than the first lateral dimension, wherein the base includes a front region having an outer periphery that is positioned a second distance from the longitudinal axis that is greater than the first distance of the front region of the fluid impermeable barrier from the longitudinal axis, the base being compressible and configured to aid in securement of the urine collection device between legs of a user with the opening at least proximate to a urethra of the user; and
   a fluid permeable body positioned at least partially within the chamber to extend across at least a portion of the opening, the fluid permeable body configured to wick fluid away from the opening.

2. The urine collection device of claim 1, wherein the second lateral dimension is at least 1.5 times greater than the first lateral dimension.

3. The urine collection device of claim 1, wherein the first lateral dimension is less than about 2.5 cm and the second lateral dimension is at least about 3.8 cm.

4. The urine collection device of claim 1, wherein the fluid impermeable barrier is generally cylindrical and the first lateral dimension includes a diameter of the fluid impermeable barrier.

5. The urine collection device of claim 4, wherein the base is generally spherical and the second lateral dimension includes a base diameter greater than the diameter of the fluid impermeable barrier.

6. The urine collection device of claim 4, wherein the base is generally rectangular cuboidal.

7. The urine collection device of claim 4, wherein the base is generally conical, frustoconical, or polyhedronal and narrows away from fluid impermeable barrier.

8. The urine collection device of claim 4, wherein the base is generally cylindrical and the second lateral dimension includes a base diameter greater than the diameter of the fluid impermeable barrier.

9. The urine collection device of claim 1, wherein the base includes a closed cell foam material.

10. The urine collection device of claim 1, wherein the base includes a gel material.

11. The urine collection device of claim 1, wherein the base includes a shore A durometer of about 5 to about 20.

12. The urine collection device of claim 1, further comprising a reservoir within the chamber, wherein the base is fluid impermeable and the reservoir is positioned at least partially within and defined at least partially by the base.

13. A urine collection device, comprising:

a fluid impermeable barrier having a first lateral dimension and at least partially defining a chamber sized and dimensioned to house a fluid permeable body, an aperture configured to receive a conduit therethrough, and an opening, wherein the fluid impermeable barrier includes a front region at least partially defining the opening and positioned a first distance from a longitudinal axis of the fluid impermeable barrier; and a base extending from the fluid impermeable barrier distal to the aperture and having a second lateral dimension greater than the first lateral dimension, wherein the base includes a front region having an outer periphery that is positioned a second distance from the longitudinal axis that is greater than the first distance of the front region of the fluid impermeable barrier from the longitudinal axis, the opening being positioned between the base and the aperture, wherein the base is compressible and configured to aid in securement of the urine collection device between legs of a user with the opening at least proximate to a urethra of the user.

14. The urine collection device of claim 13, wherein the second lateral dimension is at least 1.5 times greater than the first lateral dimension.

15. The urine collection device of claim 13, wherein the first lateral dimension is less than about 2.5 cm and the second lateral dimension is at least about 3.8 cm.

16. The urine collection device of claim 13, wherein the fluid impermeable barrier is generally cylindrical and the first lateral dimension includes a diameter of the fluid impermeable barrier.

17. The urine collection device of claim 16, wherein the base is generally spherical and the second lateral dimension includes a base diameter greater than the diameter of the fluid impermeable barrier.

18. The urine collection device of claim 16, wherein the base is generally rectangular cuboidal.

19. The urine collection device of claim 16, wherein the base is generally conical, frustoconical, or polyhedronal and narrows away from fluid impermeable barrier.

20. The urine collection device of claim 16, wherein the base is generally cylindrical and the second lateral dimension includes a base diameter greater than the body diameter.

21. The urine collection device of claim 13, wherein the base includes a closed cell foam material.

22. The urine collection device of claim 13, wherein the base includes a gel material.

23. The urine collection device of claim 13, wherein the base includes a shore A durometer of about 5 to about 20.

24. A urine collection device, comprising:

a fluid impermeable barrier at least partially defining a chamber, an aperture configured to receive a conduit therethrough, and an opening, wherein the fluid impermeable barrier includes a front region at least partially defining the opening and positioned a first distance from a longitudinal axis of the fluid impermeable barrier;

a base extending from the fluid impermeable barrier distal to the aperture, the base including at least one of a closed cell foam or a gel material such that the base is compressible and configured to aid in securement of the urine collection device between legs of a user with the opening at least proximate to a urethra of the user, wherein the base includes a front region having an outer periphery that is positioned a second distance from the longitudinal axis that is greater than the first distance of the front region of the fluid impermeable barrier from the longitudinal axis; and a fluid permeable body positioned at least partially within the chamber to extend across at least a portion of the opening, the fluid permeable body configured to wick fluid away from the opening.

25. The urine collection device of claim 24, wherein the base includes a shore A durometer of about 5 to about 20.

26. The urine collection device of claim 24, wherein the fluid impermeable barrier and the base are generally cylindrical and coextensive.

27. The urine collection device of claim 24, wherein the fluid impermeable barrier has a first lateral dimension and the base has a second lateral dimension at least 1.5 times greater than the first lateral dimension.

28. The urine collection device of claim 27, wherein the first lateral dimension is less than about 2.5 cm and the second lateral dimension is at least about 3.8 cm.

29. The urine collection device of claim 27, wherein the fluid impermeable barrier is generally cylindrical and the first lateral dimension includes a diameter of the fluid impermeable barrier.

30. The urine collection device of claim 29, wherein the base is generally spherical and the second lateral dimension includes a base diameter greater than the diameter of the fluid impermeable barrier.

31. The urine collection device of claim 29, wherein the base is generally rectangular cuboidal.

32. The urine collection device of claim 29, wherein the base is generally conical, frustoconical, or polyhedronal and narrows away from fluid impermeable barrier.

33. The urine collection device of claim 29, wherein the base is generally cylindrical and the second lateral dimension includes a base diameter greater than the body diameter.

34. The urine collection device of claim 24, further comprising a reservoir within the chamber defined at least partially by the fluid permeable body, the reservoir being positioned at least partially within and at least partially defined by the base.

35. The urine collection device of claim 24, further comprising a reservoir within the chamber defined at least partially by the fluid permeable body, wherein the reservoir is absent from within the base.

36. A method of positioning a urine collection system on an individual, the method comprising:

positioning a fluid permeable body of a fluid collection device adjacent to a urethra of a user, the fluid permeable body being positioned within a chamber defined by a fluid impermeable barrier of the fluid collection device to extend across at least a portion of an opening defined by a front region of the fluid impermeable barrier positioned a first distance from a longitudinal axis of the fluid impermeable barrier; and positioning a base of the fluid collection device between the buttocks of the user, the base being compressible and aiding in securement of the urine collection device between legs of the user with the opening adjacent to the urethra of the user, the base including a front region having an outer periphery that is positioned a second distance from the longitudinal axis that is greater than the first distance of the front region of the fluid impermeable barrier from the longitudinal axis, the base having one or more of (1) a lateral dimension that is greater than a lateral dimension of the fluid impermeable barrier; or (2) at least one of a closed cell foam or a gel material.

37. The method of claim 36, wherein positioning a base of the fluid collection device between the buttocks of the user includes positioning a generally spherical base of the fluid collection device between the buttocks of the user.

38. The method of claim 36, wherein positioning a base of the fluid collection device between the buttocks of the user includes positioning a generally rectangular cuboidal base of the fluid collection device between the buttocks of the user.

39. The method of claim 36, wherein positioning a base of the fluid collection device between the buttocks of the user includes positioning a generally conical, frustoconical, or polyhedronal base that narrows away from fluid impermeable barrier between the buttocks of the user.

40. The method of claim 36, wherein positioning a base of the fluid collection device between the buttocks of the user includes positioning a base having a shore A durometer of about 5 to about 20 between the buttocks of the user.

41. The method of claim 36, further comprising providing fluid communication between the chamber in the fluid collection device and a vacuum source.

* * * * *